US012569521B2

(12) United States Patent
Whitfill

(10) Patent No.: US 12,569,521 B2
(45) Date of Patent: Mar. 10, 2026

(54) METHODS AND COMPOSITIONS FOR TREATING INFLAMMATORY SKIN DISEASE WITH RECOMBINANT MICROORGANISMS

(71) Applicant: Azitra Inc, Farmington, CT (US)

(72) Inventor: Travis Michael Whitfill, Dallas, TX (US)

(73) Assignee: Azitra Inc, Farmington, CT (US)

( * ) Notice: Subject to any disclaimer, the term of this patent is extended or adjusted under 35 U.S.C. 154(b) by 0 days.

(21) Appl. No.: 18/641,696

(22) Filed: Apr. 22, 2024

(65) Prior Publication Data

US 2025/0090599 A1      Mar. 20, 2025

Related U.S. Application Data

(63) Continuation of application No. 16/121,903, filed on Sep. 5, 2018.

(51) Int. Cl.

| | |
|---|---|
| *A61K 39/085* | (2006.01) |
| *A61K 35/00* | (2006.01) |
| *A61K 35/74* | (2015.01) |
| *A61K 38/17* | (2006.01) |
| *A61P 17/00* | (2006.01) |
| *C07K 14/47* | (2006.01) |
| *C07K 14/71* | (2006.01) |
| *C12R 1/45* | (2006.01) |

(52) U.S. Cl.
CPC ............ *A61K 35/74* (2013.01); *A61K 38/179* (2013.01); *A61K 39/085* (2013.01); *A61P 17/00* (2018.01); *C07K 14/71* (2013.01); *A61K 2035/115* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 10,702,558 B2 | 7/2020 | Munivar et al. | |
| 11,850,267 B2 * | 12/2023 | Whitfill ................... | A61P 17/00 |
| 12,036,248 B2 * | 7/2024 | Munivar .................. | C12N 1/20 |
| 2011/0236325 A1 | 9/2011 | Mitchell et al. | |
| 2013/0018000 A1 | 1/2013 | Stout | |
| 2016/0199513 A1 | 7/2016 | Bancel et al. | |
| 2016/0220701 A1 | 8/2016 | March et al. | |
| 2017/0051260 A1 | 2/2017 | Bermudes et al. | |
| 2019/0298780 A1 | 10/2019 | Whitfill | |

FOREIGN PATENT DOCUMENTS

| | | |
|---|---|---|
| CN | 106062000 A | 10/2016 |
| JP | 2017-518370 A | 7/2017 |
| WO | 2009/112301 A2 | 9/2009 |
| WO | 2015/117021 A1 | 8/2015 |
| WO | 2015/184134 A1 | 12/2015 |
| WO | 2017/136652 A1 | 8/2017 |

OTHER PUBLICATIONS

Sohn et al. Mount Sinai J. of Medicine 78:730-739, 2011.*
U.S. Appl. No. 16/121,903, filed Sep. 5, 2018, 2019-0298780, Published.
Boguniewicz et al., Atopic dermatitis: a disease of altered skin barrier and immune dysregulation. Immunol Rev. Jul. 2011;242(1):233-46.
Ma et al., Cell-penetrating peptides mediated protein cross-membrane delivery and its use in bacterial vector vaccine. Fish Shellfish Immunol. Jul. 2014;39(1):8-16.
NCBI Accession No. NP_002007, filaggrin [*Homo sapiens*]. 6 pages, Aug. 14, 2017.
International Search Report and Written Opinion for Application No. PCT/US2018/049477, dated Jan. 16, 2019, 10 pages.
International Preliminary Report on Patentability for Application No. PCT/US2018/049477, dated Mar. 10, 2020, 7 pages.

* cited by examiner

*Primary Examiner* — S. Devi

(74) *Attorney, Agent, or Firm* — McCarter & English, LLP; Jonathan M. Sparks

(57) ABSTRACT

The present invention provides isolated plasmids, recombinant microorganisms, kits, and methods for the treatment of inflammatory skin disease.

6 Claims, 24 Drawing Sheets

Specification includes a Sequence Listing.

Time (AD disease progression)

H hFLG (4061 aa)

Segment Analysis (hFLG Domains 9-10)

FROM FIG. 13A

```
hFLG[ 3- 4]  HHEASSQADSSRHSQVGQGQSSGPRTSRNQGSSVSQDSDSQHSEDSERWSGSASRNHHG
hFLG[ 5- 6]  HHEASSHADISRHSQAGQGQSEGSRTSRRQGSSVSQDSDSEGHSEDSERWSGSASRNHRG
hFLG[ 7- 8]  HHEASWADSSRHSQVGQGQSEGSRTSRHQGSSVSQDSDSERHSDDSERLSGSASRNHHG
hFLG[ 9-10]  HHEPSTRAGSSRHSQVGQGQSESAGSKTSRRQGSSVSQDRDSEGHSEDSERRSESASRNHYG
hFLG[11-12]  HHEASSRADSSRHSQVGQGQSSGPRTSRNQGSSVSQDSDSQHSEDSERWSGSASRNHLG
hFLG[13-14]  HHEASSWADSSRHSLVGQGQSSGPRTSRPGSSVSQDSDSEGHSEDSERWSGSASRNHHG
hFLG[15-16]  HHEASSRADSSGHSQVGQGQSEGPRTSRNWGSSFSQDSDSQHSEDSERWSGSASRNHHG
hFLG[17-18]  HHEASTHADISRHSQAVQGQSEGSRRSRRQGSSVSQDSDSEGHSEDSERWSGSASRNHRG
hFLG[19-20]  HHEASTHADISRHSQAVQGQSEGSRRSRRQGSSVSQDSDSEGHSEDSERWSGSASRNHRG
hFLG[21-22]  HHEASTQADSSRHSQSGQGQSAGPRTSRNQGSSVSQDSDSQHSEDSERWSGSASRNHRG
             ** *:*:   *        *   ***   *   * :  * ***  * hFLG[ 3- 4]  SAQEQSRDGSRHPRSHHEDRAGHGHSADSSRKSGTRHTQNSSGQAASSHEQARSSAGER
hFLG[ 5- 6]  SAQEQSRHGSRHPRSHHEDRAGHGHSADSSRQSGTPHAETSSGQAASSHEQARSSPGER
hFLG[ 7- 8]  SSREQSRDGSRHPGFHQEDRASHGHSADSSRQSGTHHTESSSHGQAVSSHEQARSSPGER
hFLG[ 9-10]  SAREQSRHGSRNPRSHQEDRASHGHSAESSRQSGTRHAETSSGQAASSQEQARSSPGER
hFLG[11-12]  SAWEQSRDGSRHPGSHHEDRAGHGHSADSSRQSGTRHTESSSRGQAASSHEQARSSAGER
hFLG[13-14]  SAQEQSRDGSRHPRSHHEDRAGHGHSADSSRQSGTRHTESSSRGQAASSHEQARSSAGER
hFLG[15-16]  SAQEQLRDGSRHPRSHQEDRAGHGHSADSSRQSGTRHTQTSSGQAASSHEQARSSAGER
hFLG[17-18]  SAQEQLRDGSRHPRSHQEDRAGHGHSADSSRQSGTRHTQTSSGQAASSHEQARSSAGER
hFLG[19-20]  SVQEQSRHGSRHPRSHHEDRAGHGHSADRSRQSGTRHAETSSGQAASSHEQARSSPGER
hFLG[21-22]  SAQEQSRDGSRHPTSHHEDRAGHGHSAESSRQSGTHHAENSSGQAASSHEQARSSAGER
             *  *: * * * :*::**:*:*** :::* *:  * : *    * *:******  **
```

FROM FIG. 13B

```
hFLG[3-4]    HGSRHQLQSADSSRHSGTGHGQASSAVRDSGHRGSSGSGQATDSEGHSEDSDTQSVSGHGQ
hFLG[5-6]    HGSRHQ-QSADSSRHSGIPRRQASSAVRDSGHWGSSGSGQASDSEGHSEESDTQSVSGHGQ
hFLG[7-8]    HGSRHQ-QSADSSRHSGIGHRQASSAVRDSGHRGSSGSGQVTNSEGHSEDSDTQSVSAHGQ
hFLG[9-10]   HGSRHQ-QSADSSTDSGTGRRQDSSVVGDSGNRGSSGSGQASDSEGHSEESDTQSVSAHGQ
hFLG[11-12]  HGSHHQLQSADSSRHSGIGHGQASSAVRDSGHRGYSGSGQASDSEGHSEDSDTQSVSAQGK
hFLG[13-14]  HGSHHQ-QSADSSRHSCIGHGQASSAVRDSGHRGSSGSGQASDSEGHSEDSDTQSVSAHGQ
hFLG[15-16]  HGSHHQ-QSADSSRHSGIGHGQASSAVRDSGHRGSSGSGQASDNEGHSEDSDTQSVSAHGQ
hFLG[17-18]  HGSHHQ-QSADSSRHSGIGHGQASSAVRDSGHRGYSGSGQASDNEGHSEDSDTQSVSAHGQ
hFLG[19-20]  HGSRHQ-QSADSSRHSGIPRGQASSAVRDSRHWGSSGSGQASDSEGHSEDSDTQSVSGHGQ
hFLG[21-22]  HGSHHQ-QSADSSRHSGIGHGQASSAVRDSGHRGSSGSGQASDSEGHSEDSDTQSVSAHGQ
             ***** .: *.  .**  * *.  :  .  .::  .*.:* hFLG[3-4]    AGHHQQSHQESARDRSGERSRRSGSFLY
hFLG[5-6]    DGPHQQSHQESARDWSGGRSGGRSGSFIY
hFLG[7-8]    AGPHQQSHKESARGQSGESSGGRSRSFLY
hFLG[9-10]   AGPHQQSHQESTRGQSGERSGRSGSFLY
hFLG[11-12]  AGPHQQSHKESARGQSGESSGERSGSFLY
hFLG[13-14]  AGPHQQSHQESTRGRSAGRSGETSGSFLY
hFLG[15-16]  AGSHQQSHQESARGRSGETSGSFLY
hFLG[17-18]  AGSHQQSHQESARGRSGGRSGSFLY
hFLG[19-20]  AGPHQQSHQESARDRSGGRSGGRSGSFLY
hFLG[21-22]  AGPHQQSHQESTRGRSAGRSGGRSGSFLY
             * **** ***.* .: *. :  * ***.*
```

- - ☐ - -    hFLG [5-6] (H6-796-1116-RMR)

---▽---    hFLG [9-10] (M-1452-1777-RMR) (790)

-----◇-----    hFLG [9-10] (M-1545-1869-RMR) (791)

——△——    hFLG [9-10] (M-1429-1774-RMR) (604)

SEQUENCE LISTING

Sequence total quantity: 52
SEQ ID NO: 1             moltype = AA   length = 4061

```
FEATURE           Location/Qualifiers
source            1..4061
                  mol_type = protein
                  organism = Homo sapiens
SEQUENCE: 1
MSTLLENIFA IIINLFKQYSK KDKNTDTLSK KELKELLEKE FRQILKNPDD PDMVDVFMDH   60
LDIDHNKKID FTEFLLMVFK LAQAYYESTR KENLPISGHK HRKHSHHDKH EDNKQEENKE  120
NRKRPSSLER RNNRKGNKGR SKSPRETGGK RHESSSEKKE RKGYSPTHRE EEYGKNHHNS  180
SKKEKNKTEN TRLGDNRKRL SERLEEKEDN EEGVYDYENT GRMTQKWIQS GHIATYYTIQ  240
DEAYDTTDSL LEENKIYERS RSSDGKSSSQ VNRSRHENTS QVPLQESRTR KRRGSRVSQD  300
RDSEGHSEDS ERHSGSASRN HHGSAWEQSR DGSRHPRSHD EDRASHGHSA DSSRQSGTRH  360
AETSSRGQTA SSHEQARSSP GERHGSGHQQ SADSSRHSAT GRGQASSAVS DRGHRGSSGS  420
QASDSEGHSE NSDTQSVSGH GKAGLRQQSH QESTRGRSGE RSGRSGSSLY QVSTHEQPDS  480
AHGRTGTSTG GRQGSHHEQA RDSSRHSASQ EGQDTIRGHP GSSRGGRQGS HHEQSVNRSG  540
HSGSHHSHTT SQGRSDASHG QSGSRSASRQ TRNEEQSGDG TRHSGSRHHE ASSQADSSRH  600
SQVGQGQSSG PRTSRNQGSS VSQDSDSQGH SEDSERWSGS ASRNHHGSAQ EQSRDGSRHP  660
RSHHEDRAGH GHSADSSRKS GTRHTQNSSS GQAASSHEQA RSSAGERHGS RHQLQSADSS  720
RHSGTGHGQA SSAVRDSGHR GSSGSQATDS EGHSEDSDTQ SVSGHGQAGH HQQSHQESAR  780
DRSGERSRRS GSFLYQVSTH KQSESSHGWT GPSTGVRQGS HHEQARDNSR HSASQDGQDT  840
IRGHPGSSRR GRQGSHHEQS VDRSGHSGSH HSHTTSQGRS DASRGQSGSR SASRTTRNEE  900
QSRDGSRHSG SRHHEASSHA DISRHSQAGQ GQSEGSRTSR RQGSSVSQDS DSEGHSEDSE  960
RWSGSASRNH RGSAQEQSRH GSRHPRSHHE DRAGHGHSAD SSRQSGTPHA ETSSGGQAAS 1020
SHEQARSSPG ERHGSRHQQS ADSSRHSGIP RRQASSAVRD SGHWGSSGSQ ASDSEGHSEE 1080
SDTQSVSGHG QDGPHQQSHQ ESARDWSGGR SGRSGSFIYQ VSTHEQSESA HGRTRTSTGR 1140
RQGSHHEQAR DSSRHSASQE GQDTIRAHPG SRRGGRQGSH HEQSVDRSGH SGSHHSHTTS 1200
QGRSDASHGQ SGSRSASRQT RKDKQSGDGS RHSGSRHHEA ASWADSSRHS QVGQEQSSGS 1260
RTSRHQGSSV SQDSDSERHS DDSERLSGSA SRNHHGSSRE QSRDGSRHPG FHQEDRASHG 1320
HSADSSRQSG THHTESSSHG QAVSSHEQAR SSPGERHGSR HQQSADSSRH SGIGHRQASS 1380
AVRDSGHRGS SGSQVTNSEG HSEDSDTQSV SAHGQAGPHQ QSHKESARGQ SGESSGRSRS 1440
FLYQVSSHEQ SESTHGQTAP STGGRQGSRH EQARNSSRHS ASQDGQDTIR GHPGSSRGGR 1500
QGSYHEQSVD RSGHSGYHHS HTTPQGRSDA SHGQSGPRSA SRQTRNEEQS GDGSRHSGSR 1560
HHEPSTRAGS SRHSQVGQGE SAGSKTSRRQ GSSVSQDRDS EGHSEDSERR SESASRNHYG 1620
SAREQSRHGS RNPRSHQEDR ASHGHSAESS RQSGTRHAET SSGGQAASSQ EQARSSPGER 1680
HGSRHQQSAD SSTDSGTGRR QDSSVVGDSG NRGSSGSQAS DDSHSEESD TQSVSAHGQA 1740
GPHQQSHQES TRGQSGERSG RSGSFLYQVS THEQSESAHG RTGPSTGGRQ RSRHEQARDS 1800
SRHSASQEGQ DTIRGHPGSS RGGRQGSHYE QSVDSSGHSG SHHSHTTSQE RSDVSRGQSG 1860
SRSVSRQTRN EKQSGDGSRH SGSRHHEASS RADSSRHSQV GQGQSSGPRT SRNQGSSVSQ 1920
DSDSQGHSED SERWSGSASR NHLGSAWEQS RDGSRHPGSH HEDRAGHGHS ADSSRQSGTR 1980
HTESSSRGQA ASSHEQARSS AGERHGSHHQ LQSADSSRHS GIGHGQASSA VRDSGHRGYS 2040
GSQASDSEGH SEDSDTQSVS AQGKAGPHQQ SHKESARGQS GESSGRSGSF LYQVSTHEQS 2100
ESTHGQSAPS TGGRQGSHYD QAQDSSRHSA SQEGQDTIRG HPGPSRGGRQ GSHQEQSVDR 2160
SGHSGSHHSH TTSQGRSDAS RGQSGSRSAS RKTYDKEQSG DGSRHSGSHH HEASSWADSS 2220
RHSLVGQGQS SGPRTSRPRG SSVSQDSDSE GHSEDSERRS GSASRNHHGS AQEQSRDGSR 2280
HPRSHHEDRA GHGHSAESSR QSGTHHAENS SGGQAASSHE QARSSAGERH GSHHQQSADS 2340
SRHSGIGHGQ ASSAVRDSGH RGSSGSQASD SEGHSEDSDT QSVSAHGQAG PHQQSHQEST 2400
RGRSAGRSGR SGSFLYQVST HEQSESAHGR TGTSTGGRQG SHHKQARDSS RHSTSQEGQD 2460
TIHGHPGSSS GGRQGSHYEQ LVDRSGHSGS HHSHTTSQGR SRASRQTRND 2520
EQSGDGSRHS GSRHHEASSR ADSSGHSQVG QGQSEGPRTS RNWGSSFSQD SDSQGHSEDS 2580
ERWSGSASRN HHGSAQEQLR DGSRHPRSHQ EDRAGHGHSA DSSRQSGTRH TQTSSGGQAA 2640
SSHEQARSSA GERHGSHHQQ SADSSRHSGI GHGQASSAVR DSGHRGYSGS QASDNEGHSE 2700
DSDTQSVSAH GQAGSHQQSH QESARGRSGE TSGHSGSFLY QVSTHEQSES SHGWTGPSTR 2760
GRQGSRHEQA QDSSRHSASQ DGQDTIRGHP GSSRGGRQGY HHEHSVDSSG HSGSHHSHTT 2820
SQGRSDASRG QSGSRSASRT TRNEEQSGDG SRHSGSRHHE ASTHADISRH SQAVQGQSEG 2880
SRRSRRQGSS VSQDSDSEGH SEDSERWSGS ASRNHHGSAQ EQLRDGSRHP RSHQEDRAGH 2940
GHSADSSRQS GTRHTQTSSG GQAASSHEQA RSSAGERHGS HHQQSADSSR HSGIGHGQAS 3000
SAVRDSGHRG YSGSQASDNE GHSEDSDTQS VSAHGQAGSH QQSHQESARG RSGETSGHSG 3060
SFLYQVSTHE QSESSHGWTG PSTRGRQGSR HEQAQDSSRH SASQYGQDTI RGHPGSSRGG 3120
RQGYHHEHSV DSSGHSGSHH SHTTSQGRSD ASRGQSGSRS ASRTTRNEEQ SGDSSRHSVS 3180
RHHEASTHAD ISRHSQAVQG QSEGSRRSRR QGSSVSQDSD SEGHSEDSER WSGSASRNHR 3240
GSVQEQSRHG SRHPRSHHED RAGHGHSADR SRQSGTRHAE TSSGGQAASS HEQARSSPGE 3300
RHGSRHQQSA DSSRHSGIPR GQASSAVRDS RHWGSSGSQA SDSEGHSEES DTQSVSGHGQ 3360
AGPHQQSHQE SARDRSGGRS GRSGSFLYQV STHEQSESAH GRTRTSTGRR QGSHHEQARD 3420
SSRHSASQEG QDTIRGHPGS SRRGRQGSHY EQSVDRSGHS GSHHSHTTSQ GRSDASRGQS 3480
GSRSASRQTR NDEQSGDGSR HSWSHHHEAS TQADSSRHSQ SGGQGSAGPR TSRNQGSSVS 3540
QDSDSQGHSE DSERWSGSAS RNHRGSAQEQ SRDGSRHPTS HHEDRAGHGH SAESSRQSGT 3600
HHAENSSGGQ AASSHEQARS SAGERHGSHH QQSADSSRHS GIGHGQASSA VRDSGHRGSS 3660
GSQASDSEGH SEDSDTQSVS AHGQAGPHQQ SHQESTRGRS AGRSGRSGSF LYQVSTHEQS 3720
ESAHGRAGPS TGGRQGSRHE QARDSSRHSA SQEGQDTIRG HPGSRRGGRQ GSYHEQSVDR 3780
SGHSGSHHSH TTSQGRSDAS HGQSGSRSAS RETRNEEQSG DGSRHSGSRH HEASTQADSS 3840
RHSQSGQGES AGSRRSRRQG SSVSQDSDSE AYPEDSERRS ESASRNHHGS SREQSRDGSR 3900
HPGSSHRDTA SHVQSSPVQS DSSTAKEHGH FSSLSQDSAY HSGIQSRGSP HSSSSYHYQS 3960
EGTERQKGQS GLVWRHGSYG SADYDYGESG FRHSQHGSVS YNSNPVVFKE RSDICKASAF 4020
GKDHPRYYAT YINKDPGLCG HSSDISKQLG FSQSQRYYYY E              4061

SEQ ID NO: 2         moltype = AA   length = 346
FEATURE              Location/Qualifiers
REGION               1..346
                     note = Description of Artificial Sequence: Synthetic
                     polypeptide
```

```
source                     1..346
                           mol_type = protein
                           organism = synthetic construct
SEQUENCE: 2
MQSGESSGRS RSFLYQVSSH EQSESTHGQT APSTGGRQGS RHEQARNSSR HSASQDGQDT  60
IRGHPGSSRG GRQGSYHEQS VDRSGHSGYH HSHTTPQGRS DASHGQSGPR SASRQTRNEE  120
QSGDGSRHSG SRHHEPSTRA GSSRHSQVGQ GESAGSKTSR RQGSSVSQDR DSEGHSEDSE  180
RRSESASRNH YGSAREQSRH GSRNPRSHQE DRASHGHSAE SSRQSGTRHA ETSSGGQAAS  240
SQEQARSSPG ERHGSRHQQS ADSSTDSGTG RRQDSSVVGD SGNRGSSGSQ ASDSEGHSEE  300
SDTQSVSAHG QAGPHQQSHQ ESTRGQSGER SGRSGSFLYQ VSTHEQ              346

SEQ ID NO: 3              moltype = AA  length = 356
FEATURE                   Location/Qualifiers
REGION                    1..356
                          note = Description of Artificial Sequence: Synthetic
                           polypeptide
source                    1..356
                          mol_type = protein
                          organism = synthetic construct
SEQUENCE: 3
MQSGESSGRS RSFLYQVSSH EQSESTHGQT APSTGGRQGS RHEQARNSSR HSASQDGQDT  60
IRGHPGSSRG GRQGSYHEQS VDRSGHSGYH HSHTTPQGRS DASHGQSGPR SASRQTRNEE  120
QSGDGSRHSG SRHHEPSTRA GSSRHSQVGQ GESAGSKTSR RQGSSVSQDR DSEGHSEDSE  180
RRSESASRNH YGSAREQSRH GSRNPRSHQE DRASHGHSAE SSRQSGTRHA ETSSGGQAAS  240
SQEQARSSPG ERHGSRHQQS ADSSTDSGTG RRQDSSVVGD SGNRGSSGSQ ASDSEGHSEE  300
SDTQSVSAHG QAGPHQQSHQ ESTRGQSGER SGRSGSFLYQ VSTHEQRMRR MRRMRR     356

SEQ ID NO: 4              moltype = AA  length = 337
FEATURE                   Location/Qualifiers
REGION                    1..337
                          note = Description of Artificial Sequence: Synthetic
                           polypeptide
source                    1..337
                          mol_type = protein
                          organism = synthetic construct
SEQUENCE: 4
MESTHGQTAP STGGRQGSRH EQARNSSRHS ASQDGQDTIR GHPGSSRGGR QGSYHEQSVD  60
RSGHSGYHHS HTTPQGRSDA SHGQSGPRSA SRQTRNEEQS GDGSRHSGSR HHEPSTRAGS  120
SRHSQVGQGE SAGSKTSRRQ GSSVSQDRDS EGHSEDSERR SESASRNHYG SAREQSRHGS  180
RNPRSHQEDR ASHGHSAESS RQSGTRHAET SSGGQAASSQ EQARSSPGER HGSRHQQSAD  240
SSTDSGTGRR QDSSVVGDSG NRGSSGSQAS DSEGHSEESD TQSVSAHGQA GPHQQSHQES  300
TRGQSGERSG RSGSFLYQVS THEQSESRMR RMRRMRR                        337

SEQ ID NO: 5              moltype = AA  length = 336
FEATURE                   Location/Qualifiers
REGION                    1..336
                          note = Description of Artificial Sequence: Synthetic
                           polypeptide
source                    1..336
                          mol_type = protein
                          organism = synthetic construct
SEQUENCE: 5
MRNEEQSGDG SRHSGSRHHE PSTRAGSSRH SQVGQGESAG SKTSRRQGSS VSQDRDSEGH  60
SEDSERRSES ASRNHYGSAR EQSRHGSRNP RSHQEDRASH GHSAESSRQS GTRHAETSSG  120
GQAASSQEQA RSSPGERHGS RHQQSADSST DSGTGRRQDS SVVGDSGNRG SSGSQASDSE  180
GHSEESDTQS VSAHGQAGPH QQSHQESTRG QSGERSGRSG SFLYQVSTHE QSESAHGRTG  240
PSTGGRQRSR HEQARDSSRH SASQEGQDTI RGHPGSSRGG RQGSHYEQSV DSSGHSGSHH  300
SHTTSQERSD VSRGQSGSRS VSRQTRRMRR MRRMRR                         336

SEQ ID NO: 6              moltype = AA  length = 244
FEATURE                   Location/Qualifiers
REGION                    1..244
                          note = Description of Artificial Sequence: Synthetic
                           polypeptide
source                    1..244
                          mol_type = protein
                          organism = synthetic construct
SEQUENCE: 6
MRNEEQSGDG SRHSGSRHHE PSTRAGSSRH SQVGQGESAG SKTSRRQGSS VSQDRDSEGH  60
SEDSERRSES ASRNHYGSAR EQSRHGSRNP RSHQEDRASH GHSAESSRQS GTRHAETSSG  120
GQAASSQEQA RSSPGERHGS RHQQSADSST DSGTGRRQDS SVVGDSGNRG SSGSQASDSE  180
GHSEESDTQS VSAHGQAGPH QQSHQESTRG QSGERSGRSG SFLYQVSTHE QSESRMRRMR  240
RMRR                                                            244

SEQ ID NO: 7              moltype =    length =
SEQUENCE: 7
000

SEQ ID NO: 8              moltype = AA  length = 352
```

```
FEATURE          Location/Qualifiers
REGION           1..352
                 note = Description of Artificial Sequence: Synthetic
                  polypeptide
source           1..352
                 mol_type = protein
                 organism = synthetic construct
SEQUENCE: 8
MRSRSFLYQV SSHEQSESTH GQTAPSTGGR QGSRHEQARN SSRHSASQDG QDTIRGHPGS 60
SRGGRQGSYH EQSVDRSGHS GYHHSHTTPQ GRSDASHGQS GPRSASRQTR NEEQSGDGSR 120
HSGSRHHEAS TRADSSRHSQ VGQGQSSGSR TSRRQGSSVS QDSDSEGHSE DSERRSGSAS 180
RNHYGSAQEQ SRDGSRHPRS HQEDRASHGH SAESSRQSGT RHAETSSGGQ AASSHEQARS 240
SPGERHGSRH QQSADSSRHS GIGHGQASSA VRDSGHRGSS GSQASDSEGH SEDSDTQSVS 300
AHGQAGPHQQ SHQESARGRS GERSGRSGSF LYQVSTHEQS ESRMRRMRRM RR           352

SEQ ID NO: 9     moltype = AA  length = 328
FEATURE          Location/Qualifiers
REGION           1..328
                 note = Description of Artificial Sequence: Synthetic
                  polypeptide
VARIANT          1
                 note = MOD_RES - Any amino acid
VARIANT          9
                 note = MOD_RES - Any amino acid
VARIANT          11
                 note = MOD_RES - Any amino acid
VARIANT          14
                 note = MOD_RES - Any amino acid
VARIANT          17
                 note = MOD_RES - Any amino acid
VARIANT          19..20
                 note = MOD_RES - Any amino acid
VARIANT          23..24
                 note = MOD_RES - Any amino acid
VARIANT          27
                 note = MOD_RES - Any amino acid
VARIANT          30..31
                 note = MOD_RES - Any amino acid
VARIANT          34..36
                 note = MOD_RES - Any amino acid
VARIANT          41
                 note = MOD_RES - Any amino acid
VARIANT          44
                 note = MOD_RES - Any amino acid
VARIANT          55..58
                 note = MOD_RES - Any amino acid
VARIANT          63..65
                 note = MOD_RES - Any amino acid
VARIANT          67..68
                 note = MOD_RES - Any amino acid
VARIANT          70..71
                 note = MOD_RES - Any amino acid
VARIANT          77
                 note = MOD_RES - Any amino acid
VARIANT          84
                 note = MOD_RES - Any amino acid
VARIANT          86
                 note = MOD_RES - Any amino acid
VARIANT          94
                 note = MOD_RES - Any amino acid
VARIANT          97
                 note = MOD_RES - Any amino acid
VARIANT          103
                 note = MOD_RES - Any amino acid
VARIANT          105..108
                 note = MOD_RES - Any amino acid
VARIANT          111
                 note = MOD_RES - Any amino acid
VARIANT          113
                 note = MOD_RES - Any amino acid
VARIANT          118
                 note = MOD_RES - Any amino acid
VARIANT          124..125
                 note = MOD_RES - Any amino acid
VARIANT          127
                 note = MOD_RES - Any amino acid
VARIANT          129..130
                 note = MOD_RES - Any amino acid
VARIANT          132
```

| | | note = MOD_RES - Any amino acid |
| VARIANT | 135..136 | |
| | | note = MOD_RES - Any amino acid |
| VARIANT | 139..140 | |
| | | note = MOD_RES - Any amino acid |
| VARIANT | 142 | |
| | | note = MOD_RES - Any amino acid |
| VARIANT | 144 | |
| | | note = MOD_RES - Any amino acid |
| VARIANT | 146 | |
| | | note = MOD_RES - Any amino acid |
| VARIANT | 149..150 | |
| | | note = MOD_RES - Any amino acid |
| VARIANT | 154 | |
| | | note = MOD_RES - Any amino acid |
| VARIANT | 158 | |
| | | note = MOD_RES - Any amino acid |
| VARIANT | 161..162 | |
| | | note = MOD_RES - Any amino acid |
| VARIANT | 170 | |
| | | note = MOD_RES - Any amino acid |
| VARIANT | 172 | |
| | | note = MOD_RES - Any amino acid |
| VARIANT | 179 | |
| | | note = MOD_RES - Any amino acid |
| VARIANT | 182..183 | |
| | | note = MOD_RES - Any amino acid |
| VARIANT | 186 | |
| | | note = MOD_RES - Any amino acid |
| VARIANT | 188 | |
| | | note = MOD_RES - Any amino acid |
| VARIANT | 192 | |
| | | note = MOD_RES - Any amino acid |
| VARIANT | 194..195 | |
| | | note = MOD_RES - Any amino acid |
| VARIANT | 197 | |
| | | note = MOD_RES - Any amino acid |
| VARIANT | 202 | |
| | | note = MOD_RES - Any amino acid |
| VARIANT | 209 | |
| | | note = MOD_RES - Any amino acid |
| VARIANT | 216 | |
| | | note = MOD_RES - Any amino acid |
| VARIANT | 218..220 | |
| | | note = MOD_RES - Any amino acid |
| VARIANT | 223 | |
| | | note = MOD_RES - Any amino acid |
| VARIANT | 230 | |
| | | note = MOD_RES - Any amino acid |
| VARIANT | 237 | |
| | | note = MOD_RES - Any amino acid |
| VARIANT | 247 | |
| | | note = MOD_RES - Any amino acid |
| VARIANT | 254..255 | |
| | | note = MOD_RES - Any amino acid |
| VARIANT | 258..259 | |
| | | note = MOD_RES - Any amino acid |
| VARIANT | 261 | |
| | | note = MOD_RES - Any amino acid |
| VARIANT | 263 | |
| | | note = MOD_RES - Any amino acid |
| VARIANT | 268 | |
| | | note = MOD_RES - Any amino acid |
| VARIANT | 271..273 | |
| | | note = MOD_RES - Any amino acid |
| VARIANT | 275 | |
| | | note = MOD_RES - Any amino acid |
| VARIANT | 282..283 | |
| | | note = MOD_RES - Any amino acid |
| VARIANT | 298 | |
| | | note = MOD_RES - Any amino acid |
| VARIANT | 300..301 | |
| | | note = MOD_RES - Any amino acid |
| VARIANT | 303 | |
| | | note = MOD_RES - Any amino acid |
| VARIANT | 309 | |
| | | note = MOD_RES - Any amino acid |
| VARIANT | 312 | |
| | | note = MOD_RES - Any amino acid |

```
VARIANT                  314..315
                         note = MOD_RES - Any amino acid
VARIANT                  318..319
                         note = MOD_RES - Any amino acid
VARIANT                  321
                         note = MOD_RES - Any amino acid
VARIANT                  324
                         note = MOD_RES - Any amino acid
source                   1..328
                         mol_type = protein
                         organism = synthetic construct
SEQUENCE: 9
XLYQVSTHXQ XDSXHGXTXX STXXRQXSHX XQAXXXSRHS XSQXGQDTIR GHPGXXXXGR   60
QGXXXEXXVX XSGHSGXHHS HTTXQXRSDA SHGXSGXRSA SRXTXXXXQS XDXTRHSXSR  120
HHEXXSXAXX SXHSXXGQXX SXGXRXSRXX GSSXSQDXDS XXHSEDSERX SXSASRNHXG  180
SXXEQXRXGS RXPXXHXEDR AXHGHSADXS RKSGTXHXXX SSXGQAASSX EQARSSXGER  240
HGSRHQXQSA DSSXXSGXXH XQXSSAVXDS XXXGXSGSQA TXXEGHSEDS DTQSVSGXGX  300
XGXHQQSHXE SXRXXSGXXS XRSXSFLY                                    328

SEQ ID NO: 10            moltype = AA   length = 416
FEATURE                  Location/Qualifiers
source                   1..416
                         mol_type = protein
                         organism = Homo sapiens
SEQUENCE: 10
AGPHQQSHQE STRGRSAGRS GRSGSFLYQV STHEQSESAH GRTGTSTGGR QGSHHQQARD   60
SSRHSTSQEG QDTIHGHRGS SSGGRQGSHY EQLVDRSGHS GSHHSHTTSQ GRSDASHGHS  120
GSRSASRQTR NDEQSGDGSR HSGSRHHEAS SRADSSGHSQ VGQGQSEGPR TSRNWGSSFS  180
QDSDSQGHSE DSERWSGSAS RNHHGSAQEQ LRDGSRHPRS HQEDRAGHGH SADSSRQSGT  240
RHTQTSSGGQ AASSHEQARS SAGDRHGSHH QQSADSSRHS GIGHGQASSA VRDSGHRGYS  300
GSQASDNEGH SEDSDTQSVS AHGQAGSHQQ SHQESARGRS GETSGHSGSF LYQVSTHEQS  360
ESSHGWTGPS TRGRQGSRHE QAQDSSRHSA SQDGQDTIRG HPGSSRGGRQ GYHHEQ      416

SEQ ID NO: 11            moltype = AA   length = 4061
FEATURE                  Location/Qualifiers
source                   1..4061
                         mol_type = protein
                         organism = Homo sapiens
SEQUENCE: 11
MSTLLENIFA IINLFKQYSK KDKNTDTLSK KELKELLEKE FRQILKNPDD PDMVDVFMDH   60
LDIDHNKKID FTEFLLMVFK LAQAYYESTR KENLPISGHK HRKHSHHDKH EDNKQEENKE  120
NRKRPSSLER RNNRKGNKGR SKSPRETGGK RHESSSEKKE RKGYSPTHRE EEYGKNHHNS  180
SKKEKNKTEN TRLGDNRKRL SERLEEKEDN EEGVYDYENT GRMTQKWIQS GHIATYYTIQ  240
DEAYDTTDSL LEENKIYERS RSSDGKSSSQ VNRSRHENTS QVPLQESRTR KRRGSRVSQD  300
RDSEGHSEDS ERHSGSASRN HHGSAWEQSR DGSRHPRSHD EDRASHGHSA DSSRQSGTRH  360
AETSSRGQTA SSHEQARSSP GERHGSGHQQ SADSSRHSAT GRGQASSAVS DRGHRGSSGS  420
QASDSEGHSE NSDTQSVSGH GKAGLRQQSH QESTRGRSGE RSGRSGSSLY QVSTHEQPDS  480
AHGRTGTSTG GRQGSHHEQA RDSSRHSASQ EGQDTIRGHP GSSRGGRQGS HHEQSVNRSG  540
HSGSHHSHTT SQGRSDASHG QSGSRSASRQ TRNEEQSGDG TRHSGSRHHE ASSQADSSRH  600
SQVGQGQSSG PRTSRNQGSS VSQDSDSQGH SEDSERWSGS ASRNHHGSAQ EQSRDGSRHP  660
RSHHEDRAGH GHSADSSRKS GTRHTQNSSS GQAASSHEQA RSSAGERHGS RHQLQSADSS  720
RHSGTGHGQA SSAVRDSGHR GSSGSQATDS EGHSEDSDTQ SVSGHGQAGH HQQSHQESAR  780
DRSGERSRRS GSFLYQVSTH KQSESSHGWT GPSTGVRQGS HHEQARDNSR HSASQDGQDT  840
IRGHPGSSRR GRQGSHHEQS VDRSGHSGSH HSHTTSQGRS DASRGQSGSR SASRTTRNEE  900
QSRDGSRHSG SRHHEASSHA DISRHSQAGQ GQSEGSRTSR RQGSSVSQDS DSEGHSEDSE  960
RWSGSASRNH RGSAQEQSRH GSRHPRSHHE DRAGHGHSAD SSRQSGTPHA ETSSGGQAAS 1020
SHEQARSSPG ERHGSRHQQS ADSSRHSGIP RRQASSAVRD SGHWGSSGSQ ASDSEGHSEE 1080
SDTQSVSGHG QDGPHQQSHQ ESARDWSGGR SGRSGSFIYQ VSTHEQSESA HGRTRTSTGR 1140
RQGSHHEQAR DSSRHSASQE GQDTIRAHPG SRRGGRQGSH HEQSVDRSGH SGSHHSHTTS 1200
QGRSDASHGQ SGSRSASRQT RKDKQSGDGS RHSGSRHHEA ASWADSSRHS QVGQEQSSGS 1260
RTSRHQGSSV SQDSDSERHS DDSERLSGSA SRNHHGSSRE QSRDGSRHPG FHQEDRASHG 1320
HSADSSRQSG THHTESSSHG QAVSSHEQAR SSPGERHGSR HQQSADSSRH SGIGHRQASS 1380
AVRDSGHRGS SGSQVTNSEG HSEDSDTQSV SAHGQAGPHQ QSHKESARGQ SGESSGRSRS 1440
FLYQVSSHEQ SESTHGQTAP STGGRQGSRH EQARNSSRHS ASQDGQDTIR GHPGSSRGGR 1500
QGSYHEQSVD RSGHSGYHHS HTTPQGRSDA SHGQSGPRSA SRQTRNEEQS GDGSRHSGSR 1560
HHEPSTRAGS SRHSQVGQGE SAGSKTSRRQ GSSVSQDRDS EGHSEDSERR SESASRNHYG 1620
SAREQSRHGS RNPRSHQEDR ASHGHSAESS RQSGTRHAET SSGGQAASSQ EQARSSPGER 1680
HGSRHQQSAD SSTDSGTGRR QDSSVVGDSG NRGSSGSQAS DSEGHSEESD TQSVSAHGQA 1740
GPHQQSHQES TRGQSGERSG RSGSFLYQVS THEQSESAHG RTGPSTGGRQ RSRHEQARDS 1800
SRHSASQEGQ DTIRGHPGSS RGGRQGSHYE QSVDSSGHSG SHHSHTTSQE RSDVSRGQSG 1860
SRSVSRQTRN EKQSGDGSRH SGSRHHEASS RADSSRHSQV GQGQSSGPRT SRNQGSSVSQ 1920
DSDSQGHSED SERWSGSASR NHLGSAWEQS RDGSRHPGSH HEDRAGHGHS ADSSRQSGTR 1980
HTESSSRGQA ASSHEQARSS AGERHGSHHQ LQSADSSRHS GIGHGQASSA VRDSGHRGYS 2040
GSQASDSEGH SEDSDTQSVS AQGKAGPHQQ SHKESARGQS GESSGRSGSF LYQVSTHEQS 2100
ESTHGQSAPS TGGRQGSHYD QAQDSSRHSA SQEGQDTIRG HPGPSRGGRQ GSHQEQSVDR 2160
SGHSGSHHSH TTSQGRSDAS RGQSGSRSAS RKTYDKEQSG DGSRHSGSHH HEASSWADSS 2220
RHSLVGQGQS SGPRTSRPRG SSVSQDSDSE GHSEDSERRS GSASRNHHGS AQEQSRDGSR 2280
HPRSHHEDRA GHGHSAESSR QSGTHHAENS SGGQAASSHE QARSSAGERH GSHHQQSADS 2340
SRHSGIGHGQ ASSAVRDSGH RGSSGSQASD SEGHSEDSDT QSVSAHGQAG PHQQSHQEST 2400
```

-continued

```
RGRSAGRSGR SGSFLYQVST HEQSESAHGR TGTSTGGRQG SHHKQARDSS RHSTSQEGQD 2460
TIHGHPGSSS GGRQGSHYEQ LVDRSGHSGS HHSHTTSQGR SDASHGHSGS RSASRQTRND 2520
EQSGDGSRHS GSRHHEASSR ADSSGHSQVG QGQSEGPRTS RNWGSSFSQD SDSQGHSEDS 2580
ERWSGSASRN HHGSAQEQLR DGSRHPRSHQ EDRAGHGHSA DSSRQSGTRH TQTSSGGQAA 2640
SSHEQARSSA GERHGSHHQQ SADSSRHSGI GHGQASSAVR DSGHRGYSGS QASDNEGHSE 2700
DSDTQSVSAH GQAGSHQQSH QESARGRSGE TSGHSGSFLY QVSTHEQSES SHGWTGPSTR 2760
GRQGSRHEQA QDSSRHSASQ DGQDTIRGHP GSSRGGRQGY HHEHSVDSSG HSGSHHSHTT 2820
SQGRSDASRG QSGSRSASRT TRNEEQSGDG SRHSGSRHHE ASTHADISRH SQAVQGQSEG 2880
SRRSRRQGSS VSQDSDSEGH SEDSERWSGS ASRNHHGSAQ EQLRDGSRHP RSHQEDRAGH 2940
GHSADSSRQS GTRHTQTSSG GQAASSHEQA RSSAGERHGS HHQQSADSSR HSGIGHGQAS 3000
SAVRDSGHRG YSGSQASDNE GHSEDSDTQS VSAHGQAGSH QQSHQESARG RSGETSGHSG 3060
SFLYQVSTHE QSESSHGWTG PSTRGRQGSR HEQAQDSSRH SASQYGQDTI RGHPGSSRGG 3120
RQGYHHEHSV DSSGHSGSHH SHTTSQGRSD ASRGQSGSRS ASRTTRNEEQ SGDSSRHSVS 3180
RHHEASTHAD ISRHSQAVQG QSEGSRRSRR QGSSVSQDSD SEGHSEDSER WSGSASRNHR 3240
GSVQEQSRHG SRHPRSHHED RAGHGHSADR SRQSGTRHAE TSSGGQAASS HEQARSSPGE 3300
RHGSRHQQSA DSSRHSGIPR GQASSAVRDS RHWGSSGSQA SDSEGHSEES DTQSVSGHGQ 3360
AGPHQQSHQE SARDRSGGRS GRSGSFLYQV STHEQSESAH GRTRTSTGRR QGSHHEQARD 3420
SSRHSASQEG QDTIRGHPGS SRRGRQGSHY EQSVDRSGHS GSHHSHTTSQ GRSDASRGQS 3480
GSRSASRQTR NDEQSGDGSR HSWSHHHEAS TQADSSRHSQ SGQGQSAGPR TSRNQGSSVS 3540
QDSDSQGHSE DSERWSGSAS RNHRGSAQEQ SRDGSRHPTS HHEDRAGHGH SAESSRQSGT 3600
HHAENSSGGQ AASSHEQARS SAGERHGSHH QQSADSSRHS GIGHGQASSA VRDSGHRGSS 3660
GSQASDSEGH SEDSDTQSVS AHGQAGPHQQ SHQESTRGRS AGRSGRSGSF LYQVSTHEQS 3720
ESAHGRAGPS TGGRQGSRHE QARDSSRHSA SQEGQDTIRG HPGSRRGGRQ GSYHEQSVDR 3780
SGHSGSHHSH TTSQGRSDAS HGQSGSRSAS RETRNEEQSG DGSRHSGSRH HEASTQADSS 3840
RHSQSGQGES AGSRRSRRQG SSVSQDSDSE AYPEDSERRS ESASRNHHGS SREQSRDGSR 3900
HPGSSHRDTA SHVQSSPVQS DSSTAKEHGH FSSLSQDSAY HSGIQSRGSP HSSSSYHYQS 3960
EGTERQKGQS GLVWRHGSYG SADYDYGESG FRHSQHGSVS YNSNPVVFKE RSDICKASAF 4020
GKDHPRYYAT YINKDPGLCG HSSDISKQLG FSQSQRYYYY E 4061
```

```
SEQ ID NO: 12        moltype = AA  length = 4384
FEATURE              Location/Qualifiers
VARIANT              1045
                     note = MOD_RES - Any amino acid
VARIANT              1048
                     note = MOD_RES - Any amino acid
source               1..4384
                     mol_type = protein
                     organism = Mus musculus
SEQUENCE: 12
MSALLESITS MIEIFQQYST SDKEEETLSK EELKELLEGQ LQAVLKNPDD QDIAEVFMQM 60
LDVDHDDKLD FAEYLLLVLK LAKAYYEASK NESFQTHGSN GRSKTDYKGL EEEGEEGNKQ 120
NLRRRHGGTD GKRKSDRTRS PNGKRGKRQE SRCRSEGKDK HRREPEKHRH QQDSKRKQRH 180
GSGSTERKDN RNKKNRQSKE RNYDEIYDNG KYNEDWEASY NNCYYKTQNT TLDQREGNRR 240
PRADSQKEPQ SSHGQADNSD SEGGRQQSHS KPSPVRADQR RSRAGQAGSS KVSARSGSGG 300
RGQSPDGSGR SSNRRDRPRQ PSPSQSSDSQ VHSGVQVEGR RGQSSSANRR AGSSSGSGVQ 360
GASAGGLAAD ASRRSGARQG QASAQGRAGS QGQAQGRVGS SADRQGRRGV SESQASDSEG 420
HSDFSEGQAV GAHRQSGAGQ RHEQRSSRGQ HGSRYYYEQE HSEEEESDSQ HQHGHQHEQQ 480
GHQHQHEHEQ PESGHRQQQS SGRGHQGAHQ EQGRDSARSR GSNQGHSSSR HQADSPRVSA 540
RSGSGGRGQS PDASGRSSNR RDRPRQPSPS QSSDSQVHSG VQVEGRRGQS SSANRRAGSS 600
SGSGVQGASA GGLAADASRR SGALQGQASA QGRAGSQGQA QGRVGSSADR QGRRGVSESQ 660
ASDSEGHSDF SEGQAVGAHR QSGAGQRHEQ RSSRGQHGSG YYYEQEHSEE ESDSQHQHGH 720
QHEQQRGHQH QHQHQHEHEQ PESGHRQQQS SGRGHQGAHQ EQGRDSARSR GSNQGHSSSR 780
HQADSPRVSA RSGSGGRGQS PDASGRSSNR RDRPRQPSPS QSSDSQVHSG VQVEGRRGQS 840
SSANRRAGSS SGSGVQGTSA GGLAADASRR SGARQGQASA QGRAGSQGQA QGRVGSSADR 900
QGRRGVSESQ ASDSEGHSDF SEGQAVGAHR QSGAGQRHEQ RSSRGQHGSG YYYEQEHSEE 960
ESDSQHQHGH QHEQQRGHQH QHQHQHEHEQ PESGHRQQQS SGRGNQGAHQ KQGRDSARSR 1020
GSNQGHSSSR HQADSPRVSA RSGSXGRXQS PDASGRNSTK RDRPRQPSPS QSSDSHVHSG 1080
KAGSISGSGV QGASAGGLAA DASRRSGARQ GQASAQGRAG SQGQAQGRVG SSADRQGRRG 1140
VSESQASDSE GHSDFSEGQA VGAHRQSGAG QRHEQRSSRG QHGSRYYYEQ EHSEEESDSQ 1200
HQHGHQHEQQ RGHQHQHEHE QPESGHRQQQ SSGRGHQGAH QEQGRDSARS RGSNQGHSSS 1260
RHQADSPRVS ARSGSGGRGQ SPDASGRSSN RRDRPRQPSP SQSSDSQVHS GVQVEGRRGQ 1320
SSSANRRAGS SSGSGVQGAS AGGLAADASR RSGARQGQAS AQGRAGSQGQ AQGRIGSSAD 1380
RQGRRGVSES QASDSEGHSD FSEGQAVGAH RQSEAGQRHE QRSSRGQHGS GYYYEQEHSE 1440
EESDSQHQHG HQHEQQRGTQ HQHEHQQPES GHRQQQSSGR GHQGTHQEQG RDSARSRGSN 1500
QGHSSSRHQA DSPRVSARSG SGGRGQSPDA SGRSSNRRDR PRQPSPSQSS DSQVHSGVQV 1560
EGRRRQSSSA NRRAGSSSGS GVQGASAGGL AADASRRSGA RQGQASAQGR AGSQGQAQGR 1620
VGSSADRQGR RGVSESQASD SEGHSDFSEG QAVGAHRQSG AGQRHEQRSS RGQHGSGFYP 1680
VYYYEQEHS EEEESDSQHQH GHQHEQQRGH QHQHQHEHEQ PESGHRQQQS SGRGHQGAHQ 1740
EQGRDSARSR GSNQGHSSSR HQADSPRVSA RSGSGGRGQS PDASGRSSNR RDRPRQPSPS 1800
QSSDSQVHSG VQVEGRRGQS SSANRRAGSS SGSGVQGASA GGLAADASRR SGALQGQASA 1860
QGRAGSQGQA QGRVGSSADR QGRRGVSGSQ ASDSEGHSDF SEGQAVGAHR QSGAGQRHEQ 1920
RSSRGQHGSG YYYEQEHSEE ESDSQHQHGH QHEQQRGHQH QHQHQHEHEQ PESGHRQQQF 1980
SGRGHQGAHQ EQGRDSARSR GSNQGHSSSR HQADSPRVSA RSGSGGRGQS PDASGRSSNR 2040
RDRPRQPSPS QSSDSQVHSG VQVEGRRGQS SSANRRAGSS SGSGVQGASA GGLAADASRR 2100
SGARQGQASA QGRAGSQGQA QGRVGSSADR QGRRGVSESQ ASDSEGHSDF SEGQAVGAHR 2160
QSGAGQRHEQ RSSRGQHGSG FYPVYYYEQ EHSEEESDSQ HQHGHQHEQQ RGHQHQHQHQ 2220
HEHEQPESGH RQQQSSGRGH QGAHQEQGRD SARSRGSNQG HSSSRHQADS PRVSARSGSG 2280
GRGQSPDASG RSSNRRDRPR QPSPSQSSDS QVHSGVQVEG RRGQSSSANR RAGSSSGSGV 2340
QGASAGGLAA DASRRSGARQ GQASAQGRAG SQGQAQGRVG SSADRQGRRG VSESQASDSE 2400
```

```
GHSDFSEGQA VGAHRQSGAG QRHEQRSSRG QHGSGYYYEQ EHSEEESDSQ HQHGHQHEQQ 2460
RGHQHQHQHQ HEHEQPESGH RQQQSSGRGH QGAHQEQGRD SARSRGSNQG HSSSRHQADS 2520
PRVSARSGSG GRGQSPDASG RSSNRRDRPR QPSPSQSSDS QVHSGVQVEG RRGQSSSANR 2580
RAGSSSGSGV QGASAGGLAA DASRRSGARQ GQASAQGRAG SQGQAQGRVG SSADRQGRRG 2640
VSESQASDSE GHSDFSEGQA VGAHRQSGAG QRHEQRSSRS QHGSGYYYEQ EHSEEESDSQ 2700
HQHSHQHEQQ RGHQHQHQHQ HEHEQPESGH RQQQSSGRGN QGAHQEQGRD SARSRGSNQG 2760
HSSSRHQADS PRVSARSGSG GRGQSPDASG RSSNRRDRPR QPSPSQSSDS HVHSGVQVEG 2820
RRGQSSSANR RAGSSSGSGV QGASAGGLAA DASRRSGARQ GQASAQGRAG SQGQAQGRVG 2880
SSADRQGRRG VSESQASDSE GHSDFSEGQA VGAHRQSGAG QRHEQRSSRG QHGSGFYPVY 2940
YYYEQEHSEE ESDSQHQHGH QHEQQRGHQH QHQHQHEHEQ PESGHRQQQS SGRGHQGAHQ 3000
EQGRDSARSR GSNQGHSSSR HQADSPRVSA RSGSGGRGQS PDASGRSSNR RDRSRQPSPS 3060
QSSDSQVHSG VQVEGRRGQS SSANRRAGSS SGSGVQGASA GGLAADASRR SGARQGQASA 3120
QGRAGSQGQA QGRVGSSADR QGRRGVSESQ ASDSEGHSDF SEGQAVGAHR QSGAGQRHEQ 3180
RSSRGQHGSG FYPVYYYEQ EHSEEESDSQ HQHGHQHEQQ RGHQHQHQHE HEQPESGHRQ 3240
QQSSGRGHQG AHQEQGRDSA RSRGSNQGHS SSRHQADSPR VSARSGSGGR GQSPDASGRS 3300
SNRRDRPRQP SPSQSSDSQV HSGVQVEGRR GQSSSANRRA GSSSGSGVQG ASAGGLAADA 3360
SRRSGALQGQ ASAQGRAGSQ GQAQGRVGSS ADRQGRRGVS ESQASDSEGH SDFSEGQAVG 3420
AHRQSGAGQR HEQRSSRGQH GSGYYYEQEH SEEESDSQHQ HGHQHEQQRG HQHQHQHQHE 3480
HEQPESGHRQ QQSSGRGHQG AHQEQGRDSA RSRGSNQGHS SSRHQADSPR VSARSGSGGR 3540
GQSPDASGRS SNRRDRPRQP SPSQSSDSQV HSGVQVEGRR GQSSSANRRA GSSSGSGVQG 3600
ASAGGLAADA SRRSGARQGQ ASAQGRAGSQ GQAQGRVGSS ADRQGRRGVS GSQASDSEGH 3660
SDFSEGQAVG AHRQSGAGQR HEQRSSRGQH GSGYYYEQEH SEEESDSQHQ HGHQHEQQRG 3720
HQHQHQHQHE HEQPESGHRQ QQFSGRGHQG AHQEQGRDSA RSRGSNQGHS SSRHQADSPR 3780
VSARSGSGGR GQSPDASGRS SNRRDRPRQP SPSQSSDSQV HSGVQVEGRR GQSSSANRRA 3840
GSSSSSGVQG ASAGGLAADA SRRSGARQGQ ASAQGRAGSQ GQAQGRVGSS ADRQGRRGVS 3900
ESQASDSEGH SDFSEGQAVG AHRQSGAGQR HEQRSSRGQH GSGFYPVYYY EQEHSEEES 3960
DSQHQHGHQH EQQRGHQHQH QHQHEHEQPE SGHRQQQFSG RGHQGAHQEQ GRDSARSRGS 4020
NQGHSSSRHQ ADSPRVSARS GSGGRGQSPD ASGRSSNRRD RPRQPSPSQS SDSQVHSGVQ 4080
VEGRRGQSSS ANRRAGSSSG SGVQGASAGG LAADASRRSG ARQGQASAQG RAGSQGQAQG 4140
RVGSSADRQG RRGVSESQAS DSEGHSDFSE GQAVGAHRQS GAGQRHEQRS SRGQHGSGYY 4200
YEQEHSEEES DSQHQQGHQH EQQRGHQHQH QHQHEHEQPE SGHRQQQSSG RGHQGAHQEQ 4260
GRDSARSRGS NQGHSSSRHQ ADSPRVSARS GSGGRGQSPD GSGRSSNRRD RPRQPSASQS 4320
SDSQVHSGVQ VEAQRGQSSS ANRRAGSSSG SGVQSAAASG QGGYESIFTA KHLDFNQSHS 4380
YYYY                                                          4384
```

```
SEQ ID NO: 13              moltype = AA  length = 554
FEATURE                    Location/Qualifiers
source                     1..554
                           mol_type = protein
                           organism = Mus musculus
SEQUENCE: 13
MSALLESITS MIEIFQQYST SDKEEETLSK EELKELLEGQ LQAVLKNPDD QDIAEVFMQM 60
LDVDHDDKLD FAEYLLLVLK LAKAYYEASK NESFQTHGSN GRSKTDYKGL EEEGEEGNEQ 120
NLRRRHGGTD GKRKSDRTRS PNGKRGKRQE SRCRSEGKDK HRREPEKHRH QQDSKRKQRH 180
GSGSTERKDN RNKKNRQSKE RNYDEIYDNG KYNEDWEASY NNCYYKTQNT TLDQREGNRR 240
PRADSQKEPQ SFHGQADNSD SEGGRQQSHS KPSPVRADQR RSRAGQAGSS KVSARSGSGG 300
RGQSPDGSGR SSNRRDRPRQ PSPSQSSDSQ VHSGVQVEGR AGSSSGSGVQ 360
GASAGGLAAD ASRRTGALQG QASAQGRAGS QGQAQGRVGS SADRQGRRGV SESQASDSEG 420
QSDFSEGQAV GAHRQSGAGQ RHEQRSSRGQ YGSGFYPVYY YYEQEHSEEE SDSQHGHQHE 480
QQRGHQHQHQ HEHEQPESGH RQQQSSGRGH QGAHQEQGRD SARSRGSNQG HSSSRHQADS 540
PRVSVRSGSG GRGQ                                               554
```

```
SEQ ID NO: 14              moltype = AA  length = 336
FEATURE                    Location/Qualifiers
source                     1..336
                           mol_type = protein
                           organism = Mus musculus
SEQUENCE: 14
PDGSGRSSNR RDRPRQLSPS QSSDSQVHSG VQVEGRRGHS SSANRRAGSS SGSGVQGASA 60
GGLAADASRR SGARQGQASA QGRAGSQGQA QGRVSSSADR QGRRGVSESR ASDSEGHSDF 120
SEGQAVGAHR QSGAGQRHEQ RSSRGQHGSG YYYEQEHSEE ESDSQHQHGH QHEQQRGHQH 180
QHQHQHEHEQ PESGHRQQQS SGRGHQGAHQ EQGRDSARPR GSNQGHSSSR HQADSPRVSA 240
RSGSGGRGQS PDASGRSSNR RDRPQPSPS QSSDSQVHSG VQVEAQRGQS SSANRRAGSS 300
SGSGVQGAAA SGQGGYESIF TAKHLDFNQS HSYYYY                       336
```

```
SEQ ID NO: 15              moltype = AA  length = 250
FEATURE                    Location/Qualifiers
source                     1..250
                           mol_type = protein
                           organism = Mus musculus
SEQUENCE: 15
GGLAADASRR SGALQGQASA QGRAGSQGQA QGRVGSSADR QGRRGVSESQ ASDSEGHSDF 60
SEGQAVGAHR QSGAGQRHEQ RSSRGQHGSG YYYEQEHSEE ESDSQHQHGH QHEQQRGHQH 120
QHQHQHEHEQ PESGHRQQQS SGRGHQGAHQ EQGRDSARSR GSNQGHSSSR HQADSPRVSA 180
RSGSGGRGQS PDASGRSSNR RDRPRQPSPS QSSDSQVHSG VQVEGRRGQS SSANRRAGSS 240
SSSGVQGASA                                                   250
```

```
SEQ ID NO: 16              moltype = AA  length = 2642
FEATURE                    Location/Qualifiers
```

-continued

```
source                  1..2642
                        mol_type = protein
                        organism = Mus musculus
SEQUENCE: 16
MSTNSPSPAT GSSSSADSPR VSARSGSGGR GQSPDASGRS SNRRDRPRQP SPSQSSDSQV  60
HSGVQVEGRR GQSSSANRRA GSSSGSGVQG ASAGGLAADA SRRSGARQGQ ASAQGRAGSQ  120
GQAQGRVGSS ADRQGRRGVS ESQASDSEGH SDFSEGQAVG AHRQSGAGQR HEQRSSRGQH  180
GSGFYPVYYY YEQEHSEEES DSQHQHGHQH EQQRGHQHQH QHQHEHEQPE SGHRQQQSSG  240
RGHQGAHQEQ GRDSARSRGS NQGHSSSRHQ ADSPRVSARS GSGGRGQSPD ASGRSSNRRD  300
RPRQPSPSQS SDSQVHSGVQ VEGRRGQSSS ANRRAGSSSG SGVQGASAGG LAADASRRSG  360
ARQGQASAQG RAGSQGQAQG RVGSSADRQG RRGVSESQAS DSEGHSDFSE GQAVGAHRQS  420
GAGQRHEQRS SRGQHGSGYY YEQEHSEEES DSQHQHSHQH EQQRGHQHQH QHQHEHEQPE  480
SGHRQQQFSG RGHQGAHQEQ GRDSARSRGS NQGHSSSRHQ ADSPRVSARS GSGGRGQSPD  540
ASGRSSNRRD RPRQPSPSQS SDSQVHSGVQ VEGRRGQSSS ANRRAGSSSG SGVQGASAGG  600
LAADASRRSG ARQGQASAQG RAGSQGQAQG RVGSSADRQG RRGVSESQAS DSEGHSDFSE  660
GQAVGAHRQS GAGQRHEQRS SRGQHGSGFY PVYYYYEQEH SEEESDSQHQ HGHQHEQQRG  720
HQHQHQHQHE HEQPESGHRQ QQSSGRGHQG AHQEQGRDSA RSRGSNQGHS SSRHQADSPR  780
VSARSGSGGR GQSPDASGRS SNRRDRPRQP SPSQSSDSQV HSGVQVEGRR GQSSSANRRA  840
GSSSGSGVQG ASAGGLAADA SRRSGARQGQ ASAQGRAGSQ GQAQGRVGSS ADRQGRRGVS  900
ESQASDSEGH SDFSEGQAVG AHRQSGAGQR HEQRSSRSQH GSGYYYEQEH SEEESDSQHQ  960
HSHQHEQQRG HQHQHQHQHE HEQPESGHRQ QQSSGRGNQG AHQEQGRDSA RSRGSNQGHS  1020
SSRHQADSPR VSARSGSGGR GQSPDASGRS SNRRDRPRQP SPSQSSDSHV HSGVQVEGRR  1080
GQSSSANRRA GSSSGSGVQG ASAGGLAADA SRRSGARQGQ ASAQGRAGSQ GQAQGRVGSS  1140
ADRQGRRGVS ESQASDSEGH SDFSEGQAVG AHRQSGAGQR HEQRSSRGQH GSGFYPVYYY  1200
YEQEHSEEES DSQHQHGHQH EQQRGHQHQH QHQHEHEQPE SGHRQQQSSG RGHQGAHQEQ  1260
GRDSARSRGS NQGHSSSRHQ ADSPRVSARS GSGGRGQSPD ASGRSSNRRD RSRQPSPSQS  1320
SDSQVHSGVQ VEGRRGQSSS ANRRAGSSSG SGVQGASAGG LAADASRRSG ARQGQASAQG  1380
RAGSQGQAQG RVGSSADRQG RRGVSESQAS DSEGHSDFSE GQAVGAHRQS GAGQRHEQRS  1440
SRGQHGSGFY PVYYYYEQEH SEEESDSQHQ HGHQHEQQRG HQHQHQHEHE QPESGHRQQQ  1500
SSGRGHQGAH QEQGRDSARS RGSNQGHSSS RHQADSPRVS ARSGSGGRGQ SPDASGRSSN  1560
RRDRPRQPSP SQSSDSQVHS GVQVEGRRGQ SSSANRRAGS SSGSGVQGAS AGGLAADASR  1620
RSGALQGQAS AQGRAGSQGQ AQGRVGSSAD RQGRRGVSES QASDSEGHSD FSEGQAVGAH  1680
RQSGAGQRHE QRSSRGQHGS GYYYEQEHSE EESDSQHQHG HQHEQQRGHQ HQHQHQHEHE  1740
QPESGHRQQQ SSGRGHQGAH QEQGRDSARS RGSNQGHSSS RHQADSPRVS ARSGSGGRGQ  1800
SPDASGRSSN RRDRPRQPSP SQSSDSQVHS GVQVEGRRGQ SSSANRRAGS SSGSGVQGAS  1860
AGGLAADASR RSGARQGQAS AQGRAGSQGQ AQGRVGSSAD RQGRRGVSGS QASDSEGHSD  1920
FSEGQAVGAH RQSGAGQRHE QRSSRGQHGS GYYYEQEHSE EESDSQHQHG HQHEQQRGHQ  1980
HQHQHQHEHE QPESGHRQQQ FSGRGHQGAH QEQGRDSARS RGSNQGHSSS RHQADSPRVS  2040
ARSGSGGRGQ SPDASGRSSN RRDRPRQPSP SQSSDSQVHS GVQVEGRRGQ SSSANRRAGS  2100
SSSSGVQGAS AGGLAADASR RSGARQGQAS AQGRAGSQGQ AQGRVGSSAD RQGRRGVSES  2160
QASDSEGHSD FSEGQAVGAH RQSGAGQRHE QRSSRGQHGS GFYPVYYYYE QEHSEEESDS  2220
QHQHGHQHEQ QRGHQHQHQH QHEHEQPESG HRQQQFSGRG HQGAHQEQGR DSARSRGSNQ  2280
GHSSSRHQAD SPRVSARSGS GGRGQSPDAS GRSSNRRDRP RQPSPSQSSD SQVHSGVQVE  2340
GRRGQSSSAN RRAGSSSGSG VQGASAGGLA ADASRRSGAR QGQASAQGRA GSQGQAQGRV  2400
GSSADRQGRR GVSESQASDS EGHSDFSEGQ AVGAHRQSGA GQRHEQRSSR GQHGSGYYYE  2460
QEHSEEESDS QHQQGHQHEQ QRGHQHQHQH QHEHEQPESG HRQQQSSGRG HQGAHQEQGR  2520
DSARSRGSNQ GHSSSRHQAD SPRVSARSGS GGRGQSPDGS GRSSNRRDRP RQPSASQSSD  2580
SQVHSGVQVE AQRGQSSSAN RRAGSSSGSG VQSAAASGQG GYESIFTAKH LDFNQSHSYY  2640
YY                                                                 2642

SEQ ID NO: 17           moltype = AA  length = 336
FEATURE                 Location/Qualifiers
source                  1..336
                        mol_type = protein
                        organism = Mus musculus
SEQUENCE: 17
PDGSGRSSNR RDRPRQLSPS QSSDSQVHSG VQVEGRRGHS SSANRRAGSS SGSGVQGASA  60
GGLAADASRR SGARQGQASA QGRAGSQGQA QGRVSSSADR QGRRGVSESR ASDSEGHSDF  120
SEGQAVGAHR QSGAGQRHEQ RSSRGQHGSG YYYEQEHSEE ESDSQHQHGH QHEQQRGHQH  180
QHQHEHEQ PESGHRQQQS SGRGHQGAHQ EQGRDSARPR GSNQGHSSSR HQADSPRVSA  240
RSGSGGRGQS PDASGRSSNR RDRPQPSPS QSSDSQVHSG VQVEAQRGQS SSANRRAGSS  300
SGSGVQGAAA SGQGGYESIF TAKHLDFNQS HSYYYY                            336

SEQ ID NO: 18           moltype = AA  length = 357
FEATURE                 Location/Qualifiers
source                  1..357
                        mol_type = protein
                        organism = Mus musculus
SEQUENCE: 18
MSALLESITS MIEIFQQYST SDKEEETLSK EELKELLEGQ LQAVLKNPDD QDIAEVFMQM  60
LDVDHDDKLD FAEYLLLVLK LAKAYYEASK NESFQTHGSN GRSKTDYKGL EEEGEEGNKQ  120
NLRRRHGGTD GKRKSDRTRS PNGKRGKRQE SRCRSEGKDK HRREPEKHRH QQDSKRKQRH  180
GGGSTERKDN RNKKNRQSKE RNYDEIYDNG KYNEDWEASY NNCYYKTQNT TLDQREGNRR  240
PRADSQKEPQ SSHGQADNSD SEGGRQQSHS KPSPVRADQR RSRAGQAGSS KVSARSGSGG  300
RGQSPDGSGR SSNRRDRPRQ PSPSQSSDSQ VHSGVQVEGR RGQSSSANRR AGSSSGS     357

SEQ ID NO: 19           moltype = AA  length = 366
FEATURE                 Location/Qualifiers
source                  1..366
```

```
                         mol_type = protein
                         organism = Rattus norvegicus
SEQUENCE: 19
MSTLLESITS MIDIFQQYSN NDKEEETLSK EELKELLEGE LQAVLKNPND QDIAEVFMQM    60
LDVDHDDKID FTEYLLMVLK LAQAYYETSK KRRSQTKESG KRNEHDYKGY EERREKVQRR   120
HRRRNSGTDG KQENERSKSP RGRGNKRRGS STISEESDTN RNSDTENKRH HHGSNRRQRR   180
GSNSSDRKET RSKKHREVKE RNAGIYNDGK DGQDWEVNYE NCYYKTEESN REQREGRNHK   240
TKESHSESEA SGGQAGRRGT AATRHTSRPE QSPDTAGRTG SSRGQQSAQR HADSTPGSTR   300
TGSRGRGESP AGQQSPDRAR HIESRRGRTR EASASQSSDS EGHSGAHAGI GQGQTSTTHR   360
RAGSSS                                                             366

SEQ ID NO: 20           moltype = AA   length = 3088
FEATURE                 Location/Qualifiers
source                  1..3088
                        mol_type = protein
                        organism = Pan troglodytes
SEQUENCE: 20
MSTLLENIFA IINLFKQYSK KDKNTDTLSK KELKELLEKE FRQILKNPDD PDMVDVFMDH    60
LDIDHNKKID FTEFLLMVFK LAQAYYESTR KENLPISGHK HRKHSHHDKH EDNKQEENKE   120
NRKRPSSLER RNNRKGNKGR SKSPRETGGK RHESSSEKKE RKGYSPTHRE EEYGKNHHNS   180
SKKQKNKTEN TRLEDNRKRL SERLEEKEDN EEGGYDYENT GRMTQKWIQS GHIATYYTIQ   240
DEAYDTTDNL LEENKIYERS RSSDDKSSSQ VNRSRHENTS QVPLQESRTR KRRGSRVSQD   300
RDSEGHSEDS ERHSGSASRN HPGSARQQSR DGSRHPRSHD EDRASHGHSA DSSRQSGTRH   360
AETSSRGQTA SSHEQARSSP GERHGSRHQQ SADSSRHSAT GRGQASSAVS DRGPRGSSGS   420
QASDSEGHSE NSDTQSVSGH GKAGPRQQSH QESARGRSGE RSGHSGSFLY QVSTHEQSDS   480
AHGRTGTSTG GRQGSHHEQA RDSSRHSASQ EGQDTIRGHP GSSRGGRQGS HHEQLVNRSG   540
HSGSHHSHTT SQGRSDASHG QSGSRSASRQ TRNEEQSGDG SRHSGSRHHE ASSQADSSRH   600
SQVGQGQSSG PRTSSHQGSS VSQDSDSEGH SEDSERWSGS ASRNHHGSAR EQSRDGSRHP   660
RSHHEDRAGH GHSADSSRQS GTRHTESSSR GQAVSSHEQA RSSPGERHGS RHQQSADSSR   720
HSGIGHGQAS SAVRDSGHRG SSGSQAIDSE GHSEDSDTQS VSSHGQAGPH QQSHKESARG   780
QSGESSGRSG SFLYQVSSHE QSESTYGQTA PSTGGRQGSR HEQARNSSRH SASQDGQDTI   840
RGHPGSSRGG RQGSYHEQSV DRSGHSGYHH SHTTPQGRSD ASHGQSGPRS ASRQTRNEEQ   900
SGDGSRHSGS RHHEPSTRAS SSRHSQVGQG ESAVSKTSRR QGSSVSQDRD SEGHSEDSER   960
QSESASRNHY GSAREQSRHG SRNPRSHQED RASHGHSAES SQSGTHHAE TSSHGQAASS  1020
QEQARSSRGE RHGSRHQQSA DSSTDSGTGG RQASSVVGDS GNRGSSGSQA SDSEGHSEDS  1080
DTQSVSAHGQ AGPRQQSHQE STRGQSGERS GRSGSFLYQV STHEQSESAH GRTGPSTGGR  1140
QRSRHEQARD SSRHSASQES QDIIHAHPGS SRGGRQGSHY EQSVDRSGHS GSHHSHTTSQ  1200
ERSNASHGQS GSRSASRQTR NEEQSGDGSR HSGSRHHEAS SRADSSRHSQ VGQGQSSGPR  1260
TSRNQGSSVS QDSDSQGHSE DSERWSGSAS RNHHGSAWEQ SRDGSRHPGS HQEDRAGHGH  1320
SADSSRQSGT HHTESSSRGQ AASSHEHARS SAGERHGSHH QQSADSSRHS GIGHGQASSA  1380
VRDSGHRGSS GSQASDSEGH SEDSDTQSLS AHGQAGPHQQ SHQESTRGRS AERSGRSGSF  1440
LYQVSTHEQS ESAHGRTGTS TGGRKRSLHE QARDSSRHSV SQEGQDTIHG HAGSSSGGRQ  1500
GSHYEQLVDR SGHSGSHHSH TTSQGRSDAY HGQSGSRSAS RQTHNDEQSG DGFRHSGSHH  1560
HEASSRADSS RHSQVGQGQS EGPRTSRHRE SSVSQDSDSE GHSEDSERWS GSASRNHHGS  1620
AREQSRDGSR HPRSHHEDRA GHGHSADSSR QSGTRHTQTS SGGQAASSHE QGRSSAGERH  1680
GSRHQQSADS SRHSGIGHGQ ASSAVRDSGH RGYSGSQASD SEGHSEDSDT QSVSAHGQAG  1740
SHQQSENQESA RGRSGERSGR SGSFLYQVST HEQSESHGW TGPSTRGRQG SRHEQAQDSS  1800
RHSASQEGQD TIRGHPGPSR GGRQGYHHEQ SVDSSGHSGS HHSHITSQGS SHASHGQSGS  1860
RSASRTTRND EQSVDGSRHS GSRHHEASTH ADISRHSQAG QGQSEGSRTS RRQGSSVSQD  1920
SDSEGHSEDS ERWSGSASRN HRGSAQEQSR DGSRHPRSHH EDRAGHGHSA DSSRQSGTHH  1980
AETSSGQAA SSREQARSSP GERHGSRHQQ SADSSRHSGI RRGQASSAVR DSGHWGSSGS  2040
QASDSEGHSE ESDTQSVSGH GQDGPHQQSH QESARDRSGG RSGRSGSFLY QVSTHEQSES  2100
THGQTGTSTG GRQGSHHEQA RDSSRHSASQ EGQDTIHAHP GSSRGGRQGS HHEQSVDTSG  2160
HSGSHHSHTT SQGRSDASHG QSGSRSASRQ TRNDEQSGDG SRHSGSHHHE AFTQADSSRH  2220
SQSGQGESAG SRRSRRQGSS VSQDSDSQGH SEDSERWSGS ASRNQHGSAR EQSRDGSRHP  2280
GSHQEDRAGH GHSADSSRQS GTRHTESSSR GQAASSHEQA RSSAGERHGS RHQLQSADSS  2340
RHSGIGHGQA SSAVRDSGHR GSSGSQAIDS EGHSEDSDTQ SVSAQGQAGP HQRSHKESAR  2400
GQSGESSGRS GSFLYQVSTH EQPESTHGQS APSTGGRQGS HHDQAQDSSR HSASQEGQDT  2460
IRGHPGPSRG GRQGSHHKQS VDRSGHSGSH HSHTTSQGRS DASHGQSGSR SASRQTHDKE  2520
QSGDGSRHSG SRHHEASSWA DSSRHSQAGQ GQSEGSRTSR RQGSSFSQDS DSEGHSEDSE  2580
RRSGSASRNH RGSAQEQSRD GSRHPRSHHE DRAGHGHSAD SSRQSGTHHA QNSSGGQAAS  2640
FHEQARSSAG ERHGSHHQQS ADSSRHSGIG HGQASSAVRD SGHRGSSGSQ ASDSEGHSED  2700
SDTQSVSAHG QAGPHQQSHQ ESTRGRSAER SGRSGSFLYQ VSTHEQSESA HGRTGPSTGG  2760
RQGSRHEQAR DSSRHSASQE GQDTIHGHPG SRRGGRQGSY HEQSVDRSGH SGSHHSHTTS  2820
QGRSDASHGQ SGSRSASRQT RNEQQSGDGS RHSGSSHHEA STQADSSRHS QSGQGESAGS  2880
RRSRRQGSSV SQDSDSEAYP EDSERRSESA SRNHGSSRE QSRDGSRHPG SSHRDTTRHV  2940
QSSPVQSDSS TAKEHGHFSS LSQDSAYRSG IQSRGSPHSS SSYHYQSEGT ERQKGQSGLV  3000
WRHGSYGSAD YDYGESGFRH SQHGSVSYNS NPVVFKERSD ICKASAFGKD HPRYYATYIN  3060
KDPGLCGHSS DISKQLGFSQ SQRYYYYE                                    3088

SEQ ID NO: 21           moltype = AA   length = 2764
FEATURE                 Location/Qualifiers
source                  1..2764
                        mol_type = protein
                        organism = Pan troglodytes
SEQUENCE: 21
MSTLLENIFA IINLFKQYSK KDKNTDTLSK KELKELLEKE FRQILKNPDD PDMVDVFMDH    60
LDIDHNKKID FTEFLLMVFK LAQAYYESTR KENLPISGHK HRKHSHHDKH EDNKQEENKE   120
NRKRPSSLER RNNRKGNKGR SKSPRETGGK RHESSSEKKE RKGYSPTHRE EEYGKNHHNS   180
```

-continued

```
SKKQKNKTEN TRLEDNRKRL SERLEEKEDN EEGGYDYENT GRMTQKWIQS GHIATYYTIQ  240
DEAYDTTDNL LEENKIYERS RSSDDKSSSQ VNRSRHENTS QVPLQESRTR KRRGSRVSQD  300
RDSEGHSEDS ERHSGSASRN HPGSARQQSR DGSRHPRSHD EDRASHGHSA DSSRQSGTRH  360
AETSSRGQTA SSHEQARSSP GERHGSRHQQ SADSSRHSAT GRGQASSAVS DRGPRGSSGS  420
QASDSEGHSE NSDTQSVSGH GKAGPRQQSH QESARGRSGE RSGHSGSFLY QVSTHEQSRS  480
AHGRTGTSTG GRQGSHHEQA RDSSRHSASQ EGQDTIRGHP GSSRGGRQGS HHEQLVNRSG  540
HSGSHHSHTT SQGRSDASHG QSGSRSASRQ TRNEEQSGDG SRHSGSRHHE ASSQADSSRH  600
SQVGQGQSSG PRTSSHQGSS VSQDSDSEGH SEDSERWSGS ASRNHHGSAR EQSRDGSRHP  660
RSHHEDRAGH GHSADSSRQS GTRHTESSSR GQAVSSHEQA RSSPGERHGS RHQQSADSSR  720
HSGIGHGQAS SAVRDSGHRG SSGSQAIDSE GHSEDSDTQS VSSHGQAGPH QQSHKESARG  780
QSGESSGRSG SFLYQVSSHE QSESTYGQTA PSTGGRQGSR HEQARNSSRH SASQDGQDTI  840
RGHPGSSRGG RQGSYHEQSV DRSGHSGYHH SHTTPQGRSN ASHGQSGSRS ASRQTRNEEQ  900
SGDGSRHSGS RHHEASSRAD SSRHSQVGQG QSSGPRTSRN QGSSVSQDSD SQGHSEDSER  960
WSGSASRNHH GSAWEQSRDG SRHPGSHQED RAGHGHSADS SRQSGTHHTE SSSRGQAASS 1020
HEHARSSAGE RHGSHHQQSA DSSRHSGIGH GQASSAVRDS GHRGSSGSQA SDSEGHSEDS 1080
DTQSLSAHGQ AGPHQQSHQE STRGRSAERS GRSGSFLYQV STHEQSESAH GRTGTSTGGR 1140
KRSLHEQARD SSRHSVSQEG QDTIHGHAGS SSGGRQGSHY EQLVDRSGHS GSHHSHTTSQ 1200
GRSDAYHGQS GSRSASRQTH NDEQSGDGFR HSGSHHHEAS SRADSSRHSQ VGQGQSEGPR 1260
TSRHRESSVS QDSDSEGHSE DSERWSGSAS RNHHGSAREQ SRDGSRHPRS HHEDRAGHGH 1320
SADSSRQSGT RHTQTSSGGQ AASSHEQGRS SAGERHGSRH QQSADSSRHS GIGHGQASSA 1380
VRDSGHRGYS GSQASDSEGH SEDSDTQSVS AHGQAGSHQQ SHQESARGRS GERSGRSGSF 1440
LYQVSTHEQS ESSHGWTGPS TRGRQGSRHE QAQDSSRHSA SEGQDTIRG HPGPSRGGRQ 1500
GYHHEQSVDS SGHSGSHHSH ITSQGSSHAS HGQSGSRSAS RTTRNDEQSV DGSRHSGSRH 1560
HEASTHADIS RHSQAGQGQS EGSRTSRRQG SSVSQDSDSE GHSEDSERWS GSASRNHRGS 1620
AQEQSRDGSR HPRSHHEDRA GHGHSADSSR QSGTHHAETS SGGQAASSRE QARSSPGERH 1680
GSRHQQSADS SRHSGIRRGQ ASSAVRDSGH WGSSGSQASD SEGHSEESDT QSVSGHGQDG 1740
PHQQSHQESA RDRSGGRSGR SGSFLYQVST HEQSESTHGQ TGTSTGGRQG SHHEQARDSS 1800
RHSASQEGQD TIHAHPGSSR GGRQGSHHEQ SVDTSGHSGS HHSHTTSQGR SDASHGQSGS 1860
RSASRQTRND EQSGDGSRHS GSHHHEAFTQ ADSSRHSQSG QGESAGSRRS RRQGSSVSQD 1920
SDSQGHSEDS ERWSGSASRN QHGSAREQSR DGSRHPGSHQ EDRAGHGHSA DSSRQSGTRH 1980
TESSSRGQAA SSHEQARSSA GERHGSRHQL QSADSSRHSG IGHGQASSAV RDSGHRGSSG 2040
SQAIDSEGHS EDSDTQSVSA QGQAGPHQRS HKESARGQSG ESSGRSGSFL YQVSTHEQPE 2100
STHGQSAPST GGRQGSHHDQ AQDSSRHSAS QEGQDTIRGH PGPSRGGRQG SHHKQSVDRS 2160
GHSGSHHSHT TSQGRSDASR GQSGSRSASR QTHDKEQSGD GSRHSGSRHH EASSWADSSR 2220
HSQAGQGQSE GSRTSRRQGS SFSQDSDSEG HSEDSERRSG SASRNHRGSA QEQSRDGSRH 2280
PRSHHEDRAG HGHSADSSRQ SGTHHAQNSS GGQAASFHEQ ARSSAGERHG SHHQQSADSS 2340
RHSGIGHGQA SSAVRDSGHR GSSGSQASDS EGHSEDSDTQ SVSAHGQAGP HQQSHQESTR 2400
GRSAERSGRS GSFLYQVSTH EQSESAHGRT GPSTGGRQGS RHEQARDSSR HSASQEGQDT 2460
IHGHPGSRRG GRQGSYHEQS VDRSGHSGSH HSHTTSQGRS DASHGQSGSR SASRQTRNEQ 2520
QSGDGSRHSG SSHHEASTQA DSSRHSQSGQ GESAGSRRSR RQGSSVSQDS DSEAYPEDSE 2580
RRSESASRNR HGSSREQSRD GSRHPGSSHR DTTRHVQSSP VQSDSSTAKE HGHFSSLSQD 2640
SAYRSGIQSR GSPHSSSSYH YQSEGTERQK GQSGLVWRHG SYGSADYDYG ESGFRHSQHG 2700
SVSYNSNPVV FKERSDICKA SAFGKDHPRY YATYINKDPG LCGHSSDISK QLGFSQSQRY 2760
YYE                                                               2764
```

```
SEQ ID NO: 22          moltype = AA  length = 819
FEATURE                Location/Qualifiers
source                 1..819
                       mol_type = protein
                       organism = Bos taurus
SEQUENCE: 22
MSTLLENIND IIKIFHKYSK TDKETDTLSE KELKELVEVE FRPILKNPGD PDTAEVFMYN  60
LDRDHNNKID FTEFFLMVFK VAQVYYSYTQ RQNLQRAGQK QKKCTYHYGD EEDDTEEDKE 120
ETERKYSHSR SDGKTQDRSK SPRGRGKKRH GSKSGSKQRR GDTPTSGLRH GCSKKHESRR 180
EKKRRPSSTE PKERRHMSSV SPTRGYEEKE EEHGYENKGK TSAKCIGSEY DDSYQVCEDK 240
VTTNFQPSHS KNYGSNITKG RDTEGHSRDT GRKSVFTHAR SGSSSRNQNG SVQTHTGDNS 300
THSESQQETN SESVHRRSRN TGQRQGSHHE QSRDSSRHSG TRHGQPSTGS GGSRHRESSV 360
SQASDSEGHS EDSGRQSVTT HGRPGSSSRN QHGSSQGQTG DSSRHSESHQ GRHSDSLQRR 420
SGTSTGQRQG SHHEQSRDSS RHSGTQQGQT STGSGSRHES DSVSQASDS EGHSEDSGRQ 480
LETVLGIQSP IKEATVKLFM KGQDPARGKG RGATMSSQGT APDTLELDMD KSQLNLEMAD 540
IGNPVLVKPV TVRDTPEIQV GILRQLMEDM VPAQGTNMDP PMVRQGTVIG TQRPIKGDTI 600
RDTQEIQVGI LRQLMEDLVP AQETNMDLPM ARVETVLGTQ SPIKRGIVNL SMEGQDPALG 660
KDRGATMSSQ ETAPDTLELD MGKPQLNLEM ADIGNPVLVK PVTVRDTPEI QVGILRQLME 720
GLVQAQETNM DLPRARQETV LGTQHIIKGG TVNLSMKGQR LELGKDRGAT MSSQGTAPDS 780
LELDMDIPLL DLEMADIGNP VLVSQVTERD TQEIQVDSP                        819
```

```
SEQ ID NO: 23          moltype = AA  length = 1183
FEATURE                Location/Qualifiers
source                 1..1183
                       mol_type = protein
                       organism = Macaca mulatta
SEQUENCE: 23
MSTLLENIFA IINLFKQYSK KDKNTDTLSK KELKELLEKE FRPILKNPDD PDTVEVFMDH  60
LDIDHNKKID FTEFFLMVFK LAQAYYESTR KQNLPIAGHK HRKHSHHDKH EDNKEEENKE 120
KRKRPLSLER RNNRKGNTGR SKSPRERGGK RHESSFEKKE RKGYSPTYEE EEYGQNHHKS 180
SKKEKNKTEI TRLEHEGKRI SERPEKKEEK EDGQFDYENA GRMDEKWTES GHIAIYHAIQ 240
DEVDDTTENI LEENRRYETS RSPHDKSSLR VNRSPNANTS QIPLVEPRRR TRQRSSVSQD 300
SDSEGHSEDS ERQSESASRN HHGSVREQSR HGSRHPGSHH EDRAGHGHSA DSSTQSGTRH 360
TETSSRGQAV SSHEQARSSP GERHGSRHQQ SAESSRHSGI GRGQASSAVS DRGHQGPSGS 420
```

```
HFSDSEGHSE HSDTQSVSGH GQAGPHPHSH QESARGRSRE RSGRSGSFLY QVSTHEQSES  480
THGRTGPSSA GRQGSRNEQA RDSSRHSASH EVQDTVHGHH GSSRGRRQGS HHEQLVDSSG  540
HSGSHHSHTT SQGRSDASRG ESGARSASRQ TRHEEQSGDG SRHSGSRHHE SSNRADSSRH  600
AQSSQGQSAG FRTSTRRGSS VSQDSDSEGH SEDSERQSES ASRNHHGSVR EQSRHGSGHS  660
GSHHQDKVGH RYSGDSSRQS GTHHVETSSH GQAASSHEQT RSSPGERHGS HHQQSADSSR  720
HSGTGRGQAS SAVSDRGHQG PSGSHFSDSE GHSEHSDTQS VSGQGQAGRH PHSHQESARG  780
RSGERSGRSG SFVYQVSTHE QSESTHGRTG PSTGGRQGSR NEQARDSSRH SVSHEGQDTI  840
HGHHGSSRGG RQGSHHEQSV DSSGHSGSHH SHTTSQGRSD ASRGESGARS ASRQTRHEEQ  900
SGDGSRHSGS RHHEASNRAD SSRHAQSGQG QSAGFRTSTR RGSSVSQDSD SEGHSEDSER  960
QSESASRNHH GSVREQSRHG SRHPGSHHED RAGHGHSADS SRQSGTRHTE TSSRGQAVSS  1020
HEQARSSPGE RHGSRHQQSA ESSRHSGIGR GQASSAVSDR GHQGPSGSHF SDSEGHSEHS  1080
DTQSVSGHGQ AGPHPHSHQE SARGRSGERS GRSGSFLYQV STHEQSESTH GRTGPSSAGR  1140
QGSRNEQARD SSRHSASHEV QDTVHGHHGS SRGGRQGSHH EQS                    1183

SEQ ID NO: 24           moltype = AA  length = 2265
FEATURE                 Location/Qualifiers
source                  1..2265
                        mol_type = protein
                        organism = Macaca mulatta
SEQUENCE: 24
MTDLLRSVVT VIDVFYKYTK QDGECGTLSK DELKELLEKE FHPVLKNPDD PDTVDVIMHM  60
LDRDHDRRLD FTEFLLMIFK LTMACNKVLS KEYCKASGSK KHRRGHRHQE EESETEEDEE  120
DTPEHKSGYR HSSWSEGEEH GYSSGHSRGT VKRRHGSNSR RLGRQGHLSS SGNQERSQKR  180
YHRSSSGHSW SSGKERHGFS SGELRERINK SHVSPSREFG EEYESGSGSK SWERKGHGGL  240
SCGLEISGHE SNSTQSRSSG QKLGSSRSCS GDSRRRSHAC GYSNSSGCGR PQNASNSCQS  300
HRFGGQVNQS SYIQSGCQSG INGEQGHDCV SGGQPSGCGQ PESNSCSQSY SQRGYGAREN  360
GQPQNCGGQQ RTGSSQSSFC GQYESGGSQS CSNGQHEHGS CGRFSNSSSS NEFSKCGKHR  420
SGSGQFTSCE QHGTGLSQSS GFEQQVAGSS QTCSQYGSRS SQSSGYDEHG SSSGKTSGFG  480
QHRSGSGHSS GFGQHGSGSG QSFGFGQHGS GSGQSSGFGQ HESRSCQSSY GQHGSGSSQS  540
SGYGQHASRQ TSGFGQHGLG SGQSTGFGQY GSGSGQSSGF GQHGSGSGQS SGFGQHGSG   600
GQSSYGQHSS SSSQSSGYGQ HGSRQTSGFG QHGSGSGQST GFGQYGSSLG QSSGFGQHGS  660
GSGQSSGFGQ HESTSGQSSY GQHGFGSSQS SGCGQHGLSS GQTSGFGQHE LSSGQSSSFG  720
QHGSGSGQSS GFRQHESGSG QSSGFGQHES RSHQSSYGPH GSGSGQSSGY GQHGSSSGQT  780
SGFGQQGSSS SQYSGFGQHG SGLGQSSGFG QHGTGSGQFS GFGQHESRSH QSSYGQHGSG  840
SSQSSGYGQH GSSSGHTTGF GQHRSSSGQY SGFGQHGSGL GQSSGFGQHG TGSGQSSGFG  900
QHESRSHQSS YGQHGSGSSQ SSSYGQHGSS SGQTSGFGQH RSGSGQSSGF GQYGLGSGQS  960
SGFGQHGSGT GQSSGFARHE YRSGQSSYGQ HGTGSSQSSG CGQRESGSGP TTGFGQHVSG  1020
SDNFSSSGQH ISGSDQSTGF GQYGSGSGQS TGLGQVESQG VASGSTVHGR QETTHGQTIN  1080
TARHSQSGQG QSTQTGSRVS RRRRSSQSEN IDSEVHSRVS HRHSEHIDTQ VGSHYPESGS  1140
TVHRRQGTTH GQRGDTTRHS HSGHGQSTQT GSRTTGRQRF SHSDATDSEV HSGVSHRPHS  1200
QEHTHGQDGS QLGESQSTVH ERHETTYGQT GDATGHGYSG HGQSTQIGSR TSGRRGSGHS  1260
ESSDTEVHSG GSHRPHSQEQ THGQARSQHG ESRSTVHERH GTTHGQTGDT TRYAHYHNGQ  1320
SAQRGSRTTG RGSGHSEYSD SELYSGGSHT YSGHTHGQAQ SQHGESDSIV HERYGTTHGQ  1380
TGDTTRHAHY SHGQSKQRGS RTTGRRGSGH SEYSDSEGHS GGSHTHSGHT HGHTHGQAGS  1440
QHGESGSSGH GGQGTTHGQT GDTTRHAHYG HGQSTQRGSR TAGRRGSGHS EYSDSEGHSG  1500
VSHTHSGHTH GQAGSQHGES ESTVHERQQT THGQTGDTTR HAHYGHGQST QTGSRTTGRR  1560
GSGHSEYSDS EGHSGVSHTH SGHTHGQARS QHGESGSAIH QGQTIHGQT GDTTRHGQSG  1620
HGQSTQTGSR TTGRRGSGHS EYSDSEGHSG GSHTHSGHTH GQAGSQHGES GSTVHGRQGT  1680
IHGQTGDTTR HGQSGHGQSI ETGSRTTGRR GSGHSEYSDS EGHSGVSHTH SGHTHGQAGS  1740
QHGESESTVH ERQQTTHGQT GDITEHGHSS HGQTTQTGSR TTGRRGSGHS EYSDSEWHSG  1800
GSHTHSGHTH GQAGFQHGES GSAVHGRQGT IHGQTGDTTR HGQSGHGESI QTGSRTIGRR  1860
GSGHSEYSDS EGHSGISHTH SGHTHGQAGS QHGESGSSGH GRQGTAHGQT GDTTRHAHYD  1920
HGQSTQRGSR TAGRRGSGHS EYSDSEGHSG VSHTHSGHTH GQAGSQHGES GAAVHGRQGI  1980
IHGQTGDTTR HGQSGQGQST QRGSRTTGRR GSGHSEYSDS VGHSGVSHTH SGHTHGLAGS  2040
QHGESGSSGH GRQGTLHGQT GDTTRHAHYG HGQSTQRGSR TAGRRGSGHS EYSDSEWHSG  2100
GSHTHSGHTH GQAGSQHGES GSAVHGRQGT IHGQTGDTTR HGQSGHGQST QIGPHSSSSY  2160
NYHSEGTERE RGQSGLVWRH GSYGSADYDY GESRFRHSQH GSVSYNSNPV VFKERSDIRK  2220
ASAFGEDHPR YYARYVNRQP GLYRHSSDIS KQLGFSQSQR YYYYE                  2265

SEQ ID NO: 25           moltype = AA  length = 12
FEATURE                 Location/Qualifiers
REGION                  1..12
                        note = Description of Unknown: Human or Mouse filaggrin
                         sequence
source                  1..12
                        mol_type = protein
                        organism = unidentified
SEQUENCE: 25
SGSQASDSEG HS                                                      12

SEQ ID NO: 26           moltype = AA  length = 24
FEATURE                 Location/Qualifiers
REGION                  1..24
                        note = Description of Artificial Sequence: Synthetic peptide
VARIANT                 5
                        note = MOD_RES - Any amino acid
VARIANT                 10
                        note = MOD_RES - Any amino acid
VARIANT                 18
```

```
                         note = MOD_RES - Any amino acid
source                   1..24
                         mol_type = protein
                         organism = synthetic construct
SEQUENCE: 26
QSGEXSGRSX SFLYQVSXHE QSES                                                    24

SEQ ID NO: 27            moltype = AA   length = 345
FEATURE                  Location/Qualifiers
source                   1..345
                         mol_type = protein
                         organism = Homo sapiens
SEQUENCE: 27
QSGESSGRSR SFLYQVSSHE QSESTHGQTA PSTGGRQGSR HEQARNSSRH SASQDGQDTI    60
RGHPGSSRGG RQGSYHEQSV DRSGHSGYHH SHTTPQGRSD ASHGQSGPRS ASRQTRNEEQ   120
SGDGSRHSGS RHHEPSTRAG SSRHSQVGQG ESAGSKTSRR QGSSVSQDRD SEGHSEDSER   180
RSESASRNHY GSAREQSRHG SRNPRSHQED RASHGHSAES SRQSGTRHAE TSSGGQAASS   240
QEQARSSPGE RHGSRHQQSA DSSTDSGTGR RQDSSVVGDS GNRGSSGSQA SDSEGHSEES   300
DTQSVSAHGQ AGPHQQSHQE STRGQSGERS GRSGSFLYQV STHEQ                   345

SEQ ID NO: 28            moltype = AA   length = 345
FEATURE                  Location/Qualifiers
REGION                   1..345
                         note = Description of Artificial Sequence: Synthetic
                          polypeptide
source                   1..345
                         mol_type = protein
                         organism = synthetic construct
SEQUENCE: 28
QSGESSGRSR SFLYQVSSHE QSESTHGQTA PSTGGRQGSR HEQARNSSRH SASQDGQDTI    60
RGHPGSSRGG RQGSYHEQSV DRSGHSGYHH SHTTPQGRSD ASHGQSGPRS ASRQTRNEEQ   120
SGDGSRHSGS RHHEPSTRAG SSRHSQVGQG ESAGSKTSRR QGSSVSQDRD SEGHSEDSER   180
RSESASRNHY GSAREQSRHG SRNPRSHQED RASHGHSAES SRQSGTRHAE TSSGGQAASS   240
QEQARSSPGE RHGSRHQQSA DSSTDSGTGR RQDSSVVGDS GNRGSSGSQA SDSEGHSEES   300
DTQSVSAHGQ AGPHQQSHQE STRGQSGERS GRSGSFLYQV STHEQ                   345

SEQ ID NO: 29            moltype = AA   length = 7
FEATURE                  Location/Qualifiers
REGION                   1..7
                         note = Description of Unknown: filaggrin sequence
source                   1..7
                         mol_type = protein
                         organism = unidentified
SEQUENCE: 29
QSGESSG                                                                        7

SEQ ID NO: 30            moltype = DNA   length = 23
FEATURE                  Location/Qualifiers
misc_feature             1..23
                         note = Description of Artificial Sequence: Synthetic
                          oligonucleotide
source                   1..23
                         mol_type = other DNA
                         organism = synthetic construct
SEQUENCE: 30
gaagtgcggt tcaacaccct ccg                                                     23

SEQ ID NO: 31            moltype = DNA   length = 15
FEATURE                  Location/Qualifiers
misc_feature             1..15
                         note = Description of Unknown: operational taxonomic unit
                          sequence
source                   1..15
                         mol_type = unassigned DNA
                         organism = unidentified
SEQUENCE: 31
gatacagaga tgcat                                                              15

SEQ ID NO: 32            moltype = DNA   length = 15
FEATURE                  Location/Qualifiers
misc_feature             1..15
                         note = Description of Unknown: operational taxonomic unit
                          sequence
source                   1..15
                         mol_type = unassigned DNA
                         organism = unidentified
SEQUENCE: 32
gatacagtga tgcat                                                              15
```

-continued

```
SEQ ID NO: 33          moltype = DNA   length = 15
FEATURE                Location/Qualifiers
misc_feature           1..15
                       note = Description of Unknown: operational taxonomic unit
                        sequence
source                 1..15
                       mol_type = unassigned DNA
                       organism = unidentified SEQUENCE: 33
gatacagtag atgca                                                         15

SEQ ID NO: 34          moltype = DNA   length = 15
FEATURE                Location/Qualifiers
misc_feature           1..15
                       note = Description of Unknown: operational taxonomic unit
                        sequence
source                 1..15
                       mol_type = unassigned DNA
                       organism = unidentified SEQUENCE: 34
taccagattt acata                                                         15

SEQ ID NO: 35          moltype = DNA   length = 14
FEATURE                Location/Qualifiers
misc_feature           1..14
                       note = Description of Unknown: operational taxonomic unit
                        sequence
source                 1..14
                       mol_type = unassigned DNA
                       organism = unidentified SEQUENCE: 35
taccagatta cata                                                          14

SEQ ID NO: 36          moltype = DNA   length = 14
FEATURE                Location/Qualifiers
misc_feature           1..14
                       note = Description of Unknown: operational taxonomic unit
                        sequence
source                 1..14
                       mol_type = unassigned DNA
                       organism = unidentified SEQUENCE: 36
caggtaggat aata                                                          14

SEQ ID NO: 37          moltype = DNA   length = 15
FEATURE                Location/Qualifiers
misc_feature           1..15
                       note = Description of Unknown: operational taxonomic unit
                        sequence
source                 1..15
                       mol_type = unassigned DNA
                       organism = unidentified SEQUENCE: 37
caggtaggat aatta                                                         15

SEQ ID NO: 38          moltype = DNA   length = 15
FEATURE                Location/Qualifiers
misc_feature           1..15
                       note = Description of Unknown: operational taxonomic unit
                        sequence
source                 1..15
                       mol_type = unassigned DNA
                       organism = unidentified SEQUENCE: 38
caggtaggat aaata                                                         15

SEQ ID NO: 39          moltype = DNA   length = 13
FEATURE                Location/Qualifiers
misc_feature           1..13
                       note = Description of Unknown: operational taxonomic unit
                        sequence
source                 1..13
                       mol_type = unassigned DNA
                       organism = unidentified SEQUENCE: 39
caggtaggaa ata                                                           13

SEQ ID NO: 40          moltype = DNA   length = 14
FEATURE                Location/Qualifiers
```

-continued

```
misc_feature          1..14
                      note = Description of Unknown: operational taxonomic unit
                       sequence
source                1..14
                      mol_type = unassigned DNA
                      organism = unidentified
SEQUENCE: 40
gattacagat taca                                                              14

SEQ ID NO: 41         moltype = DNA   length = 15
FEATURE               Location/Qualifiers
misc_feature          1..15
                      note = Description of Unknown: operational taxonomic unit
                       sequence
source                1..15
                      mol_type = unassigned DNA
                      organism = unidentified
SEQUENCE: 41
gattacagat ttaca                                                             15

SEQ ID NO: 42         moltype = DNA   length = 15
FEATURE               Location/Qualifiers
misc_feature          1..15
                      note = Description of Unknown: operational taxonomic unit
                       sequence
source                1..15
                      mol_type = unassigned DNA
                      organism = unidentified
SEQUENCE: 42
gattacagaa ttaca                                                             15

SEQ ID NO: 43         moltype = AA   length = 328
FEATURE               Location/Qualifiers
source                1..328
                      mol_type = protein
                      organism = Homo sapiens
SEQUENCE: 43
SLYQVSTHEQ PDSAHGRTGT STGGRQGSHH EQARDSSRHS ASQEGQDTIR GHPGSSRGGR  60
QGSHHEQSVN RSGHSGSHHS HTTSQGRSDA SHGQSGSRSA SRQTRNEEQS GDGTRHSGSR  120
HHEASSQADS SRHSQVGQGQ SSGPRTSRNQ GSSVSQDSDS QGHSEDSERW SGSASRNHHG  180
SAQEQSRDGS RHPRSHHEDR AGHGHSADSS RKSGTRHTQN SSSGQAASSH EQARSSAGER  240
HGSRHQLQSA DSSRHSGTGH GQASSAVRDS GHRGSSGSQA TDSEGHSEDS DTQSVSGHGQ  300
AGHHQQSHQE SARDRSGERS RRSGSFLY                                      328

SEQ ID NO: 44         moltype = AA   length = 327
FEATURE               Location/Qualifiers
source                1..327
                      mol_type = protein
                      organism = Homo sapiens
SEQUENCE: 44
FLYQVSTHKQ SESSHGWTGP STGVRQGSHH EQARDNSRHS ASQDGQDTIR GHPGSSRRGR  60
QGSHHEQSVD RSGHSGSHHS HTTSQGRSDA SRGQSGSRSA SRTTRNEEQS RDGSRHSGSR  120
HHEASSHADI SRHSQAGQGQ SEGSRTSRRQ GSSVSQDSDS EGHSEDSERW SGSASRNHRG  180
SAQEQSRHGS RHPRSHHEDR AGHGHSADSS RQSGTPHAET SSSGQAASSH EQARSSPGER  240
HGSRHQQSAD SSRHSGIPRR QASSAVRDSG HWGSSGSQAS DSEGHSEESD TQSVSGHGQD  300
GPHQQSHQES ARDWSGGRSG RSGSFIY                                       327

SEQ ID NO: 45         moltype = AA   length = 327
FEATURE               Location/Qualifiers
source                1..327
                      mol_type = protein
                      organism = Homo sapiens
SEQUENCE: 45
FIYQVSTHEQ SESAHGRTRT STGRRQGSHH EQARDSSRHS ASQEGQDTIR AHPGSRRGGR  60
QGSHHEQSVD RSGHSGSHHS HTTSQGRSDA SHGQSGSRSA SRQTRKDKQS GDGSRHSGSR  120
HHEAASWADS SRHSQVGQEQ SSGSRTSRHQ GSSVSQDSDS ERHSDDSERL SGSASRNHHG  180
SSREQSRDGS RHPGFHQEDR ASHGHSADSS RQSGTHHTES SSHGQAVSSH EQARSSPGER  240
HGSRHQQSAD SSRHSGIGHR QASSAVRDSG HRGSSGSQVT NSEGHSEDSD TQSVSAHGQA  300
GPHQQSHKES ARGQSGESSG RSRSFLY                                       327

SEQ ID NO: 46         moltype = AA   length = 327
FEATURE               Location/Qualifiers
source                1..327
                      mol_type = protein
                      organism = Homo sapiens
SEQUENCE: 46
FLYQVSSHEQ SESTHGQTAP STGGRQGSRH EQARNSSRHS ASQDGQDTIR GHPGSSRGGR  60
QGSYHEQSVD RSGHSGYHHS HTTPQGRSDA SHGQSGPRSA SRQTRNEEQS GDGSRHSGSR  120
HHEPSTRAGS SRHSQVGQGE SAGSKTSRRQ GSSVSQDRDS EGHSEDSERR SESASRNHYG  180
```

```
SAREQSRHGS RNPRSHQEDR ASHGHSAESS RQSGTRHAET SSSGGQAASSQ EQARSSPGER    240
HGSRHQQSAD SSTDSGTGRR QDSSVVGDSG NRGSSGSQAS DSEGHSEESD TQSVSAHGQA    300
GPHQQSHQES TRGQSGERSG RSGSFLY                                       327

SEQ ID NO: 47              moltype = AA   length = 328
FEATURE                    Location/Qualifiers
source                     1..328
                           mol_type = protein
                           organism = Homo sapiens
SEQUENCE: 47
FLYQVSTHEQ SESAHGRTGP STGGRQRSRH EQARDSSRHS ASQEGQDTIR GHPGSSRGGR    60
QGSHYEQSVD SSGHSGSHHS HTTSQERSDV SRGQSGSRSV SRQTRNEKQS GDGSRHSGSR    120
HHEASSRADS SRHSQVGQGQ SSGPRTSRNQ GSSVSQDSDS QGHSEDSERW SGSASRNHLG    180
SAWEQSRDGS RHPGSHHEDR AGHGHSADSS RQSGTRHTES SSRGQAASSH EQARSSAGER    240
HGSHHQLQSA DSSRHSGIGH GQASSAVRDS GHRGYSGSQA SDSEGHSEDS DTQSVSAQGK    300
AGPHQQSHKE SARGQSGESS GRSGSFLY                                      328

SEQ ID NO: 48              moltype = AA   length = 327
FEATURE                    Location/Qualifiers
source                     1..327
                           mol_type = protein
                           organism = Homo sapiens
SEQUENCE: 48
FLYQVSTHEQ SESTHGQSAP STGGRQGSHY DQAQDSSRHS ASQEGQDTIR GHPGPSRGGR    60
QGSHQEQSVD RSGHSGSHHS HTTSQGRSDA SRGQSGSRSA SRKTYDKEQS GDGSRHSGSH    120
HHEASSWADS SRHSLVGQGQ SSGPRTSRPR GSSVSQDSDS EGHSEDSERR SGSASRNHHG    180
SAQEQSRDGS RHPRSHHEDR AGHGHSAESS RQSGTHHAEN SSSGGQAASSH EQARSSAGER   240
HGSHHQQSAD SSRHSGIGHG QASSAVRDSG HRGSSGSQAS DSEGHSEDSD TQSVSAHGQA    300
GPHQQSHQES TRGRSAGRSG RSGSFLY                                       327

SEQ ID NO: 49              moltype = AA   length = 327
FEATURE                    Location/Qualifiers
source                     1..327
                           mol_type = protein
                           organism = Homo sapiens
SEQUENCE: 49
FLYQVSTHEQ SESAHGRTGT STGGRQGSHH KQARDSSRHS TSQEGQDTIH GHPGSSSGGR    60
QGSHYEQLVD RSGHSGSHHS HTTSQGRSDA SHGHSGSRSA SRQTRNDEQS GDGSRHSGSR    120
HHEASSRADS SGHSQVGQGQ SEGPRTSRNW GSSFSQDSDS QGHSEDSERW SGSASRNHHG    180
SAQEQLRDGS RHPRSHQEDR AGHGHSADSS RQSGTRHTQT SSSGGQAASSH EQARSSAGER   240
HGSHHQQSAD SSRHSGIGHG QASSAVRDSG HRGYSGSQAS DNEGHSEDSD TQSVSAHGQA    300
GSHQQSHQES ARGRSGETSG HSGSFLY                                       327

SEQ ID NO: 50              moltype = AA   length = 327
FEATURE                    Location/Qualifiers
source                     1..327
                           mol_type = protein
                           organism = Homo sapiens
SEQUENCE: 50
FLYQVSTHEQ SESSHGWTGP STRGRQGSRH EQAQDSSRHS ASQDGQDTIR GHPGSSRGGR    60
QGYHHEHSVD SSGHSGSHHS HTTSQGRSDA SRGQSGSRSA SRTTRNEEQS GDGSRHSGSR    120
HHEASTHADI SRHSQAVQGQ SEGSRRSRRQ GSSVSQDSDS EGHSEDSERW SGSASRNHHG    180
SAQEQLRDGS RHPRSHQEDR AGHGHSADSS RQSGTRHTQT SSSGGQAASSH EQARSSAGER   240
HGSHHQQSAD SSRHSGIGHG QASSAVRDSG HRGSSGSQAS DNEGHSEDSD TQSVSAHGQA    300
GSHQQSHQES ARGRSGETSG HSGSFLY                                       327

SEQ ID NO: 51              moltype = AA   length = 327
FEATURE                    Location/Qualifiers
source                     1..327
                           mol_type = protein
                           organism = Homo sapiens
SEQUENCE: 51
FLYQVSTHEQ SESSHGWTGP STRGRQGSRH EQAQDSSRHS ASQYGQDTIR GHPGSSRGGR    60
QGYHHEHSVD SSGHSGSHHS HTTSQGRSDA SRGQSGSRSA SRTTRNEEQS GDSSRHSVSR    120
HHEASTHADI SRHSQAVQGQ SEGSRRSRRQ GSSVSQDSDS EGHSEDSERW SGSASRNHRG    180
SVQEQSRHGS RHPRSHHEDR AGHGHSADRS RQSGTRHAET SSSGGQAASSH EQARSSPGER   240
HGSRHQQSAD SSRHSGIPRG QASSAVRDSR HWGSSGSQAS DSEGHSEESD TQSVSGHGQA    300
GPHQQSHQES ARDRSGGRSG RSGSFLY                                       327

SEQ ID NO: 52              moltype = AA   length = 327
FEATURE                    Location/Qualifiers
source                     1..327
                           mol_type = protein
                           organism = Homo sapiens
SEQUENCE: 52
FLYQVSTHEQ SESAHGRTRT STGRRQGSHH EQARDSSRHS ASQEGQDTIR GHPGSSRRGR    60
QGSHYEQSVD RSGHSGSHHS HTTSQGRSDA SRGQSGSRSA SRQTRNDEQS GDGSRHSWSH    120
HHEASTQADS SRHSQSGQGQ SAGPRTSRNQ GSSVSQDSDS QGHSEDSERW SGSASRNHRG    180
SAQEQSRDGS RHPTSHHEDR AGHGHSAESS RQSGTHHAEN SSSGGQAASSH EQARSSAGER   240
```

-continued

```
HGSHHQQSAD SSRHSGIGHG QASSAVRDSG HRGSSGSQAS DSEGHSEDSD TQSVSAHGQA   300
GPHQQSHQES TRGRSAGRSG RSGSFLY                                      327
```

METHODS AND COMPOSITIONS FOR TREATING INFLAMMATORY SKIN DISEASE WITH RECOMBINANT MICROORGANISMS

RELATED APPLICATIONS

This application is a continuation of U.S. patent application Ser. No. 16/121,903, filed Sep. 5, 2018, now U.S. Pat. No. 12,208,124 issued Jan. 28, 2025, which claims priority to U.S. Provisional Application 62/554,271 filed on Sep. 5, 2017, and U.S. Provisional Application 62/685,687 filed on Jun. 15, 2018, the entire contents of both of which are incorporated by reference in their entireties herein.

SEQUENCE LISTING

The instant application contains a Sequence Listing which has been submitted electronically in XML file format and is hereby incorporated by reference in its entirety. Said XML copy, created on Jun. 20, 2024, is named 129062-00104_SL.xml and is 119,230 bytes in size.

BACKGROUND OF THE INVENTION

Atopic dermatitis (AD), or eczema, is a chronic, pruritic, inflammatory skin disease that affects 5-20% of children worldwide (Williams, H., et al. J Allergy Clin. Immunol. 1999; 103(1 Pt 1):125-138), and is also prevalent in many adults. The prevalence of atopic dermatitis is increasing, with some form of atopic dermatitis affecting 11% of the U.S. population (Shaw, T. E., et al. J Invest Dermatol. 2011; 131(1):67-73), or about 35 million people, with direct costs of $5 billion in the U.S. alone. The primary features of the disease are dry, scaly, itchy skin. Despite the increasing prevalence of atopic dermatitis worldwide and its significant disease burden, few targeted and effective treatment options are available. Notably, the most commonly used treatment methods include broad, non-specific approaches, including, but not limited to, skin hydration, bleach baths, UV treatment, dietary interventions, antimicrobials, antihistamines, systemic immunomodulatory agents, and the administration of topical corticosteroids (Hoare, C., et al. Health Technol. Assess. 2000; 4(37):1-191). However, despite these numerous options, few provide long-lasting resolution of symptoms, and atopic dermatitis recurrence is common in most individuals. Further, a 2013 National Health and Wellness Survey revealed a significant associated burden on atopic dermatitis patients, who, when compared with non-atopic dermatitis patients, reported higher levels of healthcare resources (healthcare provider/ER visits), lower health-related quality of life, and nearly twice as much lost work productivity. Moreover, atopic dermatitis patients had markedly higher prevalence of allergies (46% vs. 20%), asthma (22% vs. 8%), anxiety (43% vs. 21%), and depression (37% vs. 21%) (Whiteley, J., et al. Current Medical Research and Opinion. 2016:1-32). Accordingly, there is a large unmet need in view of the significant burden atopic dermatitis has on our healthcare system.

Recent research has elucidated the pathophysiology of atopic dermatitis and has revealed that a skin barrier defect is in many cases primarily responsible for the onset of atopic dermatitis, which results in both transepidermal water loss (TEWL or TWL) and increased antigen and pathogen exposure. Concurrently, atopic dermatitis is often characterized by dysbiosis (or a microbial imbalance, the severity of which is associated with disease severity; see Kong, H. H., et al.

*Genome research.* 2012; 22(5):850-859; and FIG. 1), which is a notable feature of atopic dermatitis, and a lack of diversity of the skin microbiome, which is dominated by *Staphylococcus aureus* during atopic dermatitis flares and untreated skin. Finally, there is an activated inflammatory response, particularly driven by, inter alia, IL-4/IL-13, with a predominate T-helper type 2 profile ($T_H2$), existing in lesional and non-lesional skin, indicating a systemic switch to a $T_H2$-weighted profile (Sidbury, R., et al. *Current allergy and asthma reports.* 2017; 17(7):42). An ideal atopic dermatitis treatment would thus address all of these underlying causes simultaneously, i.e. skin barrier deficiency, dysbiosis, and an activated cutaneous immune response. The present invention addresses these causes.

Engineered probiotics are a novel approach based on leveraging the skin microbiome for therapeutic purposes. Notably, an engineered probiotic has important advantages over other methods of drug delivery, as it will establish residence on the patient's skin and continuously and stably deliver therapeutic proteins in situ. Furthermore, certain strains of *Staphylococcus epidermidis* (SE) have demonstrated important beneficial immuno-modulatory and anti-pathogen effects in the skin, which are relevant to atopic dermatitis disease phenotype and severity. Moreover, the delivery of filaggrin, which is a structural protein derived from profilaggrin, further enhances the therapeutic approach due to filaggrin's role in the skin barrier and ability to reduce transepidermal water loss and improve skin hydration. The present invention has the surprising advantage of providing methods and compositions for treating skin diseases, e.g., atopic dermatitis, using a genetically engineered, recombinant strain of *Staphylococcus epidermidis* as a skin drug delivery system that secretes human filaggrin to address the pathophysiology of atopic dermatitis (e.g., AZT-01). Once applied to the skin, stable colonization of the skin and the subsequent secretion of filaggrin in situ can resolve the disease. The benefits of this invention include its safety as a non-steroidal treatment option, its efficacy due to the invention's combination of benefits from the secretion of filaggrin along with the benefits of the topical application of *Staphylococcus epidermidis*, and its ability to be therapeutically effective at even a low frequency of application (no more than once a day).

The present invention therefore addresses the long-felt need for an effective treatment for inflammatory skin diseases, such as atopic dermatitis. The present invention is also one of the first reported demonstrations of commensal skin bacteria that can secrete therapeutic proteins to treat skin disease.

SUMMARY OF THE INVENTION

The invention refers to methods and compositions for treating inflammatory skin diseases comprising, as an active principle, an engineered microorganism capable of expressing therapeutically relevant recombinant fusion polypeptides (i.e. proteins, peptides, or amino acids).

The present invention features, in a first aspect, a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide. In a related embodiment, the recombinant microorganism further comprising a third coding sequence comprising a gene capable of expressing an export signal. In yet another embodiment, the expression of the first coding sequence, second coding sequence and third coding sequence is under the control of a promoter. In other embodiments, the arrangement of the first coding sequence, second coding sequence and third coding sequences are in-frame. In yet another related embodiment, the first coding sequence, second coding sequence and third coding sequence are operably linked to a promoter. In one embodiment, the recombinant microorganism is bacteria, or a combination of bacteria. In another embodiment, the polypeptide is filaggrin, or a variant thereof. In other embodiments, the microorganism is selected from the group consisting of *Bifidobacterium, Brevibacterium, Propionibacterium, Lactococcus, Streptococcus, Staphylococcus, Lactobacillus, Enterococcus, Pediococcus, Leuconostoc,* or *Oenococcus,* or combinations thereof. In yet other embodiments, the recombinant microorganism is *Staphylococcus epidermidis. In another embodiment, the microorganism secretes a filaggrin fusion protein. In one embodiment, the polypeptide comprises an amino acid sequence selected from the group consisting of SEQ ID NO:* 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 1. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 2. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 3. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 4. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 5. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 6. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 7. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 8. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 9.

The present invention features, in a further aspect, a method for producing a live biotherapeutic composition, the method comprising (a) transfecting a cell with (i) a first coding sequence comprising a nucleic acid sequence capable of expressing a therapeutic polypeptide, and (ii) a second coding sequence comprising a nucleic acid sequence capable of expressing a cell penetrating peptide; and (b) allowing the transfected cell to produce a therapeutic polypeptide fusion protein; and (c) obtaining the live biotherapeutic composition. In a related embodiment, the method further comprises (iii) transfecting the cell with a third coding sequence comprising a nucleic acid sequence capable of expressing an export signal. In another embodiment, the first coding sequence, second coding sequence and third coding sequences are arranged in a single plasmid. In yet another embodiment, the arrangement of the first coding sequence, second coding sequence and third coding sequences are operably linked to a promoter. In other embodiments, the cell is selected from the group consisting of wherein the microorganism is selected from the group consisting of *Bifidobacterium, Brevibacterium, Propionibacterium, Lactococcus, Streptococcus, Staphylococcus, Lactobacillus, Enterococcus, Pediococcus, Leuconostoc,* or Oenococcus, or combinations thereof. In yet another embodiment, the cell is *Staphylococcus epidermidis.* In other embodiments, the therapeutic polypeptide fusion protein is a filaggrin fusion protein, or a variant thereof.

The present invention features, in another aspect, a nucleic acid comprising a nucleic acid sequence encoding a polypeptide as set forth any one of the aspects or embodiments herein.

The present invention features, in a further aspect, a composition obtained by any one of the method disclosed or described herein. In a related embodiment, the composition comprises a pharmaceutically acceptable carrier, wherein the pharmaceutically acceptable carrier is selected from the group consisting of an aqueous solution, an emulsion, a cream, a lotion, a gel, or an ointment.

The present invention features, in a further aspect, a live biotherapeutic composition comprising a recombinant microorganism wherein the recombinant microorganism comprises (i) a first coding sequence comprising a nucleic acid sequence capable of expressing a therapeutic polypeptide; (ii) a second coding sequence comprising a nucleic acid sequence capable of expressing a cell penetrating peptide; (iii) a third coding sequence comprising a nucleic acid sequence capable of expressing an export signal; and (iiv) a promoter operably linked to the first coding sequence, the second coding sequence and the third coding sequence; wherein the first coding sequence, second coding sequence and first coding sequence is capable of expressing a filaggrin fusion product, or variant thereof. In a related embodiment, the recombinant microorganism is *Staphylococcus epidermidis.* In a further embodiment, the export signal exports the filaggrin fusion product, or variant thereof, out of the recombinant microorganism. In yet another embodiment, the cell penetrating peptide facilitates the entry of the filaggrin fusion product, or variant thereof, into a human keratinocyte. In another embodiment, the composition comprises a pharmaceutically acceptable carrier, wherein the pharmaceutically acceptable carrier is selected from the group consisting of an aqueous solution, an emulsion, a cream, a lotion, a gel, or an ointment.

The present invention features, in a further aspect, a kit comprising any one of the compositions disclosed or described herein and instructions for use.

The present invention features, in a further aspect, a method of treating a skin disease comprising administering to a subject in need thereof the composition of any one of the compositions disclosed or described herein. In another embodiment, the skin disease is atopic dermatitis.

BRIEF DESCRIPTION OF THE DRAWINGS

FIG. 1A shows longitudinal trend of mean proportion of *S. aureus* in atopic dermatitis in antecubital and popliteal creases (AcPC, n=12) grouped by no-treatment (trt) and intermittent-trt flares. FIG. 1B shows proportion of *S. aureus* and Shannon diversity index in AcPc. Partial correlation (adjusting for disease state, AcPc). FIG. 1C shows longitudinal trend of mean proportion of *S. epidermidis* in AcPc. FIG. 1D shows correlation of proportion of *S. aureus* versus objective SCORAD for each site (AcPc, Volar forearm [Vf], Nares [N]). Partial correlation (adjusting for disease state). FIG. 1E shows longitudinal Shannon diversity trend in atopic dermatitis grouped by no-treatment and intermittent-trt flares (n=12, Ac). FIG. 1F atopic dermatitis microbiome progression hypothesis. (*) Proposed relationship among shifts in skin microbial diversity, the proportion of *Staphylococcus*, and disease severity.

FIG. 3A shows fluorescence and light wavelength overlays of RHE at ~25 μm at two hours past application of *Staphylococcus epidermidis*-GFP. FIG. 3B-3D shows fluorescence and light wavelength overlays of RHE two hours after dermaroller application then topical *Staphylococcus epidermidis*-GFP application. Depths taken at 0 μm FIG. 3B, 50 μm FIG. 3C, and 70 μm FIG. 3D.

FIG. 4A-4E depicts the characterization of SE-GFP colonization in mice. FIG. 4A-4C shows in vivo two-photon microscopy of mouse skin three days following treatment of GFP-expressing *S. epidermidis*. FIG. 4A 25 μm; and FIG. 4B 50 μm depth of unshaved mouse ear skin, and FIG. 4C 80 μm depth on shaved dorsal skin. FIG. 4D Light microscopy of dorsal skin of mice following SE-GFP application. FIG. 4E Light microscopy of dorsal skin of mice following SE-GFP application.

FIG. 5A-5N depicts the characterization of protein with and without the RMR signal using 50 μg GFP as a reporter in RHE. FIG. 5A-5D show two-photon images of topically applied GFP with (FIG. 5C, FIG. 5D) or without (FIG. 5A, FIG. 5B) the RMR signal at 30 minutes (FIG. 5A, FIG. 5C, FIG. 5E, FIG. 5G) or 60 minutes (FIG. 5B, FIG. 5D, FIG. 5F, FIG. 5H). Images are compiled Z-stacks projected onto a 2D plane. (FIG. 5I-FIG. 5N) Confocal images of GFP (FIG. 5K, FIG. N), GFP+RMR (FIG. 5J, FIG. 5M) or vehicle (FIG. 5I, FIG. 5L) using light (FIG. 5L-FIG. 5N) or fluorescent (FIG. 5I-FIG. 5K) wavelengths.

FIG. 6 discloses SEQ ID NOS 30-33, 33-35, 35-36, and 36-42, respectively, in order of appearance.

FIG. 13A-13C show alignments shows an alignment of human filaggrin dimers hFLG[3-4](SEQ ID NO: 43), hFLG [5-6](SEQ ID NO: 44), hFLG[7-8](SEQ ID NO: 45), hFLG [9-10](SEQ ID NO: 46), hFLG[11-12](SEQ ID NO: 47), hFLG[13-14](SEQ ID NO: 48), hFLG[15-16](SEQ ID NO: 49), hFLG[17-18](SEQ ID NO: 50), hFLG[19-20](SEQ ID NO: 51), hFLG[21-22](SEQ ID NO: 52).

DETAILED DESCRIPTION OF THE INVENTION

I. Overview and Definitions

Figures 1A, 1B, 1C:
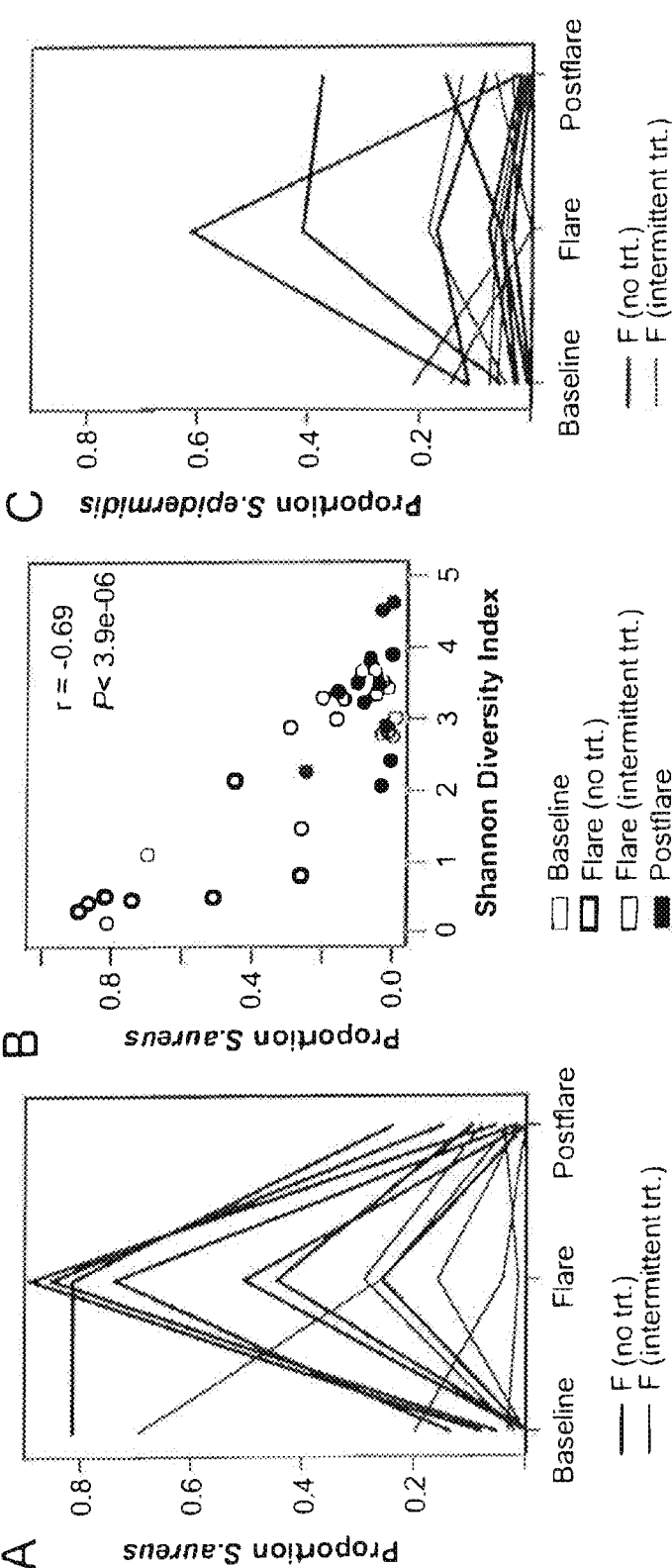
FIG. 1A-F depicts the relationship between staphylococcal species and atopic dermatitis.
Figure 1D:
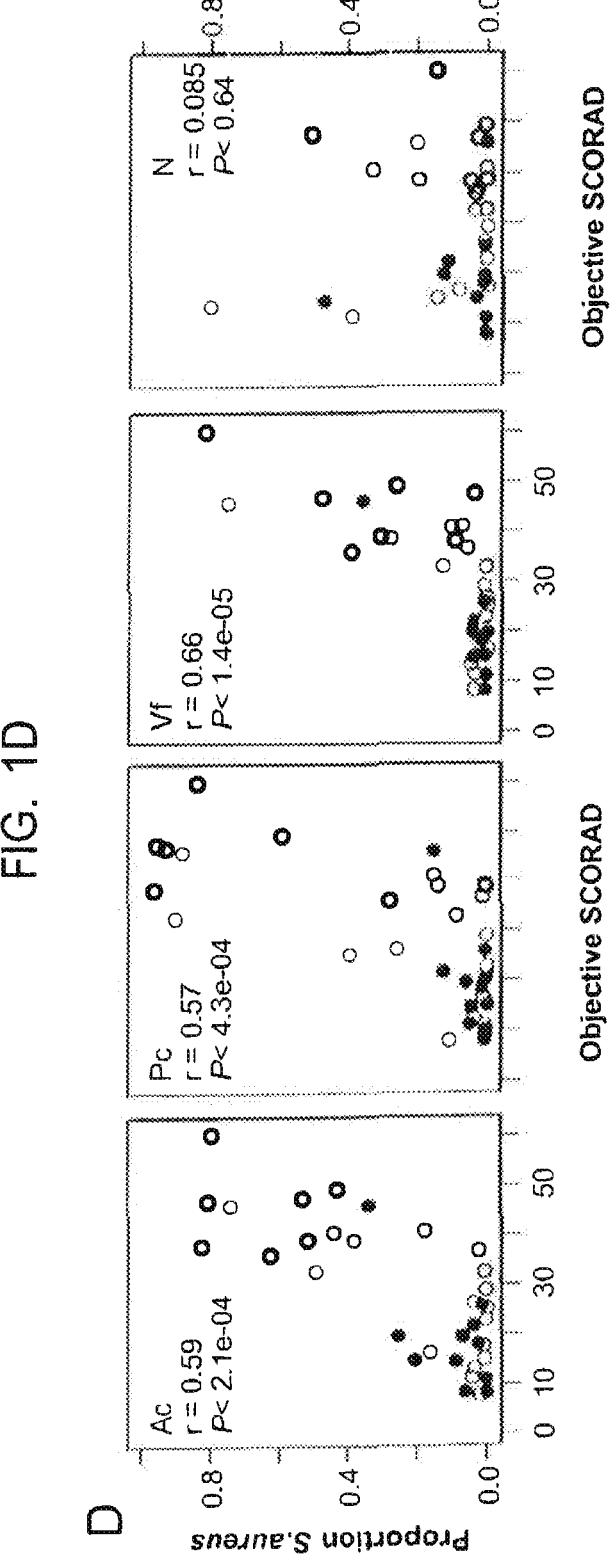
Figure 1E:
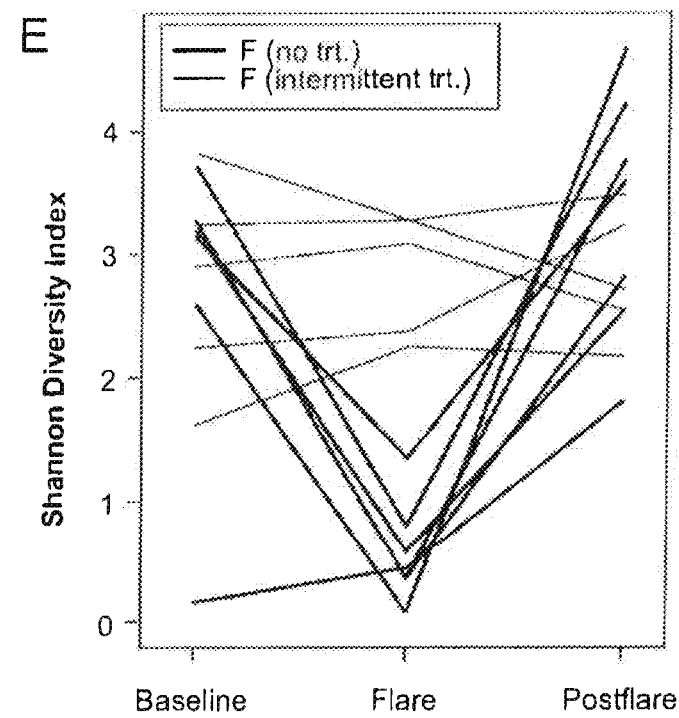
Figure 1F:
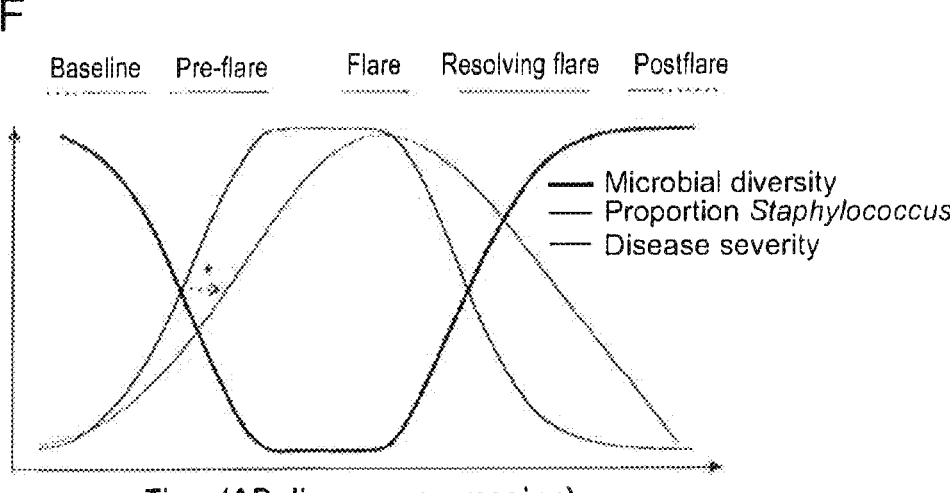

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

As used herein, the following terms have the following meanings unless expressly stated to the contrary: As used herein, the term "abnormal skin condition" or a "skin disease" (e.g., an inflammatory skin disease) refers to a skin state or condition that is generally undesirable or deleterious compared to the normal or baseline condition of human skin. Examples of abnormal skin conditions include: psoriasis, acne, atopic dermatitis, allergic contact dermatitis, epidermolytic hyperkeratosis, seborrheic dermatitis, eczema, dry skin, allergy, rashes, UV-irritated skin, detergent irritated skin (including irritation caused by enzymes and molecules used in washing detergents and sodium lauryl sulfate), thinning skin (e.g. skin from the elderly and children), bullous pemphigoid, pemphigus vulgaris, impetigo, vitiligio, baldness, and hirsutism.

As used herein, the terms "patient" or "subject", refers to a human or animal (in the case of an animal, more typically a mammal such as domesticated mammals, or animals such as poultry animals and fish and other seafood or freshwater food creatures), that would be subjected to the treatments and compositions of the present invention. Such patient or subject would be considered to be in need of the pharmaceutical compositions of the present invention or of the methods of treating, preventing, or reducing the risk of an abnormal skin condition or a skin disease (e.g., an inflammatory skin disease).

As used herein, the term "therapeutically effective amount" refers to an amount of a pharmaceutical active compound, a live biotherapeutic composition, a combination of compounds or compositions, or an amount of pharmaceutical active compound delivered by an engineered bacterial strain or strains, for example a skin treatment agent or agents, when administered alone or in combination, to treat, prevent, or reduce the risk of a disease state or condition, for example an abnormal skin condition or a skin disease (e.g., an inflammatory skin disease). The term also refers to an amount of a pharmaceutical composition containing an active compound or combination of compounds or an engineered bacterial strain or strains that delivers a pharmaceutical active compound. For example, an effective amount refers to an amount of the compound or an amount of the compound delivered by an engineered bacterial strain (or a recombinant bacterial strain) or strains present in a formulation given to a recipient patient or subject sufficient to elicit biological activity, for example, activity for treating or preventing an abnormal skin condition or a skin disease (e.g., an inflammatory skin disease).

As used herein, the phrase "pharmaceutically acceptable" refers to those active compounds, materials, engineered bacterial strain or strains, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio. As used herein, the term "treating" refers to providing a therapeutic intervention to cure or ameliorate an abnormal skin condition.

As used herein, the term "preventing", refers to completely or almost completely stopping an abnormal skin condition from occurring, for example when the patient or subject is predisposed to an abnormal skin condition or at risk of contracting an abnormal skin condition. Preventing can also include inhibiting, i.e. arresting the development, of an abnormal skin condition.

As used herein, the term "reducing the risk of," refers to lowering the likelihood or probability of an abnormal skin condition from occurring, for example when the patient or subject is predisposed to an abnormal skin condition or at risk of contracting an abnormal skin condition.

As used herein, the term "engineered bacterial strain," or a "recombinant bacterial strain" refers to a strain of bacteria that has been "genetically modified" or "engineered" by the introduction of DNA prepared outside the organism into the bacterial strain. For example, the introduction of a plasmid containing new genes or other nucleic acid sequence(s) into bacteria will allow the bacteria to express those genes or other nucleic acid sequence(s). Alternatively, the plasmid containing new genes or other nucleic acid sequence(s) can be introduced to the bacteria and then integrated into the bacteria's genome, where the bacteria will express those genes or other nucleic acid sequence(s).

As used herein, the terms "carriers", "carrier system" or "vehicles" refer to compatible substances that are suitable for delivering, containing, or "carrying" a pharmaceutical active ingredient or other materials for administration in a topically applied composition to a patient or subject. Carriers useful herein should be pharmaceutically acceptable. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue. Further examples of "carriers" include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers.

As used herein, the terms "polypeptide" or "protein" refer to biological molecules, or macromolecules composed of amino-acid residues bonding together in a chain. The definition of polypeptides used herein is intended to encompass proteins (generally higher molecular weight) composed of one or more long chains of amino acid residues and small peptides (generally lower molecular weight) of a few amino acids. In other embodiments, a single amino acid, although not technically a polypeptide, is also considered within the scope of the invention.

As used here, the term "live biotherapeutic product" (or LBP) refers to a product candidate(s) containing bacteria, yeast, and/or other microorganisms.

The term "isolated" for the purposes of the present invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

An "isolated nucleic acid molecule" (such as, for example, an isolated promoter) is one which is separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule in the genomic DNA of the organism from which the nucleic acid molecule is derived.

Figures 2A, 2B:
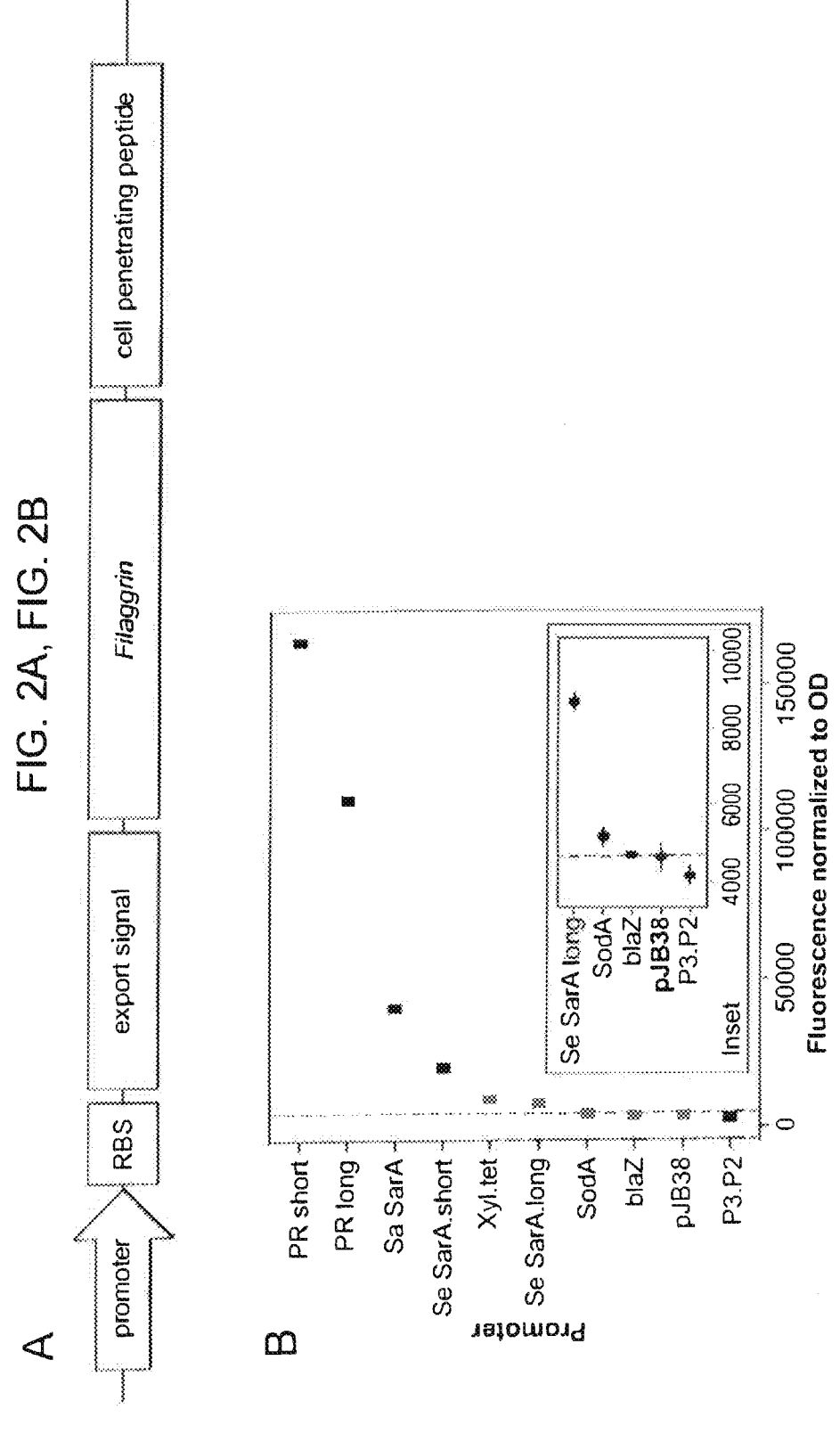
FIG. 2A depicts a schematic drawing of a *Staphylococcus epidermidis*-based protein delivery system, as described herein. The construct design comprises a promoter, a ribosome binding site (RBS), an export signal, a filaggrin expression sequence, and a cell-penetrating peptide sequence.
FIG. 2B displays the characterization of certain promoters for tunable control of protein expression (using GFP as a reporter).
Figures 2C, 2D:
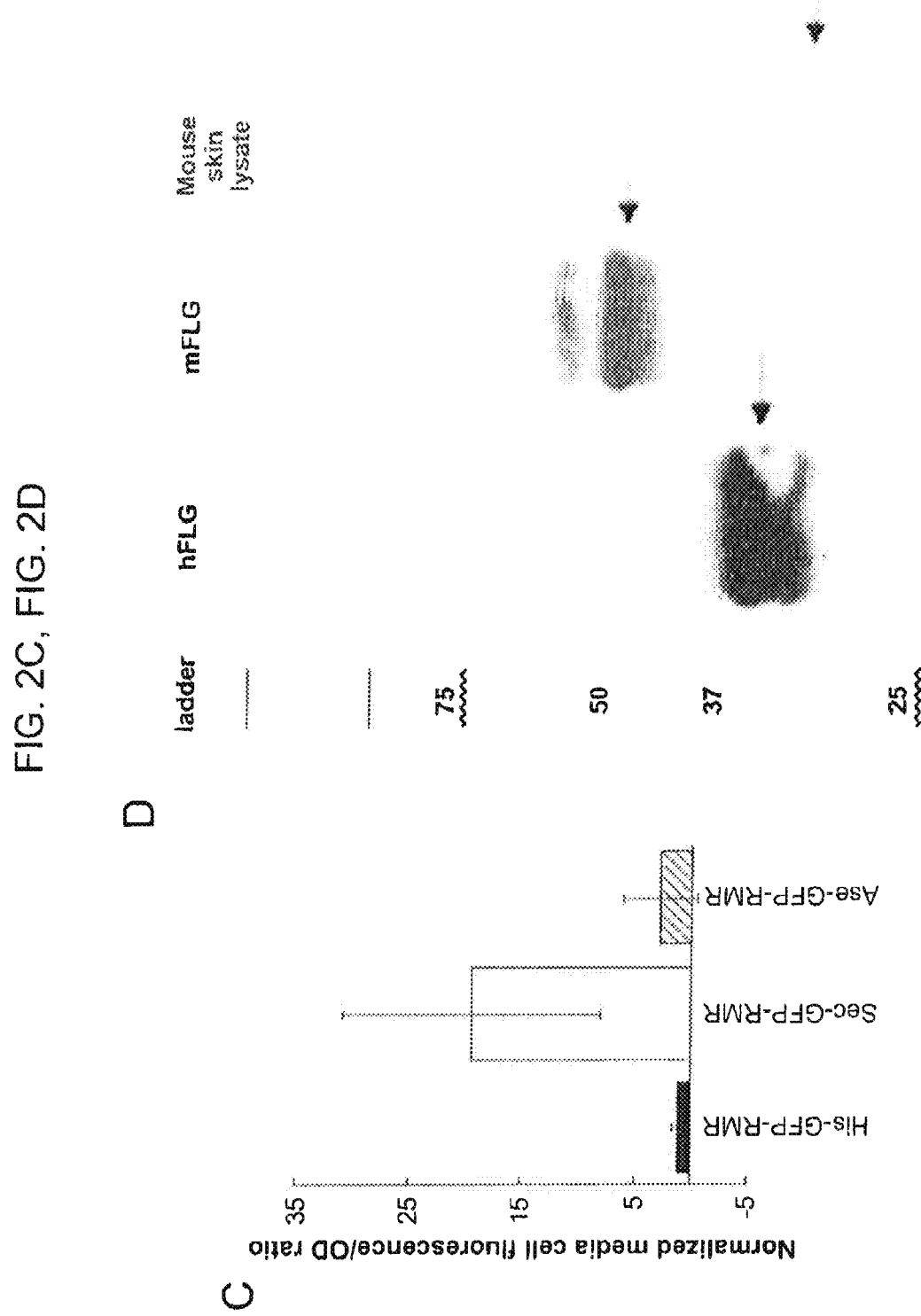
FIG. 2C shows characterization of export signals for protein export out of SE (GFP used as reporter).
FIG. 2D shows Western blot analysis of human filaggrin produced from *Staphylococcus epidermidis*, mouse filaggrin produced from *Staphylococcus epidermidis*, and whole mouse skin (anti-mouse flaggrin antibodies were used).

The present invention provides skin-colonizing bacteria that are genetically altered to express recombinant therapeutic polypeptides for the treatment or prevention of skin disease (FIG. 2). Using genetically engineered protein-producing bacteria has several advantages over the prior art method of treating skin disease. Therapeutic proteins are able to treat the underlying cause of defects leading to the skin condition. Further, bacteria are able to self-replicate while retaining the inserted gene to continuously produce the therapeutic protein.

The present invention provides skin-colonizing bacteria, such as for example, *Staphylococcus epidermidis*, that are genetically altered to express human filaggrin. Using genetically engineered filaggrin-producing bacteria has several advantages over using filaggrin supplementation. First, bacteria are able to self-replicate while retaining the inserted filaggrin gene. Second, *S. epidermidis* is normally present on the skin and has been shown to inhibit growth of *Staphylococcus aureus*, a bacterial species of the same genre that dominates the skin flora in AD flares.

II. Methods and Compositions of the Invention

The present invention provides skin-colonizing microorganisms, e.g., bacteria, that are genetically altered to express recombinant therapeutic polypeptides for the treatment or prevention of skin disease (FIG. 2). Using genetically engineered protein-producing microorganisms, e.g., bacteria, has several advantages over the prior art method of treating skin disease. Therapeutic proteins are able to treat the underlying cause of defects leading to the skin condition. Further, microorganisms, e.g., bacteria, are able to self-replicate while retaining the inserted nucleic acid (e.g., a gene) to continuously produce the therapeutic protein.

The present invention provides skin-colonizing microorganisms, e.g., bacteria, such as for example, *Staphylococcus epidermidis*, that are genetically altered to express therapeutic proteins, e.g., human filaggrin. Using genetically engineered filaggrin-producing microorganisms, e.g., bacteria, has several advantages over using filaggrin supplementation. First, microorganisms, e.g., bacteria, are able to self-replicate while retaining the inserted filaggrin nucleic acid sequence (e.g., a gene). Second, *S. epidermidis* is normally present on the skin and has been shown to inhibit growth of *Staphylococcus aureus*, a bacterial species of the same genre that dominates the skin flora in atopic dermatitis flares.

Bacterial Strains

The present invention provides genetically altered microorganisms, e.g., bacteria, capable of expressing recombinant therapeutic proteins. A wide range of microorganisms are suitable for use in the present invention. Examples include, but are not limited to, non-pathogenic and commensal bacteria. Bacteria suitable for use in the present invention include, but are not limited to, *Bifidobacterium, Brevibacterium, Propionibacterium, Lactococcus, Streptococcus, Staphylococcus* (e.g., *S. epidermidis*), *Lactobacillus* (e.g., *L. acidophilus*), *Pediococcus, Leuconostoc,* or Oenococcus. In certain embodiments of the invention, the bacterium is *Staphylococcus epidermidis*. In preferred embodiments of the invention, the strain of *S. epidermidis* to be used is incapable of producing biofilms. One such example of a strain of *S. epidermidis* incapable of producing biofilms is *S. epidermidis* strain ATCC 12228. However, in yet other embodiments of the invention, other related or similar species found on the skin can be used.

Therapeutic Proteins

The present invention provides genetically altered microorganisms, e.g., bacteria, capable of expressing recombinant therapeutic proteins.

In some embodiments, the disclosure is directed to therapeutic proteins that include a filaggrin polypeptide amino acid sequence. In some embodiments, the disclosure is directed to therapeutic proteins that include a filaggrin polypeptide amino acid sequence and a cell penetrating polypeptide amino acid sequence. In some embodiments, the disclosure is directed to therapeutic proteins that include a filaggrin polypeptide amino acid sequence, a cell penetrating polypeptide amino acid sequence and a secretion signal or export signal polypeptide sequence. As used herein, a "polypeptide" generally is defined herein to refer to a peptide sequence of about 2 to about 10,000 or more amino acid residues. The term "amino acid" not only encompasses the 20 common amino acids in naturally synthesized proteins, but also includes any modified, unusual, or synthetic amino acid. One of ordinary skill in the art would be familiar with modified, unusual, or synthetic amino acids.

The polypeptides of the present invention may possess deletions and/or substitutions of amino acids relative to the native sequence; thus, sequences with a deletion, sequences with a substitution, and sequences with a deletion and a substitution are contemplated for inclusion in the polypeptides of the present invention. In some embodiments, these polypeptides may further include insertions or added amino acids, such as linkers.

Substitutional or replacement variants typically contain the exchange of one amino acid for another at one or more sites within the protein and may be designed to modulate one or more properties of the polypeptide, particularly to increase its efficacy or specificity. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In addition to a deletion or substitution, the polypeptides may possess an insertion one or more residues. This may include the addition of one or more amino acid residues.

Amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Filaggrin

In some embodiments, the disclosure is directed to therapeutic proteins that include a filaggrin polypeptide amino acid sequence. In preferred embodiments of the invention, the therapeutic protein comprises human filaggrin. Human filaggrin is expressed by a human gene encoding filaggrin (FLG). Filaggrin is a protein produced by differentiating keratinocytes and functions to aggregate keratin filaments into a cytoskeleton, which, in combination with other components, comprises the cornified cell envelope. FLG is a large gene located on chromosome lq21 that produces profilaggrin, an insoluble polyprotein that is proteolyzed to release functional filaggrin monomers (Armengot-Carbo et al. 2014). The therapeutic protein (and, i.e., the gene from which the protein is expressed) of the invention may be from any mammal. Non-limiting examples include, but are not limited to, mouse, rat, rabbit, goat, sheep, horse, cow, dog, primate, or human gene sequence.

The filaggrin amino acid sequences contemplated for inclusion in the polypeptides, compositions, and methods of the present invention may be obtained from any source. For example, the filaggrin amino acid may be obtained from a natural source or may be chemically synthesized. The filaggrin amino acid sequence may be from any species. For example, it may be a mammalian filaggrin amino acid sequence. Non-limiting examples include mouse, rat, rabbit, goat, sheep, horse, cow, dog, cat, primate, or human amino acid sequence. In preferred embodiments, the filaggrin amino acid sequence is a human amino acid sequence. Non-limiting examples of filaggrin proteins are set forth in Table 1, below.

TABLE 1

| Sequence | GenBank Accession No. | SEQ ID NO. |
| --- | --- | --- |
| Filaggrin, *Homo sapiens* | NP_002007.1 | 1 |
| Filaggrin, *Homo sapiens* | AAA52454 | 10 |
| Filaggrin, *Homo sapiens* | P20930.3 | 11 |
| Filaggrin, *Mus musculus* | XP_017175331.1 | 12 |
| Filaggrin, *Mus musculus* | AAM23016 | 13 |
| Filaggrin, *Mus musculus* | AAA75559 | 14 |
| Filaggrin, *Mus musculus* | AAA37626 | 15 |
| Filaggrin, *Mus musculus* | XP_485270 | 16 |
| Filaggrin, *Mus musculus* | P11088 | 17 |
| Filaggrin, *Mus musculus* | EDL00668.1 | 18 |
| Filaggrin, *Rattus norvegicus* | EDL87862 | 19 |
| Filaggrin, *Pan troglodytes* | XP_001134714 | 20 |
| Filaggrin, *Pan troglodytes* | XP_513808 | 21 |
| Filaggrin, *Bos taurus* | XP_001255583 | 22 |
| Filaggrin, *Macaca mulatta* | XP_001101725.1 | 23 |
| Filaggrin, *Macaca mulatta* | XP_001109011.1 | 24 |

In some embodiments, the filaggrin amino acid sequence includes any of the amino acid sequences set forth in Table 1. In particular embodiments, the filaggrin amino acid sequence includes Gen Bank Accession No. NP_002007.1 (SEQ ID NO:1).

In some embodiments, the filaggrin amino acid sequence includes 20, 30, 40, 50, 60, 70, 80, 90, 100, 120, 130, 150, 150, 160, 170, 180, 190, 200, 210, 220, 230, 240, 250, 260, 270, 280, 290, 300, 310, 320, 330, 340 or more consecutive amino acids of any of the amino acid sequences set forth in Table 1, or any range of amino acids derivable therein, so long as the filaggrin amino acid sequence when conjugated to a cell penetrating peptide and/or export or secretion signal retains at least some of the function of a native filaggrin amino acid sequence conjugated to the same cell penetration peptide and/or export or secretion signal.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with a native filaggrin amino acid sequence, or any range of percent sequence identify derivable therein. In one embodiments, the filaggrin amino acid sequence is an amino acid sequence selected from Table 1. In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 1.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 2.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 3.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 4.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 5.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 6.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 7.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 8.

In some embodiments, the human filaggrin consensus sequence is a consensus sequence shown as SEQ ID NO: 9, and refers to a sequence formed from the most frequently occurring amino acids in hFLG[3-4], hFLG[5-6], hFLG[7-8], hFLG[9-10], hFLG[11-12], hFLG[13-14], hFLG[15-16], hFLG[17-18], hFLG[19-20], hFLG[21-22].

```
                                                   SEQ ID NO: 9
XLYQVSTHXQXDSXHGXTXXSTXXRQXSHXXQAXXXSRHSXSQXG      100
QDTIRGHPGXXXXGRQGXXXEXXVXXSGHSGXHHSHTTXQXRSDA
SHGXSGXRSA

SRXTXXXXQSXDXTRHSXSRHHEXXSXAXXSXHSXXGQXXSXGXR      200
XSRXXGSSXSQDXDSXXHSEDSERXSXSASRNHXGSXXEQXRXGS
RXPXXHXEDR

AXHGHSADXSRKSGTXHXXXSSXGQAASSXEQARSSXGERHGSRH      300
QXQSADSSXXSGXXHXQXSSAVXDSXXXGXSGSQATXXEGHSEDS
DTQSVSGXGX

XGXHQQSHXESXRXXSGXXSXRSXSFLY.                      328
```

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 9.

"Sequence identity" is defined as the percentage of amino acid residues in a candidate sequence that are identical with the amino acid residues at corresponding positions in a native polypeptide sequence, after aligning the sequences and introducing gaps if necessary, to achieve the maximum percent sequence identity, and not considering any conservative substitutions as part of the sequence identity. The % sequence identity values may be generated by the NCBI BLAST2.0 software as defined by Altschul et al. (1997). The parameters are set to default values, with the exception of Penalty for mismatch, which is set to −1.

In preferred embodiments of the invention, the therapeutic protein comprises a recombinant fusion protein comprising filaggrin operably linked to a cell penetrating protein (CPP). In other embodiments of the invention, the therapeutic protein comprises a recombinant fusion protein comprising filaggrin operably linked to an export or secretion signal, which allows the recombinant filaggrin to be exported out of the microorganism (e.g., bacteria). In another embodiment, the therapeutic protein comprises a recombinant fusion protein comprising filaggrin operably linked to a cell penetrating protein (CPP) and to an export or secretion signal.

Furthermore, the polypeptides set forth herein may comprises a sequence of any number of additional amino acid residues at either the N-terminus or C-terminus of the amino acid sequence that includes the filaggrin amino acid sequence and the cell penetrating protein (CPP) and/or export or secretion signal. For example, there may be an amino acid sequence of about 3 to about 10,000 or more amino acid residues at either the N-terminus, the C-terminus, or both the N-terminus and C-terminus of the amino acid sequence that includes the filaggrin amino acid sequence and the cell penetrating peptide and/or export or secretion signal.

Secretion Signals

Secretion signals or export signals are peptide sequences on a protein that facilitate the export of the protein through the secretory pathway, which ultimately results in the protein being secreted from the cell. In the present invention, any secretion signal that facilitates the export of a protein, such as a protein comprising filaggrin, out of a microorganism (e.g., a bacterial cell) is contemplated as a secretion signal.

Cell Penetrating Peptides

A cell penetrating peptide is a peptide sequence that facilitates or mediates the delivery of a biomolecule (e.g., a protein) in vivo without using any receptors and without causing any significant membrane damage. Cell penetrating peptides that facilitate entry into the skin keratinocytes are contemplated as a cell penetrating peptides of the present invention.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises a filaggrin polypeptide amino acid sequence.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 1.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 2.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 3.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 4.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 5.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 6.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 7.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 8.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 9.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 2.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 3.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 4.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 5.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 6.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 7.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 8.

Nucleic Acids

The present invention includes nucleic acids that include a nucleic acid sequence that encodes a recombinant polypeptide of the present invention. Some embodiments of the present invention include a nucleic acid that includes a nucleic acid sequence that encodes a polypeptide as set forth above. Further embodiments include a nucleic acid that encodes a filaggrin amino acid sequence. The filaggrin amino acid sequence is any filaggrin amino acid sequence as set forth herein. In some embodiments, the nucleic acid is comprised in an expression vector. The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between 3 and about 100 nucleobases in length. The term "polynucleotide" refers to at least one molecule of greater than about 100 nucleobases in length.

These definitions refer to a single-stranded or double-stranded nucleic acid molecule. Double stranded nucleic acids are formed by fully complementary binding, although in some embodiments a double stranded nucleic acid may formed by partial or substantial complementary binding. Thus, a nucleic acid may encompass a double-stranded molecule that comprises one or more complementary strand (s) or "complement(s)" of a particular sequence, typically comprising a molecule. As used herein, a single stranded nucleic acid may be denoted by the prefix "ss" and a double stranded nucleic acid by the prefix "ds".

Genetic Construct

The present invention utilizes standard molecular biology techniques, e.g., those described in (Sambrook et al. 2001). An example of the genetic construct used for this invention is pAZT, which is based on pJB38, an allelic exchange *E. coli*-staphylococcal shuttle vector, further comprising additional design features on the plasmid to improve functionality (Bose, J. L., et al. Applied and environmental microbiology. 2013; 79(7):2218-2224). The plasmid is constructed by inserting cDNA of a gene encoding a therapeutic protein into a restriction site, using standard molecular biology techniques (FIG. 2). The insert further comprises a coding sequence driven by a promoter. Such a promoter can be either constitutive or inducible. Examples of inducible promoters include those that are activated by chemical compounds such as alcohols, sugars, metals, or tetracycline, or by physical factors such as light or high temperatures.

The mRNA sequence of human FLG has a Genebank accession No. NM_002016. A plasmid pAZT was constructed by inserting part of the FLG cDNA into a restriction site of pJB38. The insert contains a nucleic acid coding sequence driven by a promoter. The construct further comprises a nucleic acid sequence encoding a secretion signal and a cell penetrating peptide, thus resulting in a recombinant filaggrin fusion protein.

Uses of Recombinant Bacterial Strain

It will be understood that the skin disease to be treated can be any disease or disorder associated with skin. In preferred embodiments the disorder is selected from the group consisting of atopic dermatitis, psoriasis, acne, allergic contact dermatitis, epidermolytic hyperkeratosis, seborrheic dermatitis, eczema, dry skin, allergy, rashes, UV-irritated skin, detergent irritated skin (including irritation caused by enzymes and compounds used in washing detergents and sodium lauryl sulfate), thinning skin (e.g. skin from the elderly and children), bullous pemphigoid, pemphigus vulgaris, impetigo, vitiligio, baldness, and hirsutism, Examples of proteins that can be administered according to the invention are preferably eukaryotic proteins. These proteins include, but are not limited to, single amino acids, small peptides, and large proteins. More particularly, genes encoding proteins that are useful in the invention as recombinant therapeutic proteins include, but are not limited to, the following: members of the interleukin family of genes, including, but not limited to, IL-2, IL-3, IL-4, IL-5, IL-6, IL-7, IL-8, IL-9, IL-10, IL-11, IL-12, IL-13, IL-14 and IL-15 and genes encoding receptor antagonists thereof. Genes which encode hematopoietic growth factors, including but not limited to, erythropoietin, granulocyte colony stimulating factor, granulocyte macrophage colony stimulating factor, macrophage colony stimulating factor, stem cell factor, leukemia inhibitory factor and thrombopoietin are also contemplated in the invention. Genes encoding neurotropic factors are also contemplated, including but not limited to, nerve growth factor, brain derived neurotropic factor and ciliary neurotropic factor. In addition, genes which encode interferons, including, but not limited, to IFN-alpha, IFN-beta and IFN-gamma are included. Further contemplated in the present invention are genes encoding chemokines such as the C-C family and the C-X-C family of cytokines, genes encoding hormones, such as proinsulin and growth hormone, and genes encoding thrombolytic enzymes, including tissue plasminogen activator, streptokinase, urokinase or other enzymes such as trypsin inhibitor. The invention further includes genes which encode tissue repair factors, growth and regulatory factors including, but not limited to, oncostatine M, platelet-derived growth factors, fibroblast growth factors, epidermal growth factor, hepatocyte growth factor, bone morphogenic proteins, insulin-like growth factors, calcitonin and transforming growth factor alpha and beta. Further contemplated genes include genes encoding structural proteins including filaggrin, actin, collagen, fibrillin, elastin, or scleroprotein.

Formulations

It will be further apparent that a formulation for use according to the present invention may comprise any pharmaceutically effective amount of a genetically engineered microorganism, e.g., bacteria, to produce a therapeutically effective amount of a desired polypeptide, for example, at least about 0.01%, about 0.05%, about 0.1%, about 0.2%, about 0.3%, about 0.4%, about 0.5%, about 0.6%, about 0.7%, about 0.8%, about 0.9%, about 1.0%, about. 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 2.0%, about 25.0%, about 3.0%, about 35.0%, about 40.0%, about 45.0%, about 50.0% or more by weight of the genetically engineered microorganism, e.g., bacteria, the upper limit of which is about 90.0% by weight of the genetically engineered microorganism, e.g., bacteria.

In an alternative embodiment, the formulation for use according to the present invention can comprise, for example, at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, or more by weight of a genetically engineered microorganism, e.g., bacteria.

The topical formulation for use in the present invention can be in any form suitable for application to the body surface, such as a cream, lotion, sprays, solution, gel, ointment, paste, plaster, paint, bioadhesive, suspensions, emulsions, or the like, and/or can be prepared so as to contain liposomes, micelles, and/or microspheres. Such a formulation can be used in combination with an occlusive overlayer so that moisture evaporating from the body surface is maintained within the formulation upon application to the body surface and thereafter. The formulation can include a living biotherapeutic composition and can comprise at least one a genetically engineered microorganism, e.g., an engineered bacterial strain, that produces a recombinant polypeptide. This engineered living biotherapeutic composition can deliver the polypeptide directly to the skin for treating or preventing abnormal skin conditions, and/or skin diseases (e.g., inflammatory skin diseases).

Topical formulations include those in which any other active ingredients are dissolved or dispersed in a dermatological vehicle known in the art, e.g. aqueous or nonaqueous gels, ointments, water-in-oil or oil-in-water emulsions. Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as MIGLYOL, or silicone oils such as dimethicone). Depending upon the nature of the formulation as well as its intended use and site of application, the dermatological vehicle employed can contain one or more components (e.g., when the formulation is an aqueous gel, components in addition to water) selected from the following: a solubilizing agent or solvent (e.g. a β-cyclodextrin, such as bydroxypropyl β-cyclodextrin, or an alcohol or polyol such as ethanol, propylene glycol or glycerol); a thickening agent (e.g. hydroxyethylceliulose, hydroxypropylcellulose, carboxymethylcellulose or carbomer); a gelling agent (e.g. a polyoxyethylene-polyoxy-propylene copolymer); a preservative (e.g. benzyl alcohol, benzalkonium chloride, chlorhexidine, chlorbutol, a benzoate, potassium sorbate or EDTA or salt thereof); and pH buffering agent(s) (such as a mixture of dihydrogen phosphate and hydrogen phosphate salts, or a mixture of citric acid and a hydrogen phosphate salt).

A pharmaceutically acceptable carrier can also be incorporated in the formulation of the present invention and can be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers. The term "pharmaceutically acceptable" or "pharmaceutically acceptable carrier" is used herein to refer to a compound or composition that can be incorporated into a pharmaceutical formulation without causing undesirable biological effects or unwanted, interaction with other components of the formulation, "carriers" or "vehicles" as used herein refer to carrier materials suitable for incorporation in a topically applied composition. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue.

Cream bases are water-washable, and contain an oil phase, an emulsifier, and an aqueous phase. The oil phase, also called the "internal" phase, is generally comprised of petrolatum and a fatty alcohol such ascetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions are preparations to be applied to the skin surface without friction, and are typically liquid or semiliquid preparations in which particles, including the active agent, are present in a water or alcohol base. Lotions are usually suspensions of solids, and preferably, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like. Solutions are homogeneous mixtures prepared by dissolving one or more chemical substances (solutes) in a liquid such that the molecules of the dissolved substance are dispersed among those of the solvent. The solution can contain other pharmaceutically or cosmetically acceptable chemicals to buffer, stabilize or preserve the solute. Common examples of solvents used in preparing solutions are ethanol, water, propylene glycol or any other acceptable vehicles. As is of course well known, gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred organic macromolecules, i.e., gelling agents, are cross-linked acrylic acid polymers such as the "carbomer" family of polymers, e.g., carboxypolyalkylenes that can be obtained commercially under the Carbopol trademark. Also preferred are hydrophilic polymers such as polyethylene oxides, polyoxyethylene-polyoxypropylene copolymers and polyvinylalcohol; cellulosic polymers such as hydroxy-propyl cellulose, hydroxyethyl cellulose, hydroxypropyl methylcellulose, hydroxy-propyl methylcellulose phthaiate, and methylcellulose; gums such as tragacanth and xanthan gum; sodium alginate; and gelatin, In order to prepare a uniform gel, dispersing agents such as alcohol or glycerin can be added, or the gelling agent can be dispersed by trituration, mechanical mixing or stirring, or combinations thereof. Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, PA: Mack Publishing Co., 1995), at pages 1399-1404, ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum.

Emulsifiable ointment bases, also known as absorbent ointment bases, contain little or no water and include, for example, hydroxystearin sulfate, anhydrous lanolin, and hydrophilic petrolatum.

Emulsion ointment bases are either water-in-oil (W/O) emulsions or oil-in-water (O/W) emulsions, and include, for example, acetyl alcohol, glyceryl monostearate, lanolin, and stearic acid. Preferred water-soluble ointment bases are prepared from polyethylene glycols of varying molecular weight; see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Enhancers are lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter 6 of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol niononlaurace, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents. Additional permeation enhancers will be known to those of ordinary skill in the art of topical drag delivery, and/or are described in the pertinent texts and literature. See, e.g., Percutaneous Penetration Enhancers, eds. Smith et al. (CRC Press, 1995)(incorporated herein by reference herein in its entirety).

Various other additives can be included in the compositions of the present invention in addition to those identified above. These include, but are not limited to, antioxidants, astringents, perfumes, preservatives, emollients, pigments, dyes, humectants, propellants, and sunscreen agents, as well as other classes of materials whose presence can be pharmaceutically or otherwise desirable. Typical examples of optional additives for inclusion in the formulations of the present invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylaury 1 ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), a-tocopherol (Vitamin E), $\beta$-tocopherol, $\gamma$-tocopherol, $\delta$-tocopherol, $\varepsilon$-tocopherol, $\zeta_1$-tocopherol, $Z^A$-tocopherol, $\eta$-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that can be obtained commercially under the Carbopol trademark. Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Further additional active agents including, for example, alpha hydroxyacids, alpha ketoacids, polymeric hydroxyacids, moisturizers, collagen, marine extract, and antioxidants such as ascorbic acid (Vitamin C), a-tocopherol (Vitamin E), $\beta$-tocopherol, $\gamma$-tocopherol, 6-tocopherol, $\varepsilon$-tocopherol, $\zeta_1$-tocopherol, $\zeta_2$-tocopherol, $\eta$-tocopherol, and retinol (Vitamin A), and/or pharmaceutically acceptable salts, esters, amides, or other derivatives thereof. A preferred tocopherol compound is $\alpha$-tocopherol. Additional agents include those that are capable of improving oxygen supply in skin tissue, as described, for example, in Gross, et al., WO 94/00098 and Gross, et al., WO 94/00109, both assigned to Lancaster Group AG (incorporated herein by reference in their entirety). Sunscreens and UV absorbing compounds can also be included. Non-limiting examples of such sunscreens and UV absorbing compounds include aminobenzoic acid (PABA), avobenzone, cinoxate, dioxybenzone, homosalate, menthyl anthranilate, oxtocrylene, octyl methoxycmnamate, octyl salicylate, oxybenzone, padirnate O, phenylbenzirmdazole sulfonic acid, sulisobenzone, titanium dioxide, trolamine salicylate, zinc oxide, ensulizole, meradiraate, octinoxate, octisalate, and octocrylene. See Title 21. Chapter 1. Subchapter D. Part 352. "Sunscreen drug products for over-the-counter human use" incorporated herein in its entirety. Other embodiments can include a variety of non-carcinogenic, non-irritating healing materials that facilitate treatment with the formulations of the invention. Such healing materials can include nutrients, minerals, vitamins, electrolytes, enzymes, herbs, plant extracts, glandular or animal extracts, or safe therapeutic agents that can be added to the formulation to facilitate the healing of dermal disorders.

The present invention contemplates amounts of these various additives equivalent to those conventionally used in the cosmetics field, and range, for example, from about 0.01% to about 20% of the total weight of the topical formulation.

The formulations of the invention can also include conventional additives such as opacifiers, fragrance, colorant, stabilizers, surfactants, and the like. In certain embodiments, other agents can also be added, such as antimicrobial agents, to prevent spoilage upon storage, i.e., to inhibit growth of microbes such as yeasts and molds.

Suitable antimicrobial agents for the present invention include, but are not limited to the following selected from the group consisting of the methyl and propyl esters of p-hydroxybenzoic acid (i.e., methyl and propyl paraben), sodium benzoate, sorbic acid, imidurea, and combinations thereof. In other embodiments, other agents can also be added, such as repressors and inducers, i.e., to inhibit (i.e., glycose) or induce (i.e. xylose) the production of the polypeptide of interest. Such additives can be employed provided they are compatible with and do not interfere with the function of the formulations.

The formulations can also contain irritation-mitigating additives to minimize or eliminate the possibility of skin irritation or skin damage resulting from the chemical entity to be administered, or other components of the composition.

Suitable irritation-mitigating additives include, for example: α-tocopherol; monoamine oxidase inhibitors, particularly phenyl alcohols such as 2-phenyl-1-ethanol; glycerin; salicylates; ascorbates; ionophores such as monensin; amphophilic amines; ammonium chloride; N-acetylcysteine; capsaicin; and chloroquine. The irritation-mitigating additive, if present, can be incorporated into the compositions at a concentration effective to mitigate irritation or skin damage, typically representing not more than about 20 wt. %, more typically not more than about 5 wt. %, of the formulation. Further suitable pharmacologically active agents that can be incorporated into the present formulations in certain embodiments and thus topically applied along with the active agent include, but are not limited to, the following: agents that improve or eradicate pigmented or non-pigmented age spots, keratoses, and wrinkles; antimicrobial agents; antibacterial agents; antipruritic and antixerotic agents; anti-inflammatory agents; local anesthetics and analgesics; corticosteroids; retinoids; vitamins; hormones; and antimetabolites. Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycmnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil. A cream, lotion, gel, ointment, paste or the like can be spread on the affected surface and gently rubbed in. A solution can be applied in the same way, but more typically will be applied with a dropper, swab, or the like, and carefully applied to the affected areas.

The application regimen will depend on a number of factors that can readily be determined, such as the severity of the condition and its responsiveness to initial treatment, but will normally not involve more than one application per day. One of ordinary skill can readily determine the optimum amount of the formulation to be administered, administration methodologies and repetition rates. In general, it is contemplated that the formulations of the invention will be applied in the range of once or twice weekly up to once daily.

III. Methods and Kits of the Invention

Methods of Treatment

The invention provides methods for treating a skin disease, wherein the methods comprise administering to a subject in need of such treatment a genetically engineered microorganism, e.g., genetically engineered bacteria, capable of expressing a recombinant therapeutic fusion protein of the invention, thereby treating the subject. In a preferred embodiment, the disease is atopic dermatitis. In yet another preferred embodiment, the recombinant therapeutic fusion protein comprises filaggrin. In other embodiments, the recombinant therapeutic fusion protein comprises filaggrin operably linked to a cell penetrating peptide. In further embodiments, the recombinant therapeutic fusion protein is operably linked to an export signal.

Kits

The present invention also provides kits. In one aspect, a kit of the invention comprises (a) a composition of the invention and (b) instructions for use thereof. In another aspect, a kit of the invention comprises (a) any one of the live biotherapeutic compositions of the invention, and (b) instructions for use thereof. Instructions can include an explanation of how to apply, administer, use, and maintain the compositions. The compositions of the invention are described supra. In some embodiments, a composition of the invention is an engineered microorganism capable of expressing therapeutically relevant recombinant fusion polypeptides, as described supra. In preferred embodiments, the composition comprises engineered bacteria (e.g., *S. epidermidis*) capable of expressing a recombinant fusion polypeptide comprising filaggrin.

In some embodiments, a kit can include a sealed container. Non-limiting examples of containers include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. Other examples of containers include glass or plastic vials or bottles. The kit and/or container can include indicia on its surface. The indicia, for example, can be a word, a phrase, an abbreviation, a picture, or a symbol.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Example 1: Development of a Nucleic Acid Construct that can Encode a Protein Capable of being Exported Out of the S. epidermidis Cell and then Imported into Human Keratinocytes The invention describes in one embodiment the generation of a recombinant S. epidermidis strains that is capable of heterologous protein secretion, therefore overcoming the intractability of genetic modification of S. epidermidis. Functional genetic analyses of the common skin colonizers S. aureus and S. epidermidis have previously been limited due to the presence of Type I and IV restriction systems in virtually all strains of these bacteria. These restriction systems recognize methylated cytosine bases in DNA from standard clone expansion systems such as DH10B E. coli. However, using a methylation deficient E. coli strain, DC10B, several constructs have been created in S. epidermidis strain ATCC122285, which is a commensal, non-pathogenic isolate lacking ica operons implicated in S. epidermidis-associated catheter bloodstream infections. Accordingly, the invention describes the first known reported heterologous protein expression in S. epidermidis. The present invention thus provides, in one embodiment, a nucleic acid plasmid capable of encoding a protein that is exported out of the S. epidermidis cell and subsequently imported into human keratinocytes. This plasmid, pAZT, is based on pJB38 (Bose, J. L., et al. Applied and environmental microbiology. 2013; 79(7):2218-2224), an allelic exchange E. coli-staphylococcal shuttle vector, which has been specifically re-engineered to possess features that improve functionality. The present invention provides, in one embodiment, an engineered S. epidermidis capable of effectively colonizing reconstituted epidermis and that is capable of producing 50 μg of protein per mL of ~$10^9$ CFU/mL (FIG. 2).

Cell Penetrating Peptides (CPP).

Despite the formidable barrier properties of the epidermis, protein delivery through the stratum corneum has been demonstrated by employing transduction peptides or cell penetrating peptides (CPP). This challenge arises due to the diffusion impediments from the hydrophobic surface and the layers of linked corneocytes comprising the stratum corneum. However, by attaching a CPP sequence to the N-terminal end of a protein of interest, successful delivery of the fusion protein into the deeper epidermis is possible, in addition to the facilitation of intracellular localization and endosomal/lysosomal escape of the target protein. The present invention, in one embodiment, provides a construct that utilizes such an approach, and comprises an HIV transactivator of a transcription-derived cell-penetration peptide (RMR) protein motif (FIG. 2). This approach is foundational to delivering protein into deeper layers of the skin for higher therapeutic effect.

Safety and "Kill Switches"

A key requirement for nearly all recombinant microorganisms for clinical use is the ability to prevent undesired introduction to other individuals or environments. In order to ensure safety of the engineered strain, the present invention, in one embodiment, uses an auxotrophic strain, which requires supplementation of key amino acids (D-ala) or a certain metabolic gene (AlaR) for survival, and simultaneously replaces the need for an antibiotic resistant strain for selection, the latter of which is not commercially viable. In another embodiment, the present invention integrates a "kill switch", which is based on CRISPR/Cas9 self-cleavage upon induction of a dual xylose-riboswitch promoter. In yet another embodiment, the present invention provides cell counters, which recombine out the AZT locus after a defined number of divisions, although this method would necessitate reapplication of the vehicle. To ensure the safety of the engineered S. epidermidis of the present invention, a CRISPR/Cas9-based kill switch, which is xylose-inducible and doubly regulated with a theophylline riboswitch, was developed. The basis of this approach is that Cas9 is extremely efficient at chromosomal cleavage given a targeting guide, and since staphylococci lack canonical nonhomologous end joining repair pathways, genomic cleavage results in death in the absence of a homologous recombination template. The use of a CRISPR-based system also confers great specificity, since comparative genomics can be used to design guides unique to the engineered S. epidermidis strain of the present invention, such that the construct is inactive if spread to other microbes by horizontal gene transfer. Finally, in one embodiment, the present invention provides a construct designed to express multiple CRISPR spacers to simultaneously target multiple genomic regions to ensure cleavage and minimize survival by reversion.

Example 2: Determine the Persistence and Localization of Topically Applied S. epidermidis Using In Vitro Model Systems

Materials and Methods

Create Reporter Bacteria.

In order to facilitate tracking of the topically applied bacteria, an sGFP-expressing strain of S. epidermidis (SE) was employed. The SecA and RMR peptides was removed such that the sGFP protein was not shuttled to the secretion system and free sGFP did not penetrate the stratum corneum. This construct is referred to as SE-sGFP.

Quantify and Compare Growth Characteristics of Transformed Bacteria in Liquid Media A basic understanding of the ability of transformed (recombinant) S. epidermidis to compete against wild type S. epidermidis was required. In order to understand the growth characteristics of the transformed bacteria and the growth dynamics of recombinant, protein-producing bacteria, standard techniques were used to quantify colony forming units (CFU) in liquid media. In order to determine growth differences between S. epidermidis-sGFP, S. epidermidis-chl and wild-type S. epidermidis, each strain was grown separately in two triplicate 100 mL cultures each for 12 hours. Every hour, a 1 mL sample was taken and measured at 395 nm and 600 nm to obtain measurements of both the signal of sGFP and the total concentration of bacteria, respectively. Fluorescence and optical density were compared across all samples to understand growth characteristics and sGFP production. The results indicated that protein production only slightly diminished the competitive growth of *S. epidermidis*-GFP relative to *S. epidermidis*-Chl as determined by fluorescence and CFU measurements.

Quantification of the Growth of *S. epidermidis*-GFP and Control Strains on RHE.

In order to characterize the feasibility of applying bacteria to the skin, the growth dynamics of externally applied bacteria on an in vitro skin model was determined, with the understanding that this is only a first approximation of the ecological competition these bacteria would encounter on the skin of a human. Assays began two days after receiving the differentiated culture, in order to allow the culture to achieve stability after shipment. RHE cultures were established and maintained in antibiotic- and antifungal-free media (supplemented with Chl as needed) that were replaced every two days. Bacteria suspended in 50% glycerol were applied with a pipette to the center 3 mm diameter of the RHE. Control RHE with *S. epidermidis*-chl and *S. epidermidis*-WT bacteria were also applied and removed alongside the experimental arms. Upon removal from culture, the tissue inserts were homogenized and passed through a 5 μm filter to allow for collection of bacteria flow through. The bacterial suspensions were spun down, resuspended in media, and serially diluted and plated to determine the CFUs of bacteria in the insert. All measurements were normalized by the maximum recovery of bacteria as determined by the CFUs recovered 15 minutes after application.

Qualitative Characterization of the Growth of SE-GFP and Control Strains on RHE.

Figures 3A, 3B, 3C, 3D:
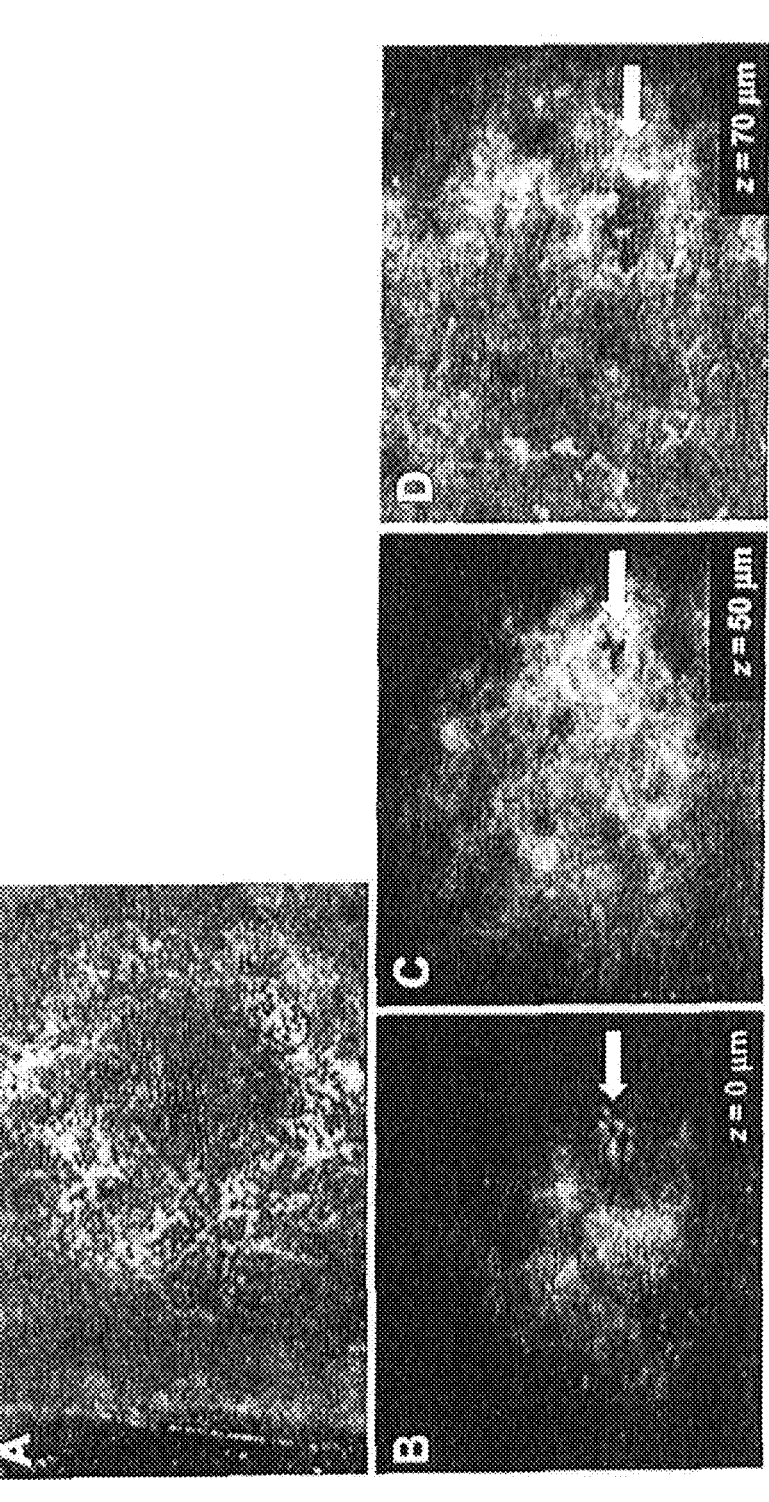
FIG. 3A-3D depicts the characterization of GFP-producing *Staphylococcus epidermidis* in reconstituted human epidermis (RHE).

Assays were designed to obtain spatial and temporal information about *S. epidermidis*-GFP colonization using RHE and the VIVASCOPE®. *S. epidermidis*-GFP was applied to RHE, and samples were imaged in reflectance and fluorescence modes in three standardized regions 2 mm×2 mm wide and 100 μm deep using 10 μm steps and linear increase in laser power. Ultrasound gel (PARKER® Laboratories) was used to preserve the refractive index between the objective and the glass sample plate. Images were analyzed in ImageJ using 'Grid/Collection Stitching' (FIG. 3).

The results indicated that bacteria home to the surface and deep grooves of the stratum corneum layer and are maintained at a constant presence over the course of the experiment.

Importantly, in order to mimic the hyperstructure of damaged skin in atopic dermatitis patients, the RHE was intentionally punctured with a Derma Microneedle device to determine localization of the bacteria in the presence of damaged skin. The results indicated that the bacteria localized to the puncture at depths up to 70 μm (arrows, FIG. 3 (B)-(D)). This suggests that the topically applied bacteria are able to hone to areas of damaged skin.

Figures 4A, 4B, 4C, 4D, 4E:
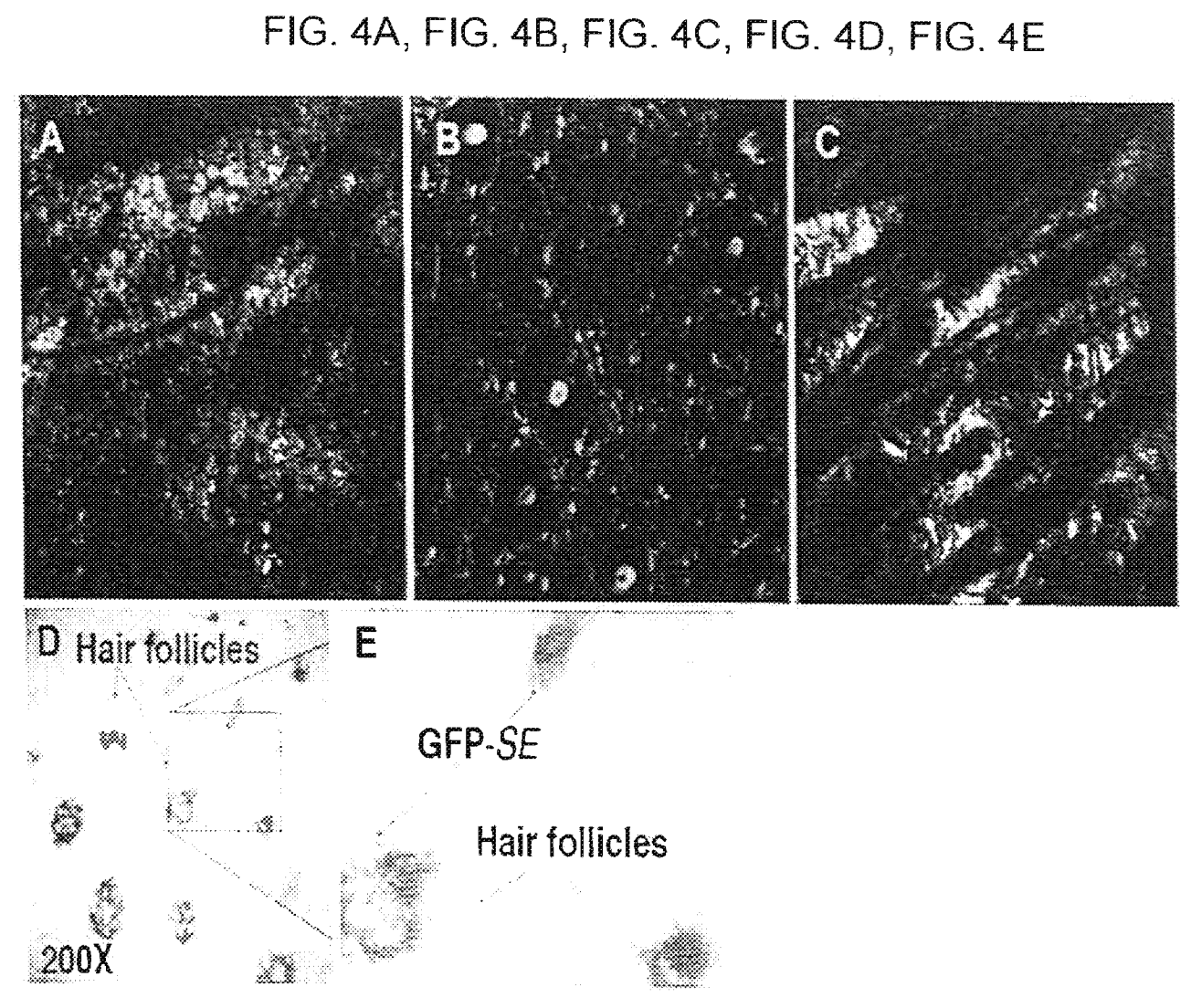

These studies were repeated in vivo. Specifically, SE-GFP was applied, to which light and in vivo two-photon microscopy was performed three days following application. At different depths, ranging from 25 μm in the mouse ear to 80 μm in shaved mouse dorsal skin (FIG. 4), the results indicated that there was sustained and pervasive GFP expression, demonstrating *S. epidermidis*-GFP's ability to colonize to the deepest layers of the stratum corneum (10-40 μm), and further colonize the hair follicles of the mice.

Example 3: The Characterization of the Delivery of Bacterially Secreted sGFP to the Skin Using an In Vitro Model System Characterization of the Production of sGFP in SE.

Characterization of the delivery of bulk purified sGFP and sGFP+RMR to RHE.

Data regarding the localization of purified sGFP and sGFP+RMR would facilitate an understanding of: (i) whether sGFP+RMR penetrates the stratum corneum; (ii) if there is penetration, how deeply the penetration can be detected; and; (iii) the kinetic characteristics of penetration. Here, 5.0 μg/μL of GFP+/−RMR was applied at time points 0, 2, 6, 12, 18, and 24 hours to determine the effect of dosage on the penetration and time. The results indicated that GFP was detected as deep as the epidermal-dermal junction within 30 minutes after application.

Figures 5A, 5B, 5C, 5D:
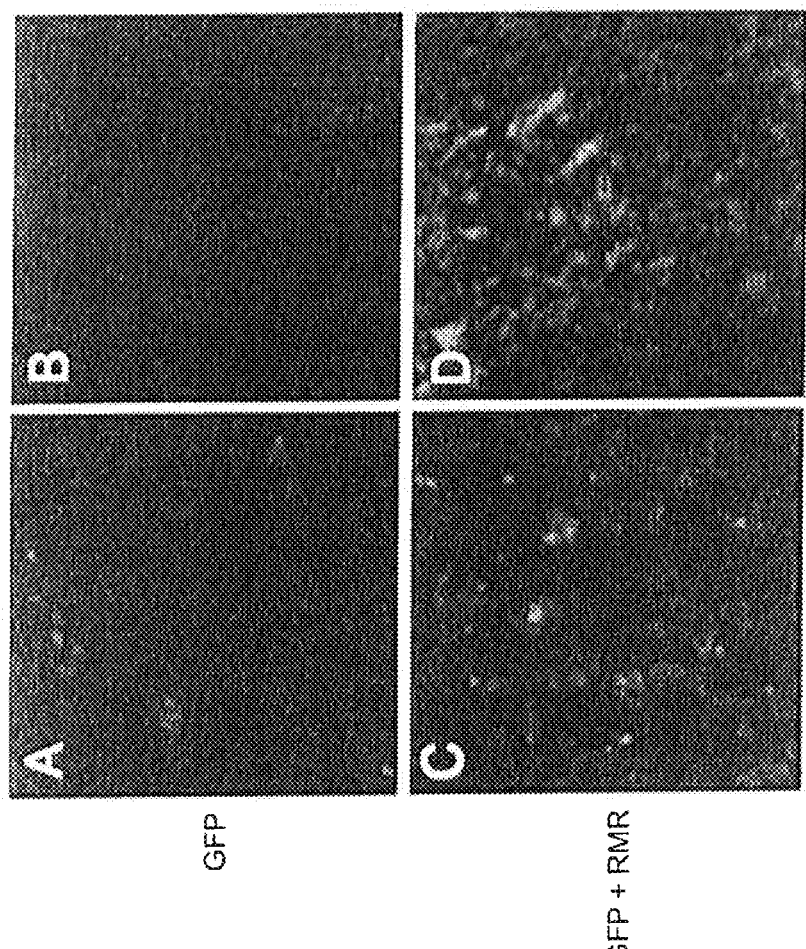
Figures 5E, 5F, 5G, 5H:
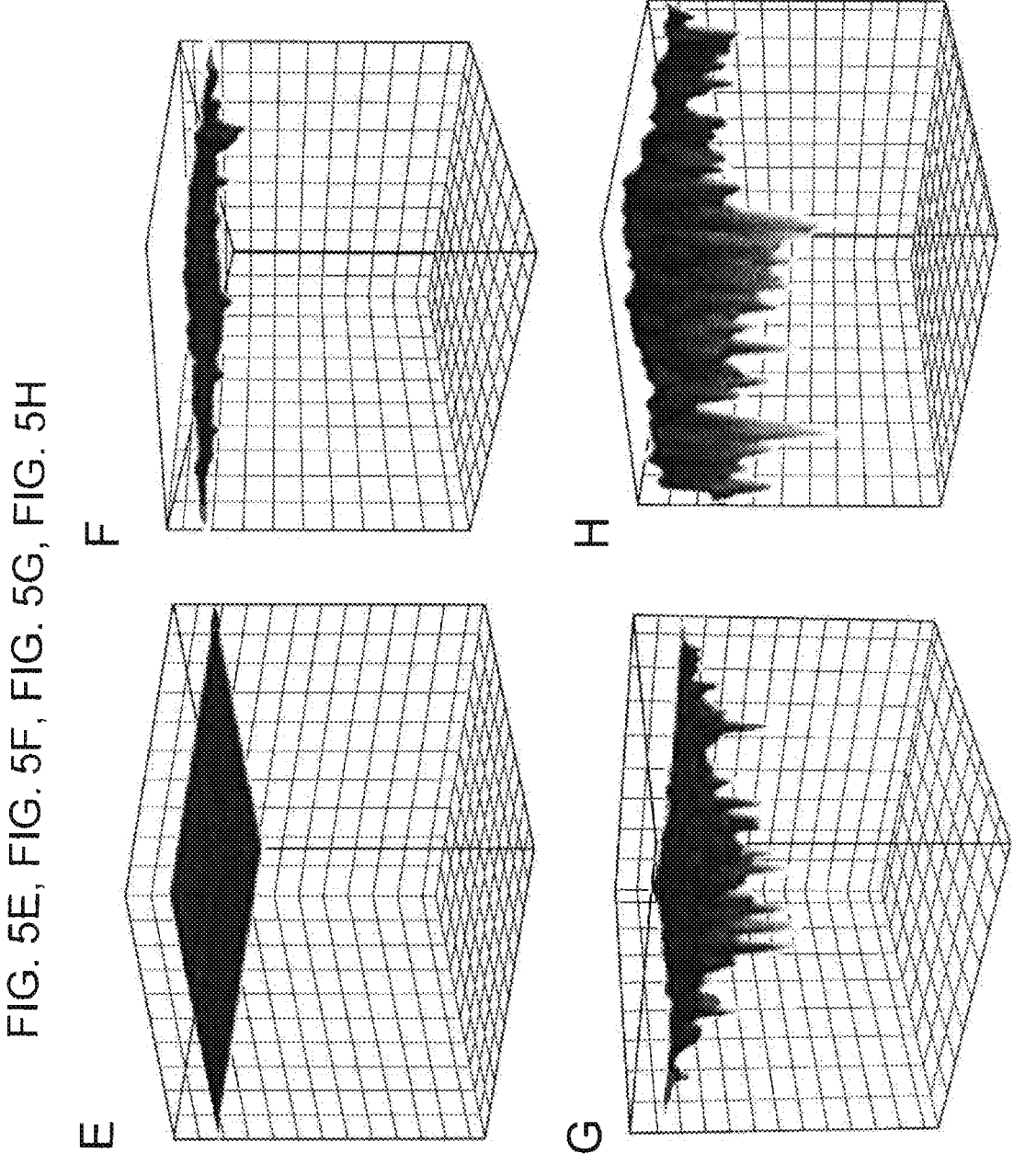
(FIG. 5E-FIG. 5H) 3D surface analysis to examine depth of protein penetration into the RHE.
Figures 5I, 5J, 5K, 5L, 5M, 5N:
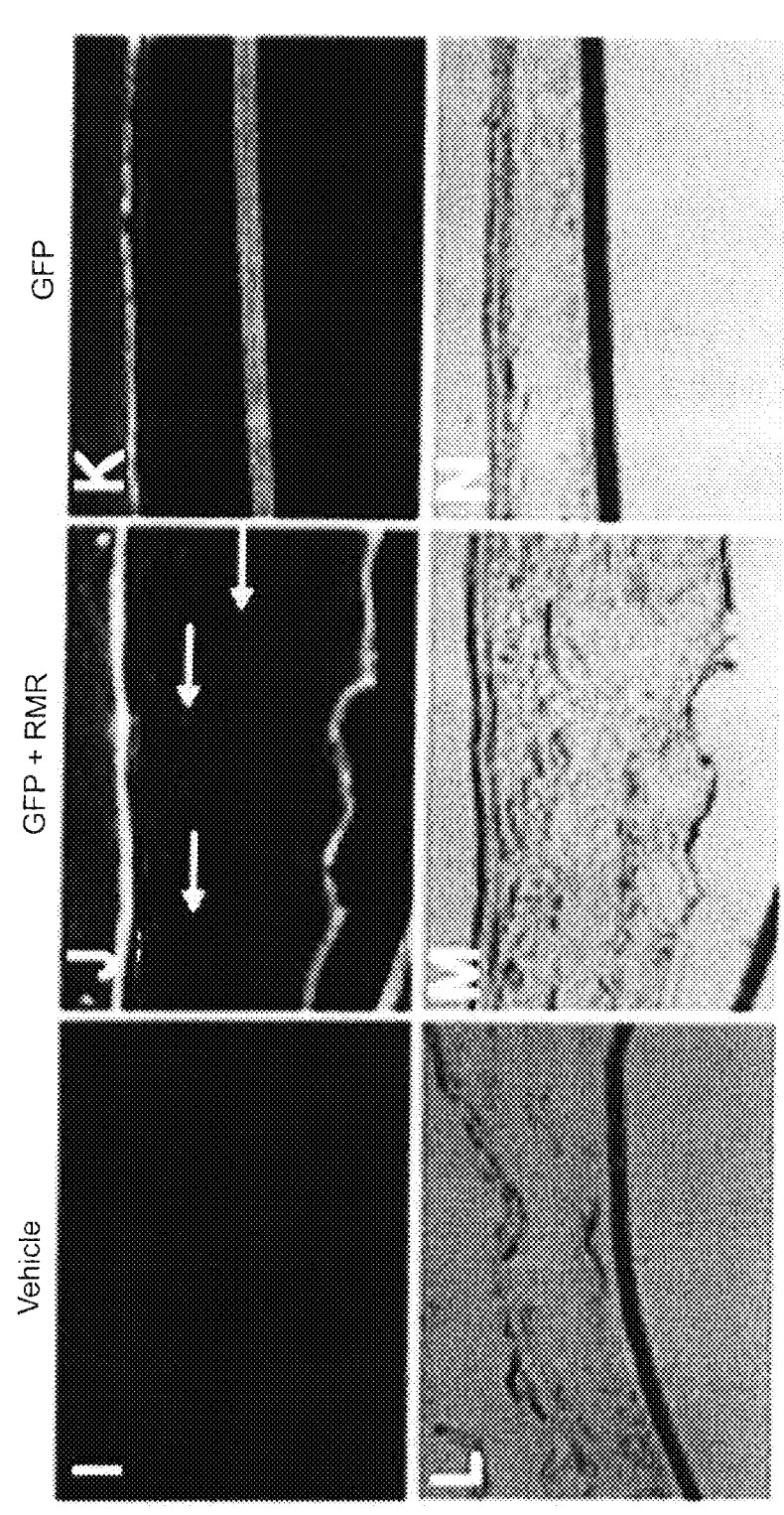

Characterization of the Cellular Compartment and Depth of Penetration of In Situ Secreted sGFP Protein from SE-GFP Reporter and Control Strains The goal of this assay is similar to that as described above, except for the critical difference that the protein is being made in situ by SE-sGFP$^{RMR/SecA}$ and SE-sGFP$^{SecA}$, and compared to controls strains on the RHE. The same methods described herein were used to characterize the dynamics of sGFP penetration into the RHE. The VIVASCOPE® provided useful information on the penetration of sGFP over larger surface areas, while the use of IHC allowed for finer discrimination. IHC methods can detect GFP-positive regions relative to SE peptidoglycan-positive regions, so that secreted sGFP can be discriminated from the sGFP signal in the bacteria. (FIG. 5)

Non-fluorescence based detection of therapeutic proteins. The therapeutic proteins ultimately delivered are not be fluorescent, and further, suitable antibodies to characterize their delivery to epidermis may not be available. Proteomic analysis of tape strips of the stratum corneum has been used to characterize differences in in vivo protein profiles from patients with atopic dermatitis (Sakabe, J., et al. *The Journal of allergy and clinical immunology*. 2014; 134(4):957-960 e958) and ichthyosis (Rice, R. H., et al. *PloS one*. 2013; 8(10):e75355). Moreover, inside-out, horizontal sections of skin biopsies may be used to demonstrate that low abundance molecules can be identified after penetrating the stratum corneum.

Example 4: Evaluate Pharmacokinetics (PK) and Pharmacodynamics (PD) of AZT-01 in Mice (Non-GLP)

A genetic atopic dermatitis mouse construct (flaky tail mice) was used to assess the PK/PD of AZT-01, while the PK of AZT-01 was assessed in healthy mice. In order to evaluate the PD, AZT-01 was topically applied to mice and the PD was assessed via phenotypic (erythema, edema, excoriation, dryness, and transepidermal water loss) and histological changes (skin barrier recapitulation, fibrosis, CD4+ T cells, etc.). To evaluate the PK, the distribution of AZT-01 and filaggrin was examined, and the colonization patterns were characterized. Changes in the skin microbiome were assessed.

Atopic dermatitis mouse models. In order to investigate the applicability of the approach, two model mouse systems were used: the filaggrin knockout mouse (fig−/−) and the flaky tail mouse (ft/ft). A thorough review of atopic dermatitis model mice is presented by Geha et. al. (Vavrova K., et al. The Journal of Invest. Dermat. 2014; 134(3):746-

753). Briefly, flg−/− mice exhibit dry, scaly skin. Despite marked decreases in natural moisturizing factor levels, which are filaggrin degradation products, stratum corneum (SC) hydration and transepidermal water loss (TEWL) were normal in flg−/− mice. Antigens penetrated the flg−/− SC more efficiently, leading to enhanced responses in hapten-induced contact hypersensitivity and higher serum levels of anti-ovalbumin IgG(1) and IgE. As such, the mouse ear was sensitized using OVA antigen.

Ft/ft mice possess two distinct autosomal recessive mutations, hair abnormality (matted: ma) and SC layer abnormality (flaky tail: ft). These mice developed dermatitis spontaneously with high serum IgE even under specific pathogen free conditions. Flaky tail mice also possess the loss of function mutation in Filaggrin (Flg) and demonstrated skin barrier abnormality as well as increased TEWL and SC hydration.

Study design. The study was conducted for four weeks using four arms in both types of mice (Flg−/− and ft/ft). Mice were randomized into the following treatment groups: topical vehicle control (50% glycerol, 50% sterilized BHI medium), topical recombinant filaggrin (purified recombinant filaggrin in 50 µg/ml), topical wild type *Staphylococcus Epidermidis* (SE) (1.0×10⁹ CFU in 50% glycerol), and topical SE$^{FLG}$ (1.0×10⁹ CFU in 50% glycerol). Each solution was applied to the same ear on each mouse on days 0, 7, 14, and 21, and mice were also assessed on these days before application of the appropriate solution. Final assessment occurred on day 28 after which point the mice was sacrificed according to the appropriate animal protocols. The primary outcome (described in detail below) is the change in clinical disease score, which assessed macroscopic changes in disease presentation.

Based on a sample size estimate using standard deviation of 2.5, power of 90%, and type I error of 0.05, 8 mice per arm per genotype was required in order to detect a mean change of 4 points in the clinical disease score between groups. This means that a total of 32 mice per genotype (for a total of 64 mice) were needed for the study.

TABLE 2

| Clinical outcome measures | | |
|---|---|---|
| Component | Values | Description |
| Primary outcome: composite clinical disease score (macroscopic observations) | | |
| Erythema | 0 to 4 | 0-not visible, 2-mild, |
| Edema | 0 to 4 | 2-moderate, 3-severe |
| Excoriation | 0 to 4 | |
| Dryness | 0 to 4 | |
| Total: | 0 to 16 | Sum of four components |
| Secondary outcomes | | |
| Infiltrated lymphocytes | Qualitative | Cell types will be indicated via histology |
| Fibrosis | 0 to 4 | 0-not visible, 2-mild, 2-moderate, 3-severe |
| TEWL | Continuous | Measured by TEWL meter |
| Skin barrier permeability | Continuous | Measured by calcein assay |

Primary outcome: Clinical disease score. In order to measure the effect of treatment on the macroscopic and microscopic changes associated with treatment of SE$^{FLG}$, a clinical score based on previous studies was used (see, e.g., Matsuoka H., et al. Allergy. 2003; 58(2):139-145, and Kim, M. C., et al. Journal of acupuncture and meridian studies. 2013; 6(2):98-109). The composite clinical disease score is the sum of the degree of severity of erythema, edema, excoriation and dryness on the ear surface was scored as 0 (not visible), 1 (mild), 2 (moderate) and 3 (severe), accordingly. Scoring was performed by individual who was blinded to treatment status of each group. Skin was photographed every 7 days. Additionally, TEWL was measured by a TEWL meter (Khazaka Electronic). Finally, the methods described in Kawasaki (i.e., Kawasaki, H. et al. *The Journal of allergy and clinical immunology.* 2012; 129(6):1538-1546.e1536) were used to assess the resolution of the skin barrier and its ability to prevent the permeation of foreign material past the stratum corneum (SC). Calcein Bis[N, Nbis(carboxymethyl)aminomethyl]fluorescein (SIGMA-ALDRICH®) was mixed with liposome prepared from Presome CSII-101 (Nippon Fine Chemical, Osaka, Japan) and topically applied to regions of the 6- to 8-week-old mice for 3 hours. The tails were then removed and rapidly freeze embedded.

Figure 6:
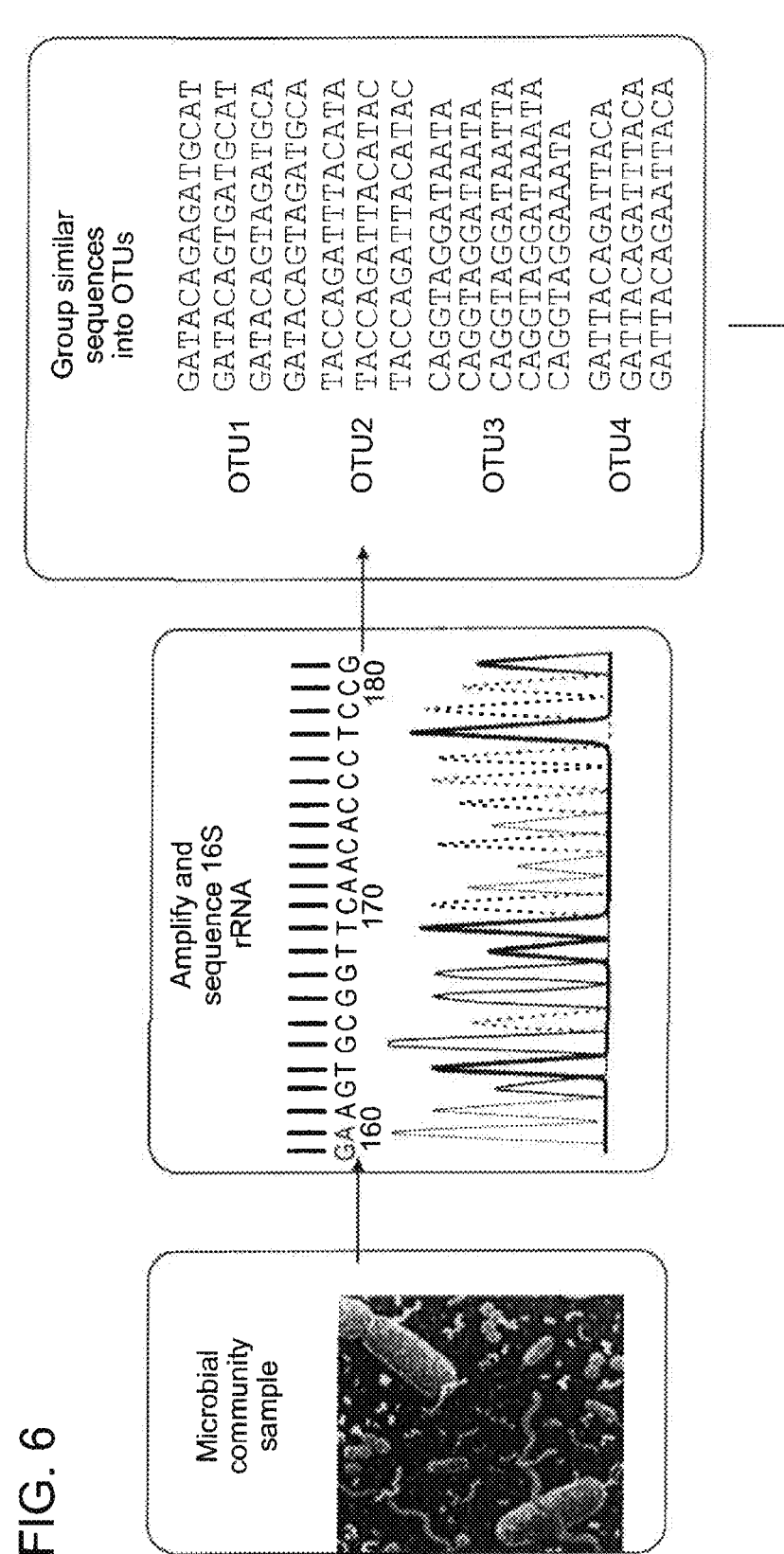
FIG. 6 depicts the experimental outline of 16S rRNA sequencing.
Figure 6:
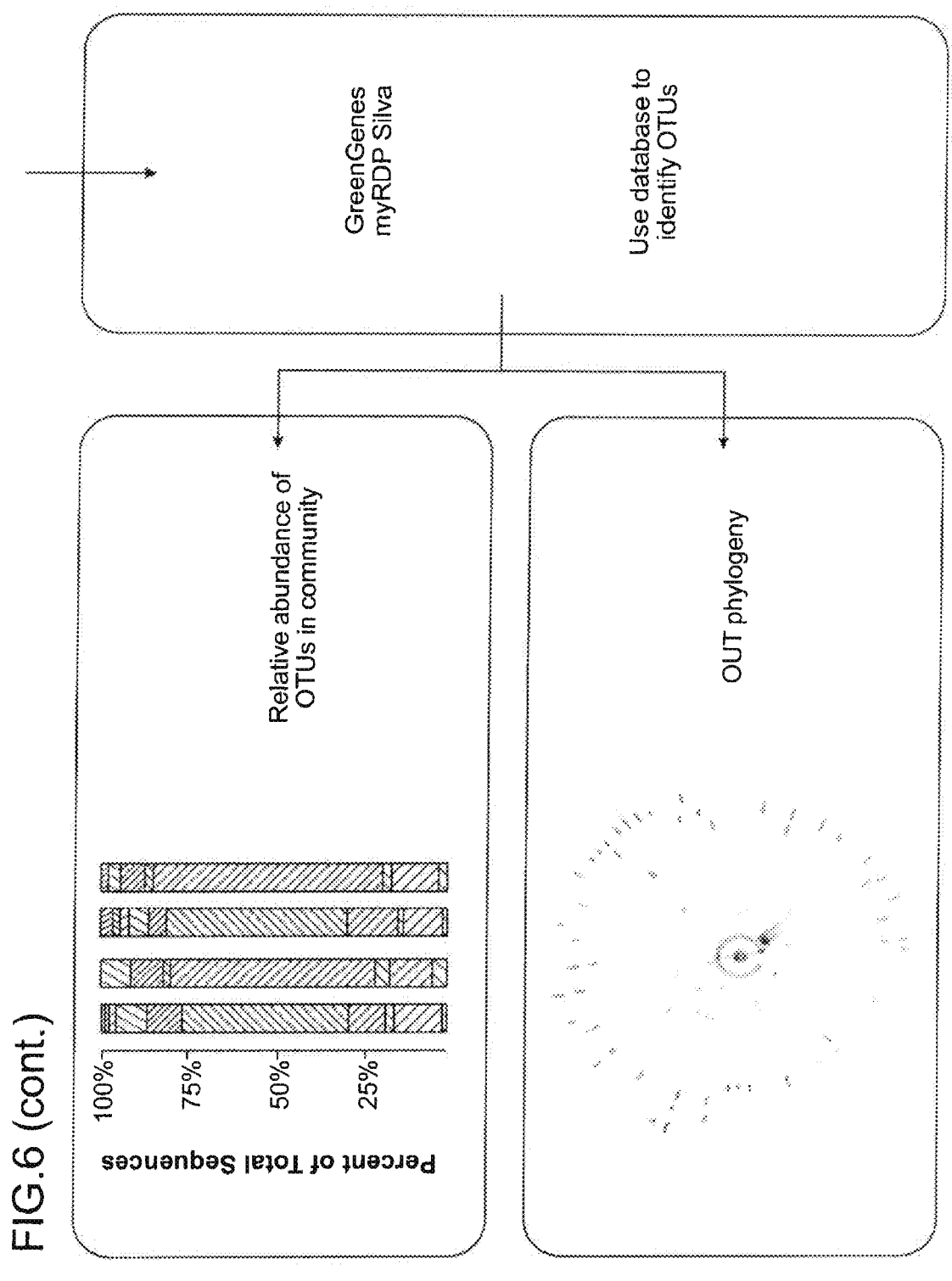

Microbiome characterization after application of AZT-01. In order to understand the influence of the addition of SE on the microbial diversity of the skin microbiome, a combined 16S rRNA was used to measure the changes in the microbial community. This was done using qPCR for RT-PCR and sequencing using the ILLUMINA® MISEQ® platform at the JAX® Genomic Medicine Facility at THE JACKSON LABORATORY®. The methods described in Caporaso et al. (Caporaso, J. G., et al. *The ISME journal.* 2012; 6(8): 1621-1624) were used to measure the changes in relative abundance of bacteria in the community. Briefly, samples were collected from the skin using cotton swabs and the rRNA was extracted using an rRNA extraction kit (QIAGEN®), which was then amplified, analyzed with qPCR and sequenced. Subsequently, bioinformatic and statistical methods were used to group similar sequences into operational taxonomic units (OTUs) (FIG. 6).

Dysbiosis was measured using ecological metrics and community structure analyses. First, dysbiosis was assessed as a function of diversity using the Shannon Diversity Index, which is an ecological measure of microbial communities that considers before and after application. Additionally, community structures of the local microbiome was compared before and after treatment. Dysbiosis was then measured as % overall deviation from (i) the baseline microbiome, and (ii) deviation from the mean community structure across our controls using statistics such as the Yue-Clayton index that compares community structures. Finally, microbiome trends was analyzed on a per-species level. The longitudinal dynamics of each species was also tracked over the treatments, to identify whether species are being lost from the community.

Immunohistochemistry studies. Filaggrin was visualized and quantified using immunocytochemistry by comparing AZT-01 to a vehicle control. Keratinocytes cells were fixed with 70% ethanol, 50 mM glycine for 1 hour. Immunofluorescence staining was performed by incubation of anti-filaggrin primary antibody at 1:200 for 2 hours, followed by incubation with rat anti-goat rhodamine secondary antibody (THE JACKSON LABORATORY®) at 1:200 dilutions in the presence of Hoechst Stain Solution (SIGMA®). Slides were mounted with coverslips in Gel/Mount (Biomed). In addition, alternative sequences was created and tested in the place of the RMR signal (e.g., endosomal escape peptides such as those described in Appelbaum et al. 2012, incorporated by reference herein in its entirety (Appelbaum, J. S., et al. Chemistry & biology. 2012; 19(7):819-830).

Statistical analyses. The differences between groups for the primary outcome and/or the macroscopic clinical disease score, were assessed using two-sided student T-tests. The differences across groups were assessed using ANOVA. The same technique will be used for assessing the TEWL and the thickening of the epidermis. The differences in non-parametric continuous variables were assessed using Mann-Whitney U tests. Finally, the differences in ordinal variables were assessed using Chi-square tests.

For analyses of the microbiome, community variation among samples were calculated using the quantitative, taxonomy-based Canberra distance. Discriminant analysis of within-group similarity were conducted using permutational MANOVA. To determine whether skin microbial communities became more similar to one another, we used a β-dispersion test with the betadisper function in vegan. This test is a multivariate analog of Levene's test for homogeneity of variances, and tests for a significant difference in sample heterogeneity between groups (Anderson, M. J., et al. *Ecology Letters.* 2006; 9(6):683-693). P-values for significant indicators were adjusted for multiple comparisons using Holm's correction (Holm S. *Scandinavian Journal of Statistics.* 1979; 6(2):65-70).

Immunofluorescence Microscopy. Immunofluorescence microscopy was used to visualize filaggrin localization. Mouse skin samples were fixed in 10% formalin and paraffin embedded. Paraffin sections were dewaxed and washed with 95% ethanol followed by methanol hydrogen peroxide. The sections were then treated with a heat induced epitope retrieval (HIER) procedure using rodent Decloaker solution (BIOCARE® Medical, RD913) and the BIOCARE® decloaking chamber. After being washed in Tris pH 7.4, sections were incubated in the presence of rat serum and FcBlock (24G2) followed by rabbit anti-*Escherichia coli* B (DAKO®, B0357) diluted in the blocking solution. Samples were washed in Tris and then incubated with goat anti-rabbit IgG-Texas Red antibody (INVITROGEN®, T2767). The tissue was then counterstained with HOECSHT, and imaged using a LEICA® DM IRBE fluorescent microscope.

Example 5: AZT-01 and its Effects on Local and Systemic Inflammation and Immunity in Rats (Non-GLP)

To evaluate toxicology, local tissue samples, serum samples, and lymph node samples of euthanized topically treated rats at specified time points were analyzed. The tissues were analyzed for histologic changes in inflammatory activity (e.g., quantification CD4+ T cells, Langerhans cells, IgE, IL-4, IFN-7, etc.) as well as activity and changes in the cutaneous immune response (e.g., quantitation of IL-4, IL-10, IL-13, etc.). Clinical signs of potential side effects related to the use of therapy including erythema, skin temperature changes, edema, blistering, and ulcerations were also monitored.

Histological evaluation. Excised ears of each group were fixed in 4% paraformaldehyde for 16 h and were embedded in paraffin. Subsequently, 6 m sections were stained with hematoxylin (SIGMA-ALDRICH®, St Louis, MO, USA) and eosin (SIGMA-ALDRICH®, St Louis, MO, USA) (H&E). Infiltrated lymphocytes and fibrosis in the dermis were observed by microscope (100×, 200×).

Disease-relevant mRNA transcript quantification. Variable expression of genes associated with atopic dermatitis development, progression, and maintenance (AD-associated pathogenic cytokines (e.g., IL-4, IL-5, IL-13, INF-7, IL-17, IL-10 and TNF-α)) were measured by standard qPCR assays. Briefly, total RNA from the skin samples were isolated using the QIAGEN® RNEASY® Mini Kit (QIAGEN®, Valencia, CA) following the manufacturer's instructions. The respective cDNA were synthesized using reverse transcriptase PCR (RT-PCR). Real-time PCR was performed using the comparative 2-AACT method and was normalized to Glyceraldehyde 3-phosphate dehydrogenase (GAPDH) transcript levels.

Immunological changes after application of AZT-01. Cells from areas of bacterial application as well as areas in which bacteria were not applied were isolated to study immunological changes. Keratinocytes, epidermal cells, cells from the lymph nodes, and small intestine lamina propria were isolated. Single cell suspensions were stained with either LIVE/DEAD Fixable Blue Dead Cell Stain Kit (INVITROGEN®) or with 4', 6-diamidino-2-phenylindol (DAPI, SIGMA®) in HBSS to exclude dead cells. For detection of transcription factors, cells were stained using the Foxp3 staining set (EBIOSCIENCE®) according to the manufacturer's protocol. For detection of intracellular cytokines, cells were fixed and permeabilized with BD Cytofix/Cytoperm and stained in BECKTON DICKINSON® PERM/WASH® (BECKTON DICKINSON® Biosciences). Cells were stained with the following antibodies purchased from either EBIOSCIENCE®, BECKTON DICKINSON® Biosciences, or Dendritics Ccorp: CD4, IL-10, IL-17A, IFN-7, TNF-α, Foxp3, CD34, CD44 and/or CD25. Staining was performed in the presence of FcBlock (EBIOSCIENCE®), 0.2 mg/ml purified rat IgG and 1 mg/ml of normal mouse serum (Jackson Immunoresearch). Stain for skin homing markers was performed as previously described (Lopes, L. B., et al. Pharm Res. 2005; 22(5):750-757). As a measure of safety, signs of AZT-01 becoming blood-borne was monitored by taking samples of skin-draining lymph nodes (DLNs) and the spleen of one mouse after two weeks of application of AZT-01. Briefly, the mouse was placed in 70% EtOH and moved to a laminar flow hood. After 1-2 minutes in EtOH, DLNs and spleen was isolated in a 50-mL conical tube with a 70 μm strainer and was processed as separate samples. The organs were dissociated with 500 μl of sterile PBS, and 50-100 μl of cell suspension was cultured on BHI agar media.

Example 6: Conduct Initial Formulation and Analytical Method Development to Evaluate a Proposed Set of Specifications for the Active Pharmaceutical Ingredient (API) and the Drug Product (DP)

Critical to the clinical development of a live biotherapeutic product (LBP; e.g., AZT-01) is developing a useful formulation and practical analytical assays given the unique nature of LBPs as active pharmaceutical ingredient (API) or drug product (DP) over traditional small molecules. A formulation will be developed for the API to produce the DP, and analytical methods will be developed for both the API and the DP stability to establish the specifications of GMP material for clinical studies.

Statistical analyses. Unless otherwise indicated, experiments were performed in triplicates, and means and standard deviations were be reported. For comparisons between groups, two-sided t-test or analysis of variance was used. If data were not normally distributed, the data were replaced with non-parametric equivalents (Wilcoxon-rank sum and Kruskal-Wallis tests).

Example 7: Hydrophobicity Analysis

Figure 7:
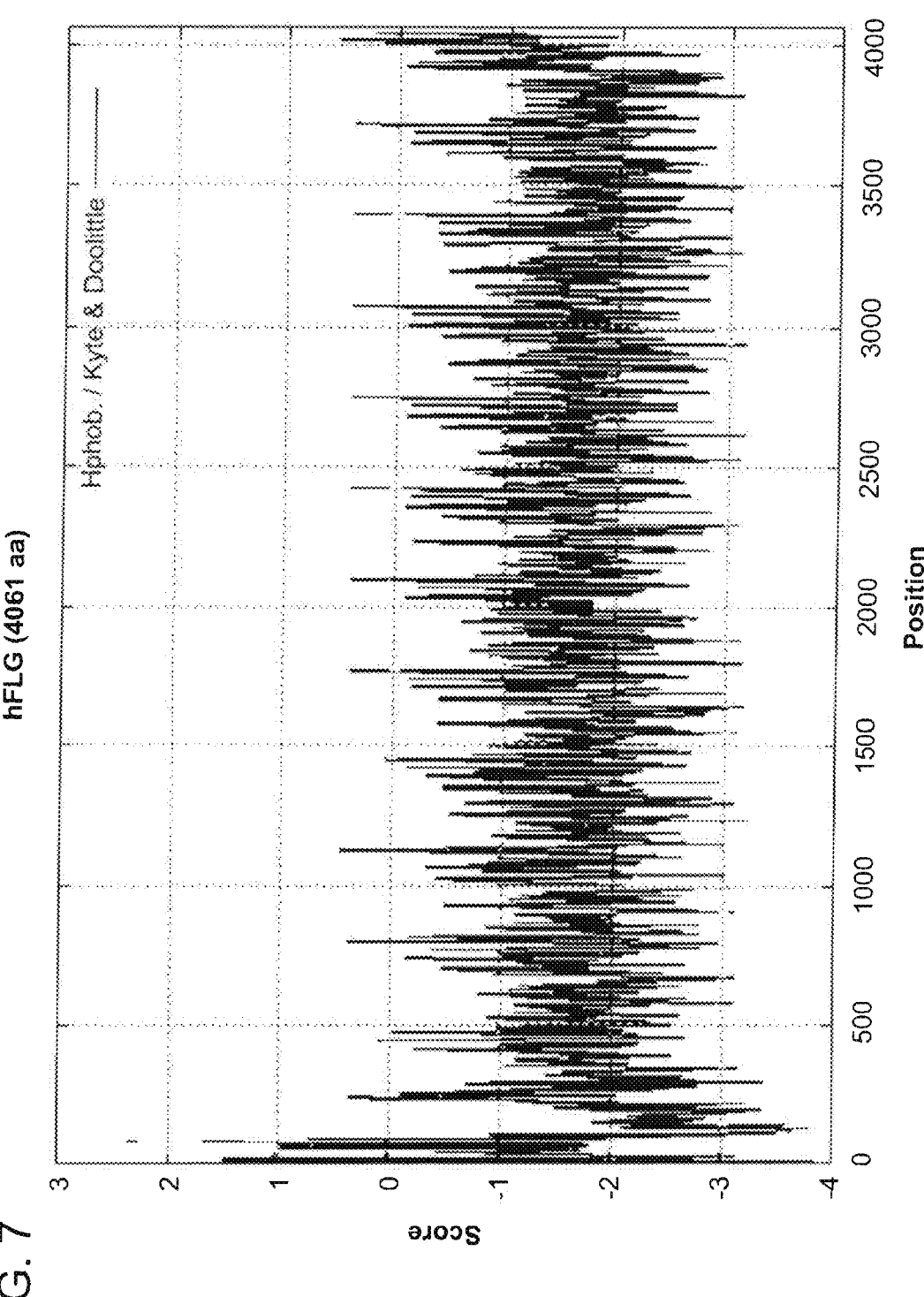
FIG. 7 is a graph that shows hydrophobicity score as a function of amino acid position for the entire human filaggrin (hFLG) sequence (Uniprot P20930).
Figure 8:
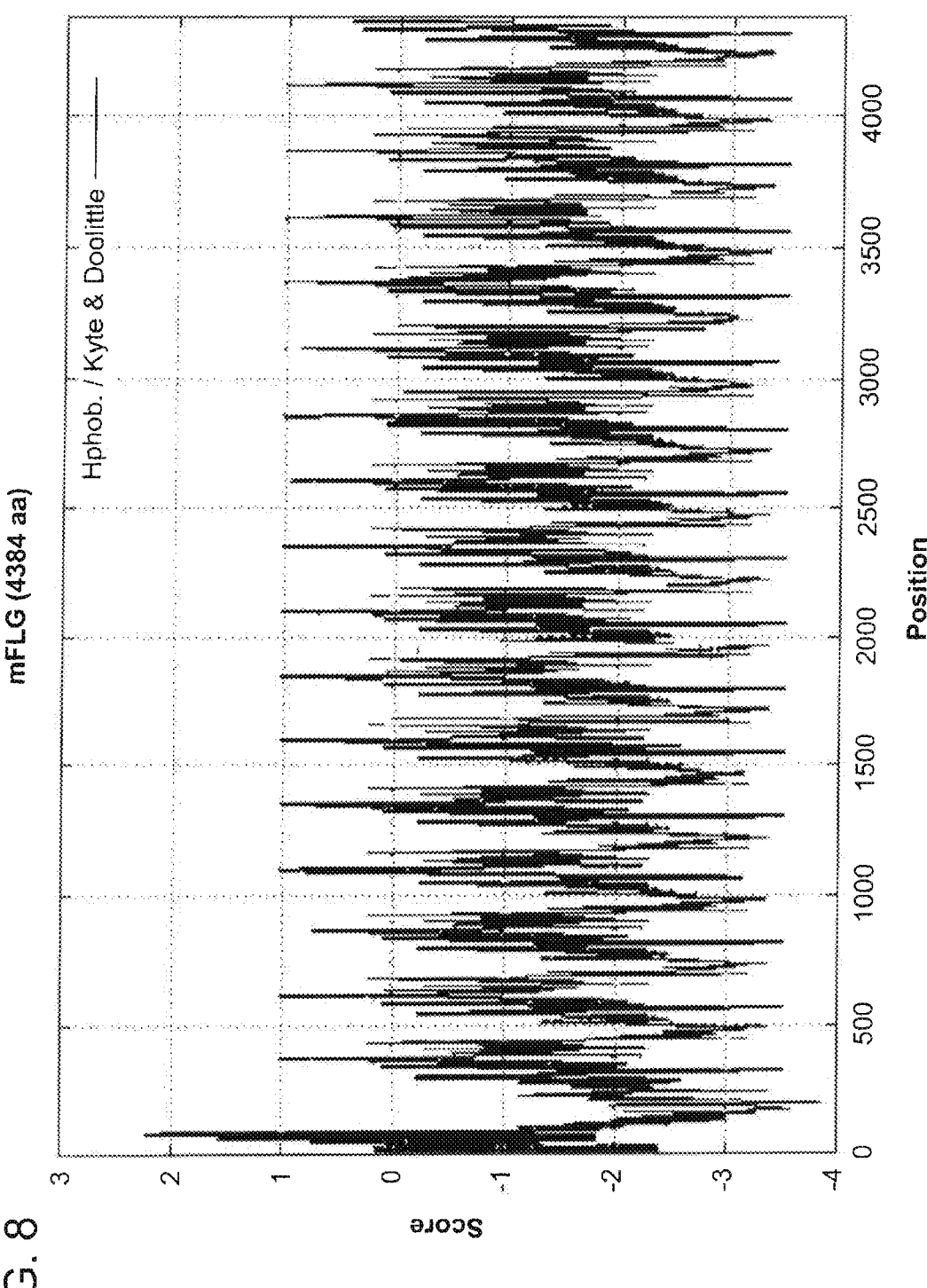
FIG. 8 is a graph that shows hydrophobicity score as a function of amino acid position for the entire mouse filaggrin (mFLG) sequence (NCBI Reference Sequence: XP_017175331.1).

Human filaggrin (hFLG) is comprised of 12 repeating units and is processed by intracellular proteases to release the individual units. The sequences within these units are highly homologous. It has been proposed that the units are cleaved at "linker regions." The segments between these linker regions are the individual units, with each unit containing a pair of sub-domains. The entire human filaggrin (hFLG) sequence (UNIPROT® P20930) was analyzed using the on-line Kite-Doolittle calculation tool. The hydrophobicity score as a function of amino acid position graph is shown in FIG. 7. As shown in FIG. 7, there is a periodic increase in hydrophobicity. The Kite-Doolittle score gave the highest differential between the highest and lowest values. When compared to the mouse filaggrin (mFLG) sequence (NCBI Reference Sequence: XP_017175331.1)

shown in FIG. 8, a much higher differential of hydrophobicity scores is seen. This is due to the nature of the proteins from the different organisms.

The molecular regions of interest were examined further. It was found that the distance between the crests which correspond to the more hydrophobic regions was farther in the human filaggrin than in the mouse. Also, the maximum hydrophobicity was found to be higher in the mouse than in human.

Figure 9:
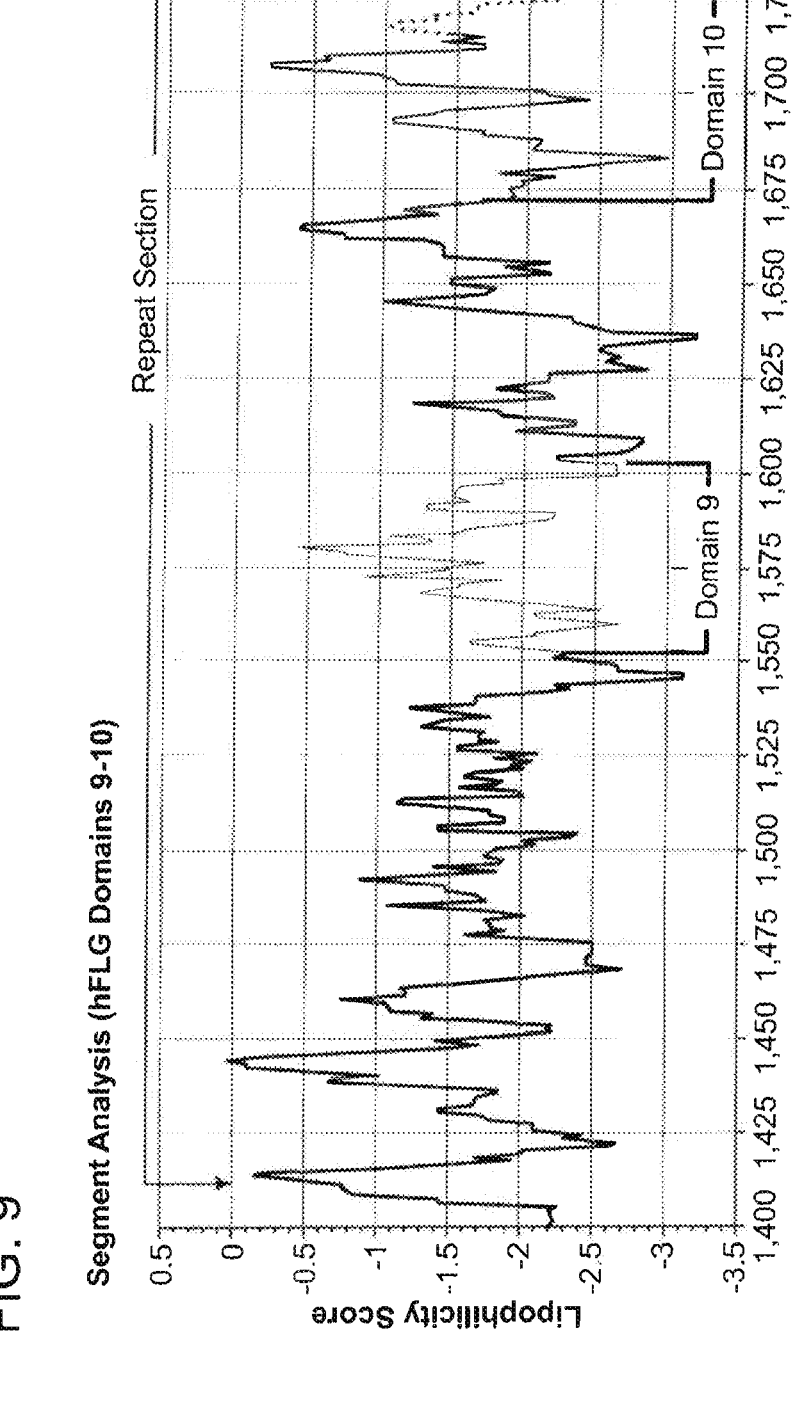
FIG. 9 is a graph that shows hydrophobicity score as a function of amino acid position for the hFLG region starting at amino acid 1400 to 1800 with the unit segment of domains 9 and 10.

Two particular domains of hFLG were of interest, hFLG [domains 5-6] and [domains 9-10]. FIG. 9 shows the region of hFLG starting at amino acid 1400 to 1800, with the unit segment of domains 9 and 10 shown. The repeat end at a peak that comes right after the 10 amino acid segment that is common to human and mouse filaggrin (SGSQASD-SEGHS) (SEQ ID NO: 25) is also shown. The high peaks at positions 1444 and 1767 of the graph correspond to the FLY segments. The peaks at 1679 and 1929 are regions containing poly-tyrosines.

Figure 10:
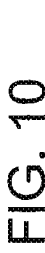
FIG. 10 is a graph that shows hydrophobicity score as a function of amino acid position for hFLG[9-10](1429-1774) from amino acid position 1400 to amino acid position 1800 in hFLG.
Figure 10:
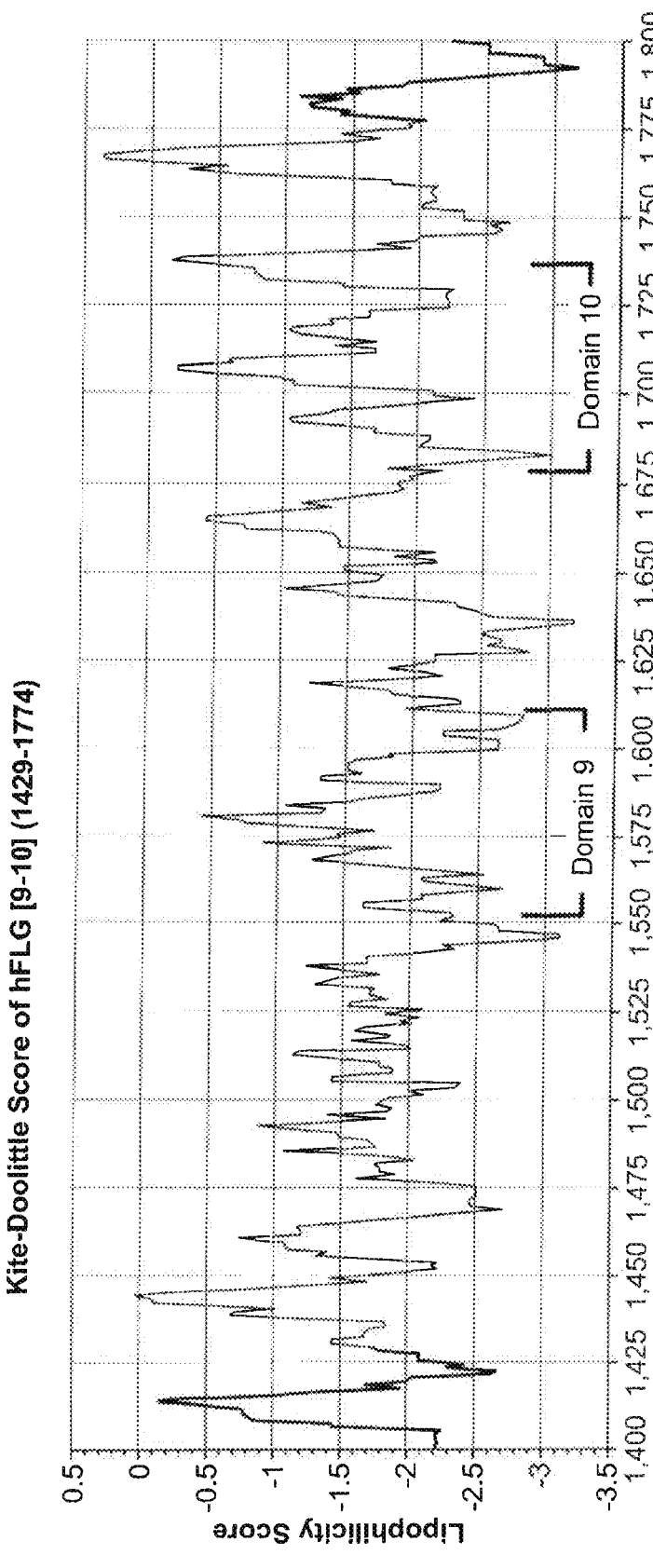

The protein hFLG (Domains 9-10) (1429-1774) (SEQ ID NO: 2) represents the high-to-high hydrophobicity segments. The segment is shown in FIG. 10. It contains the FLY segments at both ends of the protein.

```
hFLG[9-10](M-1429-1774)
                                                      SEQ ID NO: 2
                                                1430          1440
                                                  MQ SGESSGRSRS 1450       1460       1470       1480       1490       1500
  FLYQVSSHEQ SESTHGQTAP STGGRQGSRH EQARNSSRHS ASQDGQDTIR GHPGSSRGGR 1510       1520       1530       1540       1550       1560
  QGSYHEQSVD RSGHSGYHHS HTTPQGRSDA SHGQSGPRSA SRQTRNEEQS GDGSRHSGSR 1570       1580       1590       1600       1610       1620
  HHEPSTRAGS SRHSQVGQGE SAGSKTSRRQ GSSVSQDRDS EGHSEDSERR SESASRNHYG 1630       1640       1650       1660       1670       1680
  SAREQSRHGS RNPRSHQEDR ASHGHSAESS RQSGTRHAET SSGGQAASSQ EQARSSPGER 1690       1700       1710       1720       1730       1740
  HGSRHQQSAD SSTDSGTGRR QDSSVVGDSG NRGSSGSQAS DSEGHSEESD TQSVSAHGQA 1750       1760       1770       1780
  GPHQQSHQES TRGQSGERSG RSGSFLYQVS THEQ
```

The complete sequence of the protein hFLG (Domains 9-10) (1429-1774) with N-terminus methionine and an RMR segment at C-terminus is shown in SEQ ID NO: 3 (M and RMR are underlined). The repeated sequence QSGEXS-GRSXSFLYQVSXHEQSES (SEQ ID NO: 26) is shown in bold below.

```
hFLG[9-10](M-1429-1774-RMR)
                                                      SEQ ID NO: 3
                                                1430          1440
                                                  MQ SGESSGRSRS 1450       1460       1470       1480       1490       1500
  FLYQVSSHEQ SESTHGQTAP STGGRQGSRH EQARNSSRHS ASQDGQDTIR GHPGSSRGGR 1510       1520       1530       1540       1550       1560
  QGSYHEQSVD RSGHSGYHHS HTTPQGRSDA SHGQSGPRSA SRQTRNEEQS GDGSRHSGSR 1570       1580       1590       1600       1610       1620
  HHEPSTRAGS SRHSQVGQGE SAGSKTSRRQ GSSVSQDRDS EGHSEDSERR SESASRNHYG 1630       1640       1650       1660       1670       1680
  SAREQSRHGS RNPRSHQEDR ASHGHSAESS RQSGTRHAET SSGGQAASSQ EQARSSPGER 1690       1700       1710       1720       1730       1740
  HGSRHQQSAD SSTDSGTGRR QDSSVVGDSG NRGSSGSQAS DSEGHSEESD TQSVSAHGQA
```

-continued

```
      1750        1760        1770        1780
GPHQQSHQES TRGQSGERSG RSGSFLYQVS THEQRMRRMR RMRR
```

5

It was found that repeating the FLY segments may not be required for activity, and further, it may be a burden for bacteria and may be the source of the lack of production in a Gram positive organism.

FIG. 10 is a graph that shows hydrophobicity score as a function of amino acid position for hFLG[9-10](1429-1774) from amino acid position 1400 to amino acid position 1800 in hFLG.

Example 8. New Protein Structures Based on Hydrophobicity Analysis hFLG [Domains 9-10]

Figure 11:
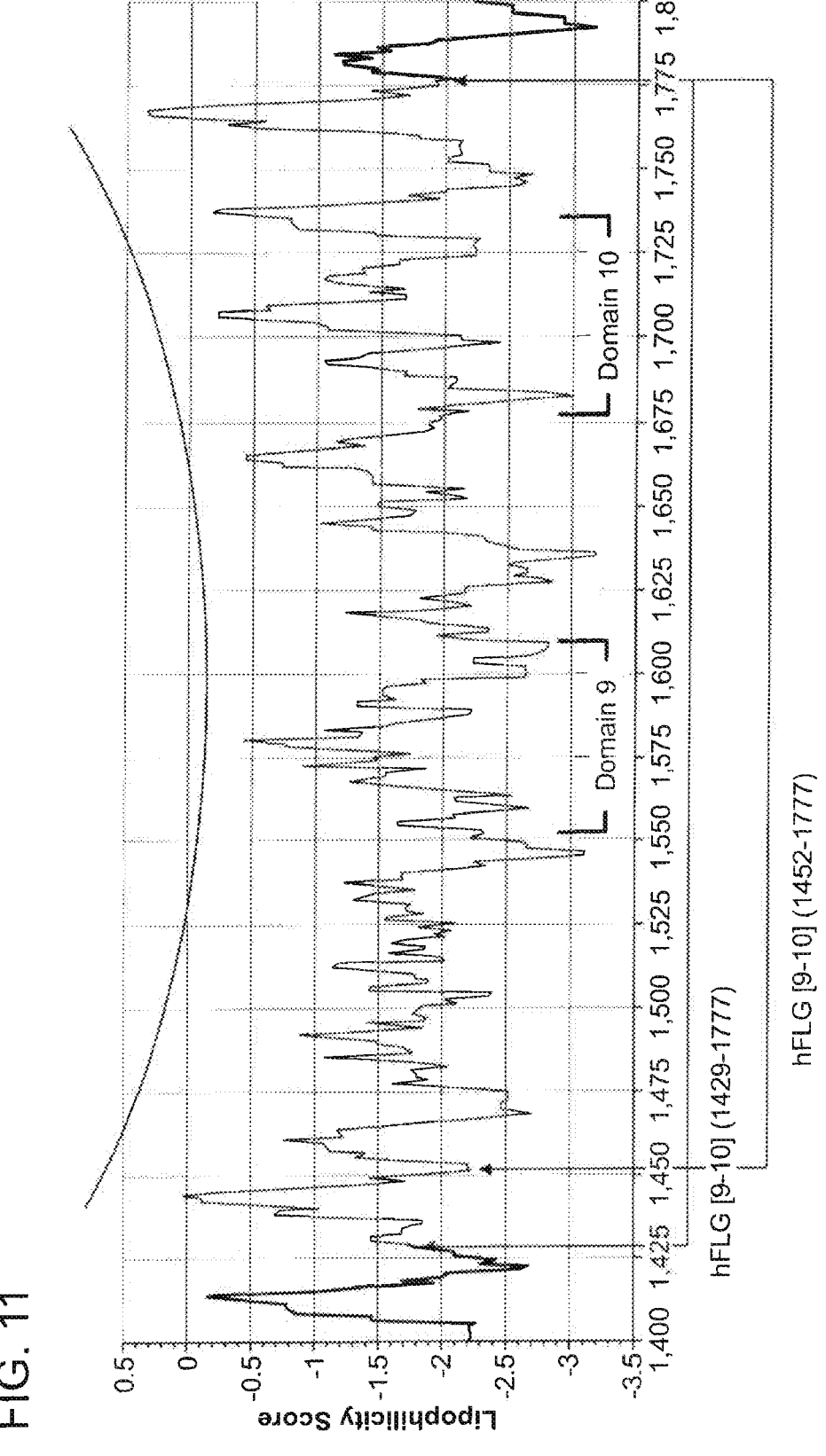
FIG. 11 is a graph that shows hydrophobicity score as a function of amino acid position for the start and end positions of the hFLG [9-10](1429-1777).

Next, hFLG [domain 9-10] proteins with systematically shaved off regions of the N-terminus were produced.
Selection of Segment Based on "U" Shape ("High-Low-High")
The graph in FIG. 11 shows that the start and end positions of the hFLG [9-10]1429-1777) (SEQ ID NO: 2) may be too long. Therefore, the N-terminal FLY segment was cut to make hFLG [9-10](1452-1777) (SEQ ID NO: 4) to prevent unwanted recombination events.

```
hFLG[9-10](1452-1777)-RMR
                                                    SEQ ID NO: 4
                   1460       1470       1480       1490       1500
            MESTHGQTAP STGGRQGSRH EQARNSSRHS ASQDGQDTIR GHPGSSRGGR 1510       1520       1530       1540       1550       1560
QGSYHEQSVD RSGHSGYHHS HTTPQGRSDA SHGQSGPRSA SRQTRNEEQS GDGSRHSGSR 1570       1580       1590       1600       1610       1620
HHEPSTRAGS SRHSQVGQGE SAGSKTSRRQ GSSVSQDRDS EGHSEDSERR SESASRNHYG 1630       1640       1650       1660       1670       1680
SAREQSRHGS RNPRSHQEDR ASHGHSAESS RQSGTRHAET SSGGQAASSQ EQARSSPGER 1690       1700       1710       1720       1730       1740
HGSRHQQSAD SSTDSGTGRR QDSSVVGDSG NRGSSGSQAS DSEGHSEESD TQSVSAHGQA 1750       1760       1770
GPHQQSHQES TRGQSGERSG RSGSFLYQVS THEQSESRMR RMRRMRR
Theoretical pl/Mw: 10.65/36162.11
```

35

Figure 12:
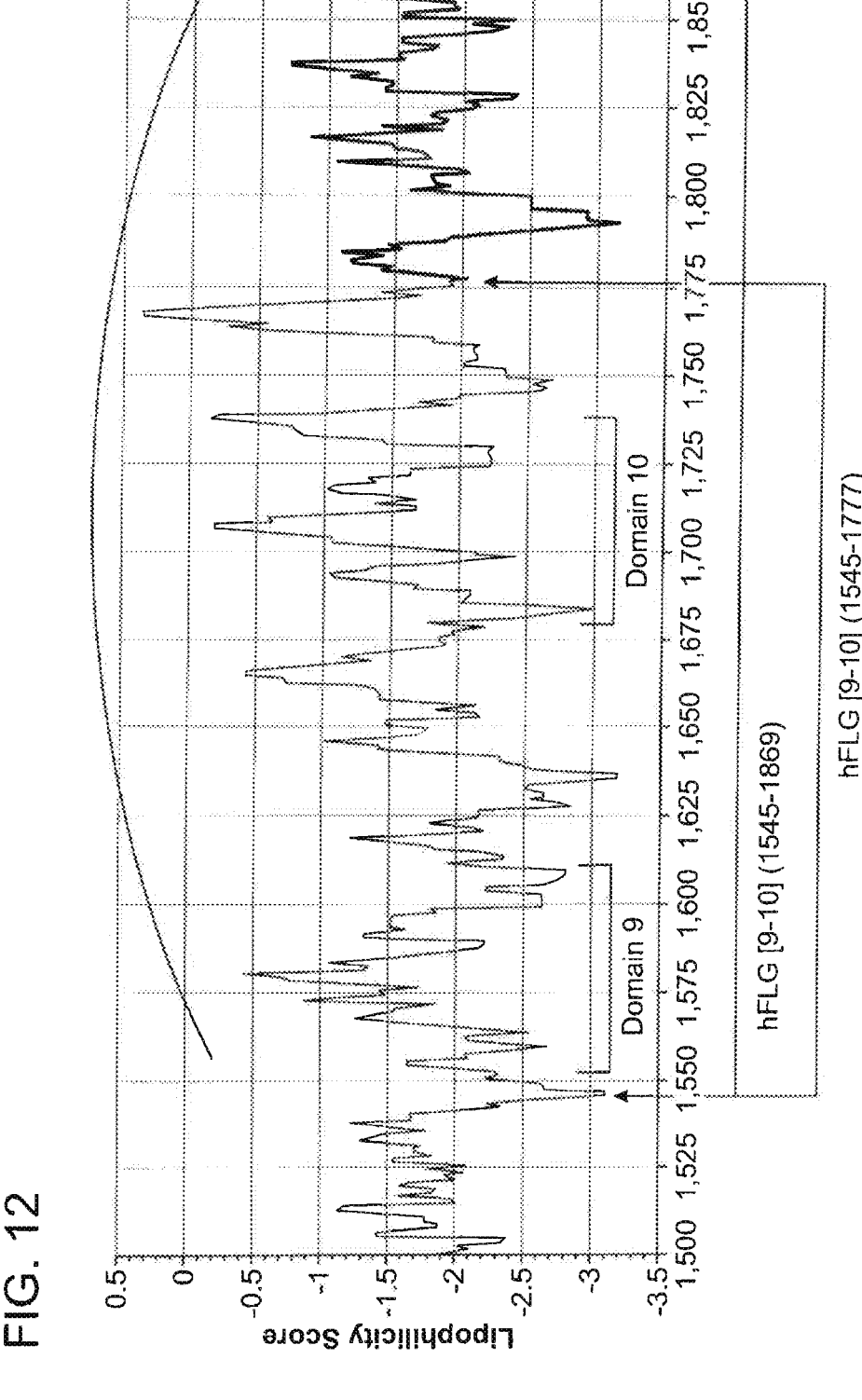
FIG. 12 is a graph that shows hydrophobicity score as a function of amino acid position from a point of low hydrophobicity to the next point of low hydrophobicity (indicated by arrows).

Selection of Segment Based on "A" Shape ("Low-High-Low")
Next, the selection of a repeat sequence from a point of low hydrophobicity to the next point of low hydrophobicity was carried out. This segment has the two domains at the N-terminus with the FLY region close to the middle of the sequence. Thus, the "core" sequence containing the domains 9-10 are at an end, rather than in the middle of the sequence. Further, the long intersection repeat sequence is toward the C-terminus of the sequence. This is shown in FIG. 12.
Based on the aforementioned analyses, a protein based on the low-to-low segment hFLG[9-10](1545-1869) was made, shown below as SEQ ID NO: 5.

```
hFLG[9-10](1545-1869)-RMR
                                                    SEQ ID NO: 5
                                           1550       1560
                                    MRNEEQS GDGSRHSGSR 1570       1580       1590       1600       1610       1620
HHEPSTRAGS SRHSQVGQGE SAGSKTSRRQ GSSVSQDRDS EGHSEDSERR SESASRNHYG 1630       1640       1650       1660       1670       1680
SAREQSRHGS RNPRSHQEDR ASHGHSAESS RQSGTRHAET SSGGQAASSQ EQARSSPGER 1690       1700       1710       1720       1730       1740
HGSRHQQSAD SSTDSGTGRR QDSSVVGDSG NRGSSGSQAS DSEGHSEESD TQSVSAHGQA 1750       1760       1770       1780       1790       1800
GPHQQSHQES TRGQSGERSG RSGSFLYQVS THEQSESAHG RTGPSTGGRQ RSRHEQARDS 1810       1820       1830       1840       1850       1860
SRHSASQEGQ DTIRGHPGSS RGGRQGSHYE QSVDSSGHSG SHHSHTTSQE RSDVSRGQSG
```

```
                             -continued
      1870
SRSVSRQTRR MRRMRRMRR
Theoretical pl/Mw: 11.00/36182.19
```

The importance of the segment that has no known function will be evaluated by removing it in hFLG[9-10](1545-1777), shown below as SEQ ID NO: 6.

```
hFLG[9-10](1545-1777)-RMR
                                                SEQ ID NO: 6
                                           1550         1560
                                         MRNEEQS GDGSRHSGSR 1570       1580       1590       1600       1610       1620
HHEPSTRAGS SRHSQVGQGE SAGSKTSRRQ GSSVSQDRDS EGHSEDSERR SESASRNHYG 1630       1640       1650       1660       1670       1680
SAREQSRHGS RNPRSHQEDR ASHGHSAESS RQSGTRHAET SSGGQAASSQ EQARSSPGER 1690       1700       1710       1720       1730       1740
HGSRHQQSAD SSTDSGTGRR QDSSVVGDSG NRGSSGSQAS DSEGHSEESD TQSVSAHGQA 1750       1760       1770
GPHQQSHQES TRGQSGERSG RSGSFLYQVS THEQSESRMR RMRRMRR
Theoretical pl/Mw: 10.07/26329.02
```

It is further contemplated that on hFLG[9-10](1452-1777) (SEQ ID NO: 2), the N-terminus region would be knocked off.

Example 9. Filaggrin (M-AZT-mutein-RMR)

The hFLG[9-10] sequence (SEQ ID NO: 1) was subjected to a BLAST analysis:
Filaggrin [*Homo sapiens*]
Sequence ID: NP 002007.1
Length: 4061 Number of Matches: 16
Range 1: 1430 to 1774

This sequence was compared to the other hFLG units (FLG[3-4], hFLG[5-6], hFLG[7-8], hFLG[11-12], hFLG [13-14], hFLG[15-16], hFLG[17-18], hFLG[19-20], hFLG [21-22]). The amino acids that were variable were compared and the most common ones were replaced into the [9-10] sequence.

The new sequence (S-FLG) was compared to the original hFLG[9-10] sequence by multiple alignment, shown below:

```
                    Alignment statistics for match #1

Score          Expect  Method          Identities      Positives       Gaps 625 bits(1611)    0.0  Compositional   345/345(100%)   345/345(100%)   0/345(0%)
                       matrix adjust.

Query      1  QSGESSGRSRSFLYQVSSHEQSESTHGQTAPSTGGRQGSRHEQARNSSRHSASQDGQDTI      60
              QSGESSGRSRSFLYQVSSHEQSESTHGQTAPSTGGRQGSRHEQARNSSRHSASQDGQDTI
Sbjct   1430  QSGESSGRSRSFLYQVSSHEQSESTHGQTAPSTGGRQGSRHEQARNSSRHSASQDGQDTI    1489

Query     61  RGHPGSSRGGRQGSYHEQSVDRSGHSGYHHSHTTPQGRSDASHGQSGPRSASRQTRNEEQ     120
              RGHPGSSRGGRQGSYHEQSVDRSGHSGYHHSHTTPQGRSDASHGQSGPRSASRQTRNEEQ
Sbjct   1490  RGHPGSSRGGRQGSYHEQSVDRSGHSGYHHSHTTPQGRSDASHGQSGPRSASRQTRNEEQ    1549

Query    121  SGDGSRHSGSRHHEPSTRAGSSRHSQVGQGESAGSKTSRRQGSSVSQDRDSEGHSEDSER     180
              SGDGSRHSGSRHHEPSTRAGSSRHSQVGQGESAGSKTSRRQGSSVSQDRDSEGHSEDSER
Sbjct   1550  SGDGSRHSGSRHHEPSTRAGSSRHSQVGQGESAGSKTSRRQGSSVSQDRDSEGHSEDSER    1609

Query    181  RSESASRNHYGSAREQSRHGSRNPRSHQEDRASHGHSAESSRQSGTRHAETSSGGQAASS     240
              RSESASRNHYGSAREQSRHGSRNPRSHQEDRASHGHSAESSRQSGTRHAETSSGGQAASS
Sbjct   1610  RSESASRNHYGSAREQSRHGSRNPRSHQEDRASHGHSAESSRQSGTRHAETSSGGQAASS    1669

Query    241  QEQARSSPGERHGSRHQQSADSSTDSGTGRRQDSSVVGDSGNRGSSGSQASDSEGHSEES     300
              QEQARSSPGERHGSRHQQSADSSTDSGTGRRQDSSVVGDSGNRGSSGSQASDSEGHSEES
Sbjct   1670  QEQARSSPGERHGSRHQQSADSSTDSGTGRRQDSSVVGDSGNRGSSGSQASDSEGHSEES    1729

Query    301  DTQSVSAHGQAGPHQQSHQESTRGQSGERSGRSGSFLYQVSTHEQ (SEQ ID NO: 27)  345
              DTQSVSAHGQAGPHQQSHQESTRGQSGERSGRSGSFLYQVSTHEQ (SEQ ID NO: 28)
Sbjct   1730  DTQSVSAHGQAGPHQQSHQESTRGQSGERSGRSGSFLYQVSTHEQ (SEQ ID NO: 27)  177
```

```
hFLG[9-10]    MQSGESSGRSRSFLYQVSSHEQSESTHGQTAPSTGGRQGSRHEQARNSSRHSASQDGQDT
S-FLG         M------RSRSFLYQVSSHEQSESTHGQTAPSTGGRQGSRHEQARNSSRHSASQDGQDT
              ************************************************************* hFLG[9-10]    IRGHPGSSRGGRQGSYHEQSVDRSGHSGYHHSHTTPQGRSDASHGQSGPRSASRQTRNEE
S-FLG         IRGHPGSSRGGRQGSYHEQSVDRSGHSGYHHSHTTPQGRSDASHGQSGPRSASRQTRNEE
              ************************************************************* hFLG[9-10]    QSGDGSRHSGSRHHEPSTRAGSSRHSQVGQGESSGSKTSRRQGSSVSQDRDSEGHSEDSE
S-FLG         QSGDGSRHSGSRHHEASTRADSSRHSQVGQGQSSGSRTSRRQGSSVSQDSDSEGHSEDSE
              *************..********:*:.********* ******* hFLG[9-10]    RRSESASRNHYGSAREQSRHGSRNPRSHQEDRASHGHSAESSRQSGTRHAETSSGGQAAS
S-FLG         RRSGSASRNHYGSAQEQSRDGSRHPRSHQEDRASHGHSAESSRQSGTRHAETSSGGQAAS
              *.******:..*:*********************************** hFLG[9-10]    SQEQARSSPGERHGSRHQQSADSSTDSGTGRRQDSSVVGDSGNRGSSGSQASDSEGHSEE
S-FLG         SHEQARSSPGERHGSRHQQSADSSRHSGIGHGQASSAVRDSGHRGSSGSQASDSEGHSED
              *:.******************** .** *: * **.* ***.***************** :

hFLG[9-10]    SDTQSVSAHGQAGPHQQSHQESTRGQSGERSGRSGSFLYQVSTHEQ---RMRRMRRMRR  (SEQ ID NO: 3)
S-FLG         SDTQSVSAHGQAGPHQQSHQESARGRSGERSGRSGSFLYQVSTHEQSESRMRRMRRMRR  (SEQ ID NO: 8)
              *********************.**:.******************   **********
``` hFLG[M-AZT-mutein-RMR](1-352) was created, shown below as SEQ ID NO: 8.

```
hFLG[M-AZT-mutein-RMR](1-352)
         10         20         30         40         50         60
MRSRSFLYQV SSHEQSESTH GQTAPSTGGR QGSRHEQARN SSRHSASQDG QDTIRGHPGS 70         80         90        100        110        120
SRGGRQGSYH EQSVDRSGHS GYHHSHTTPQ GRSDASHGQS GPRSASRQTR NEEQSGDGSR 130        140        150        160        170        180
HSGSRHHEAS TRADSSRHSQ VGQGQSSGSR TSRRQGSSVS QDSDSEGHSE DSERRSGSAS 190        200        210        220        230        240
RNHYGSAQEQ SRDGSRHPRS HQEDRASHGH SAESSRQSGT RHAETSSGGQ AASSHEQARS 250        260        270        280        290        300
SPGERHGSRH QQSADSSRHS GIGHGQASSA VRDSGHRGSS GSQASDSEGH SEDSDTQSVS 310        320        330        340        350
AHGQAGPHQQ SHQESARGRS GERSGRSGSF LYQVSTHEQS ESRMRRMRRM RR
```

The amino acids shown in bold in SEQ ID NO: 8 were modified to the most prevalent amino acid when comparing every FLG unit. Table 3 below shows the amino acid residue in hFLG[9-10] and the corresponding modified amino acid in hFLG[AZT-mutein]. The Ser-Glu-Ser (SES) was re-introduced in the sequence to align with the Kite-Doolittle analysis. The QSGESSG (SEQ ID NO: 9) sequence was removed for the same reason as the SES and was calculated to be frivolous.

TABLE 3

| Position | Amino Acid in hFLG[9-10] | Amino Acid in hFLG[AZT-mutein] |
|---|---|---|
| 130 | P | S |
| 134 | G | D |
| 145 | E | Q |
| 147 | A | S |
| 150 | K | R |
| 163 | R | S |
| 177 | E | G |
| 188 | R | Q |
| 193 | H | D |
| 197 | N | H |
| 235 | Q | H |
| 258 | T | R |
| 259 | D | H |

TABLE 3-continued

| Position | Amino Acid in hFLG[9-10] | Amino Acid in hFLG[AZT-mutein] |
|---|---|---|
| 262 | T | I |
| 264 | R | H |
| 265 | R | G |
| 267 | D | A |
| 270 | V | A |
| 272 | G | R |
| 276 | N | H |
| 293 | E | D |
| 316 | T | A |
| 319 | Q | R |
| 340 | S (absent) | S |
| 341 | E (absent) | E |
| 342 | S (absent) | S |

Example 10. Filaggrin Consensus Sequence

Figure 13A:
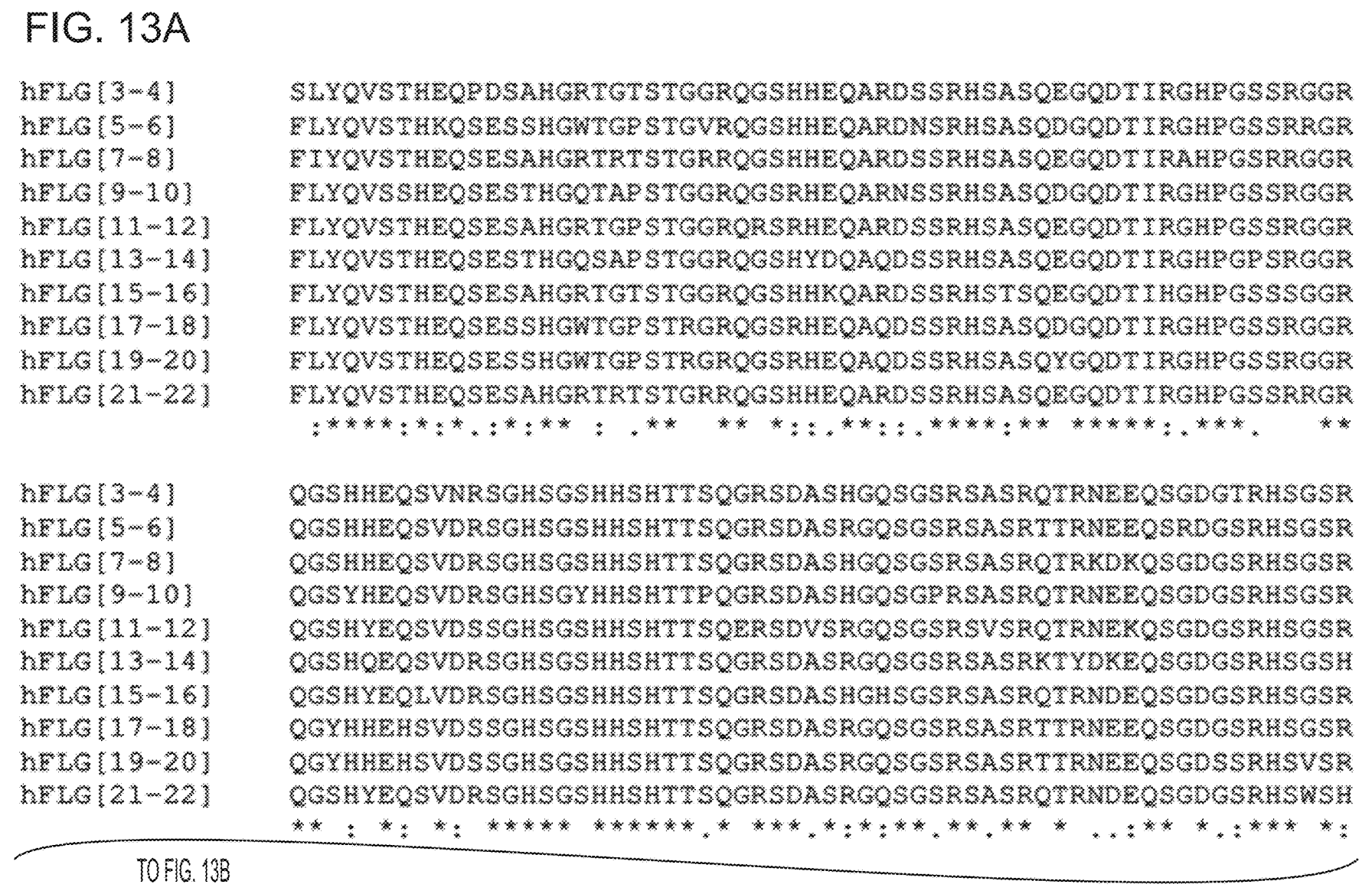

A human filaggrin consensus sequence was generated by alignment of filaggrin dimers hFLG[3-4], hFLG[5-6], hFLG [7-8], hFLG[9-10], hFLG[11-12], hFLG[13-14], hFLG[15-16], hFLG[17-18], hFLG[19-20], hFLG[21-22] as shown in FIG. 13A-13C. The consensus sequence shown as SEQ ID NO: 9 refers to the sequence formed from the most frequently occurring amino acids shown in the alignment in FIG. 13A-13C.

```
                                        SEQ ID NO: 9
XLYQVSTHXQXDSXHGXTXXSTXXRQXSHXXQAXXXSRHSXSQXGQ    100
DTIRGHPGXXXXGRQGXXXEXXVXXSGHSGXHHSHTTXQXRSDASH
GXSGXRSA

SRXTXXXXQSXDXTRHSXSRHHEXXSXAXXSXHSXXGQXXSXGXRX    200
SRXXGSSXSQDXDSXXHSEDSERXSXSASRNHXGSXXEQXRXGSRX
PXXHXEDR

AXHGHSADXSRKSGTXHXXXSSXGQAASSXEQARSSXGERHGSRHQ    300
XQSADSSXXSGXXHXQXSSAVXDSXXXGXSGSQATXXEGHSEDSDT
QSVSGXGX

XGXHQQSHXESXRXXSGXXSXRSXSFLY                      328
```

Example 11. Keratin Binding Assay to Measure Activity of Filaggrin

A keratin binding assay was used to measure activity of various hFLG[9-10] sequences set forth in SEQ ID NOs 1-9.
Keratin Extraction from Human Callus:

Keratins were extracted from human callus. One to two grams of callus was homogenized in 10 mL 5 mM Tris pH 7.4 with protease inhibitors using a BULLET BLENDER® bead beater. Homogenized tissue was centrifuged 10 000 rpm for 20 minutes at 4° C. The resulting pellet was resuspended in 0.05M tris pH 7.4 containing 8 M urea and 0.025 mM β-mercaptoethanol and mixed gently for 2 h at 37° C. The urea lysate was centrifuged 10 000 rpm for 10 minutes. The supernatant was dialyzed against 5 mM Tris pH7.4 overnight at 4° C. allowing the gradual assembly of keratin filaments.
Filaggrin—Keratin Binding Assay:

An aliquot of assembled callus keratin filaments (above section) was centrifuged 5 minutes at 10 000 RPM to remove insoluble contaminants. Wells were coated overnight at 4° C. with specified amount of keratin extract diluted in coating buffer to a final volume of 200 μL. Coating buffer was removed, wells were blocked with 200 μl 5% non-fat dry milk in PBST (PBS+0.05% TWEEN® 20) and incubated at 37° C. for 2 h. Blocking buffer was removed and a pre-determined amount (μg) of the appropriate human recombinant filaggrin protein, diluted in PBST to a final volume of 200 μL, was added and plates were incubated at 37° C. for 2 h. Plates were washed 3 times with 200 μL per well of PBST. For the detection of filaggrin binding, an anti-filaggrin IgY chicken antibody (RL-012-001B antibody 1/1000 in PBST) was added to the wells. For the detection of keratin (controls) 200 μL of a mouse pan-keratin antibody (Type II AE3 Ab at a dilution of 1/500 in PBST) was added to indicated wells. Primary antibodies were incubated at room temperature with shaking for 1 h. Primary antibodies were removed and plates washed 3 times with PBST. To all the wells containing the anti-chicken antibody a secondary alpaca anti-chicken antibody conjugated with horse radish peroxidase (HRP) was added at a dilution of 1/2000 in PBST. Wells containing the anti-keratin antibody received a goat anti-mouse antibody conjugated with HRP at a dilution of 1/500 in PBST. Plates were incubated at room temperature with shaking for 1 h. Plates were washed 3 times with PBST and 100 ul of 1-Step Ultra TMB substrate was added. Plates were incubated at room temperature until the appearance of blue color subsided, 15-20 minutes. The reaction was stopped by adding 100 μL of 2M HCL and absorbances were read on a spectrophotometer at 450-550 nm.

Figure 14:
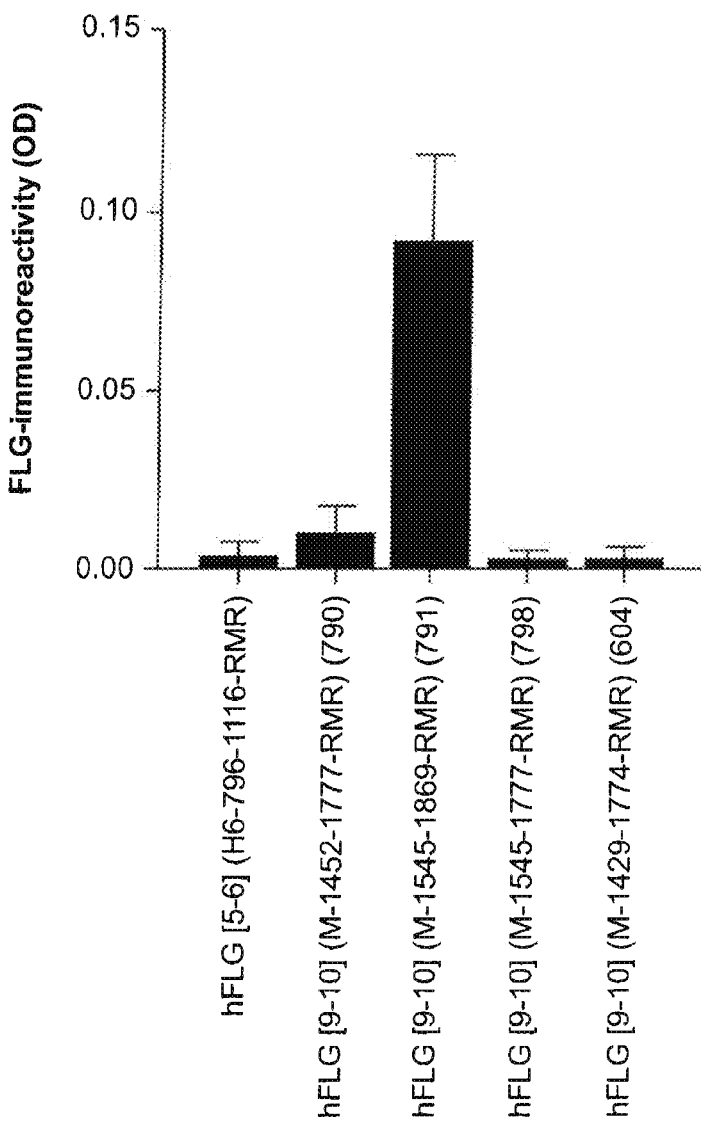
FIG. 14 is a graph that shows background FLG binding at 1 μg/well for 2 h at 37° C. (non specific binding—NSB).
Figure 15:
FIG. 15 is a graph that shows binding of hFLG segments to human callus keratin (NSB removed).
Figure 15:
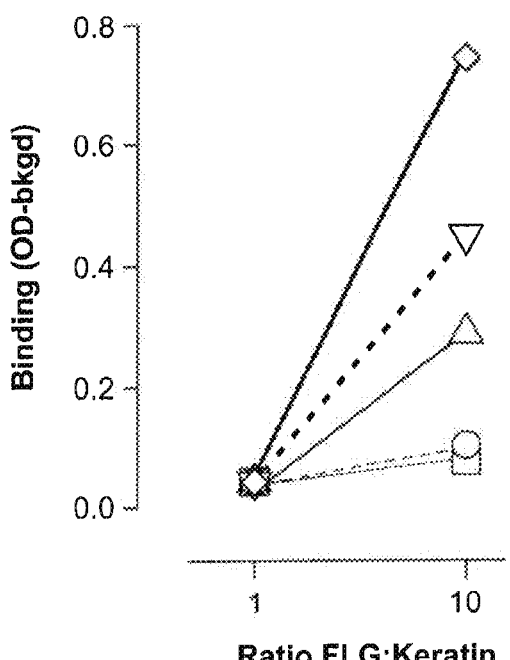
Figure 16:
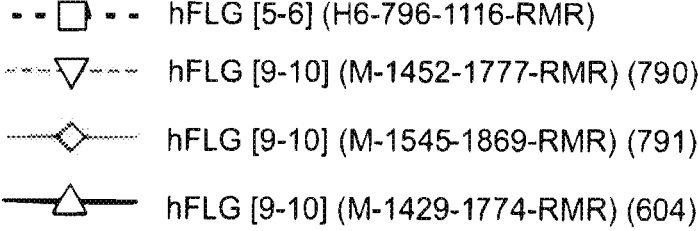
FIG. 16 is a graph that shows titration of IgY anti-hFLG.
Figure 16:
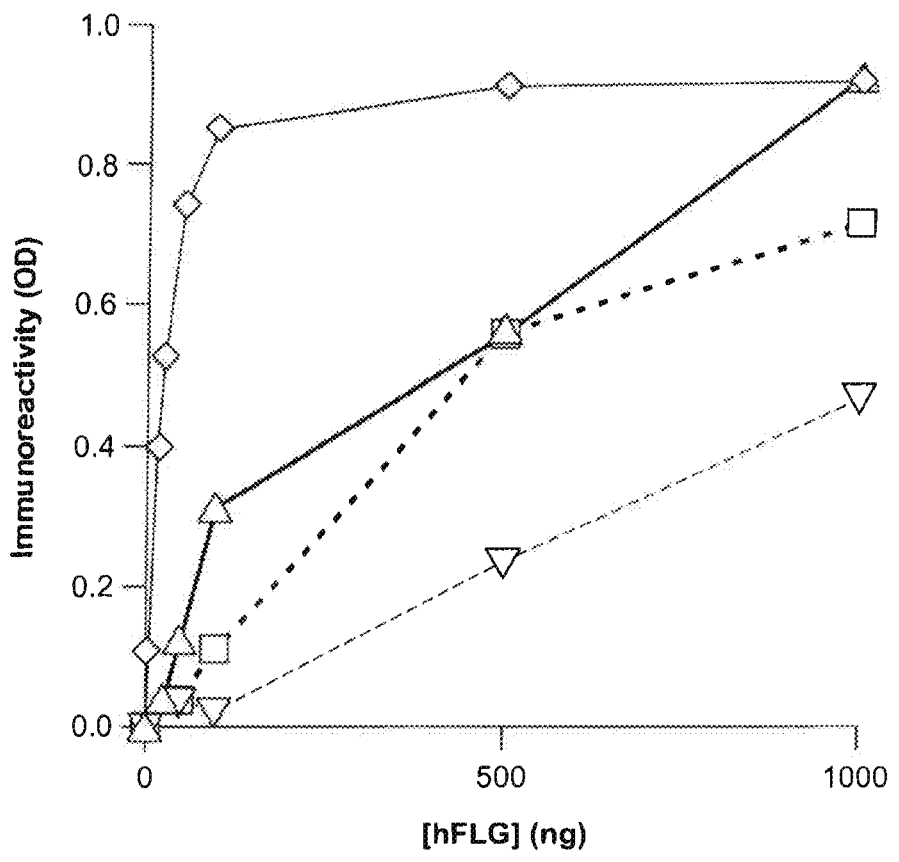

The results are shown in FIGS. 14-16, and demonstrate that there was differential binding to keratin among the hFLG sequences tested. FIG. 14 is a graph that shows background FLG binding at 1 μg/well for 2 h at 37° C. The results shown in FIG. 14 include non specific binding (NSB). FIG. 15 is a graph that shows the binding of various hFLG segments to human callus keratin (with NSB removed). FIG. 16 is a graph that shows titration of IgY anti-hFLG. As shown in FIGS. 14-16, hFLG[5-6] did not bind keratin, while the various hFLG[9-10] sequences that were tested showed binding to keratin.

Example 12. Activity of hFLG[9-10]-Secreting SE in Mice

A genetic IV mouse model (Flg−/−) will be used, as well as wild type mice to assess colonization dynamics of FLG-producing SE in vivo. Flg−/− mice are filaggrin deficient and exhibit dry, scaly skin. Despite marked decreases in natural moisturizing factor levels, which are filaggrin degradation products, stratum corneum (SC) hydration and TEWL are normal in Flg−/− mice. Antigens penetrate the Flg−/− SC more efficiently, leading to enhanced responses in hapten-induced contact hypersensitivity and higher serum levels of anti-ovalbumin (OVA) IgG(1) and IgE. Flg−/− mice are obtained from RIKEN BioResource Research Center (RIKEN BRC, Tsukuba, Ibaraki, Japan). Wild type mice (BALB/c) will also be used in this experiment.

The hFLG[9-10] sequences set forth in SEQ ID NOs 1-9 will be used in SE to Flg−/− and BALB/c mice. The study will be conducted for four weeks using five groups in each mouse type. Mice will be assigned into the following treatment groups: topical vehicle control (50% glycerol, 50% sterilized BHI medium), topical wild type SE ($1.0 \times 10^8$ CFU/cm$^2$ in 50% glycerol), and three doses of each of each filaggrin-secreting SE constructs (SE$^{FLG}$) ($10^6$, $10^7$, and $10^8$ CFU/cm$^2$ in 50% glycerol). Each solution will be applied to the same ear and tail on each mouse daily for seven days, and mice be assessed on days 7, 14, 30, and 60 for microbiome analyses to assess colonization dynamics and on days 7 and 14 for microscopy and histology to assess localization and macroscopic changes in the skin (e.g., any signs of adverse events such as inflammation), etc. 12 mice in each arm per mouse type will be used.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. A method of treating an inflammatory skin disease comprising administering to a mammalian subject in need thereof a therapeutically effective amount of a biotherapeutic composition comprising live recombinant *Staphylococcus epidermidis* comprising an expression vector, wherein the expression vector, or combination of bacteria, wherein the *Staphylococcus epidermidis* comprises (i) a first coding sequence comprising a nucleic acid sequence encoding a filaggrin (FLG) therapeutic polypeptide, wherein the therapeutic polypeptide consists of SEQ ID NO: 46;

(ii) a second coding sequence comprising a nucleic acid sequence encoding a cell penetrating peptide;

(iii) a third coding sequence comprising a nucleic acid sequence encoding an export signal; and (iv) a promoter operably linked to the first coding sequence, the second coding sequence and the third coding sequence, wherein the first coding sequence, the second coding sequence and the third-coding sequence, wherein the recombinant *Staphylococcus epidermidis* first coding sequence, the second coding sequence and the third-coding sequence are capable of expresses a filaggrin fusion product comprising the FLG therapeutic polypeptide.

2. The method of claim 1, wherein the skin disease is atopic dermatitis.

3. The method of claim 1, wherein the composition is applied topically.

4. The method of claim 1, wherein the export signal exports the filaggrin fusion product out of the recombinant bacterium.

5. The method of claim 1, wherein the cell penetrating peptide facilitates the entry of the filaggrin fusion product into a human keratinocyte.

6. The method of claim 1, wherein the first coding sequence, the second coding sequence and the third coding sequences are arranged in a single plasmid.

* * * * *